United States Patent [19]
Davis et al.

[11] Patent Number: 5,989,830
[45] Date of Patent: Nov. 23, 1999

[54] BIFUNCTIONAL OR BIVALENT ANTIBODY FRAGMENT ANALOGUE

[75] Inventors: Paul James Davis, Felmersham; Cornelis Paul Erik van der Logt; Martine Elisa Verhoeyen, both of Rushden; Steve Wilson, Goldington, all of United Kingdom

[73] Assignee: Unilever Patent Holdings BV, Vlaardingen, Netherlands

[21] Appl. No.: 08/860,174

[22] PCT Filed: Aug. 14, 1996

[86] PCT No.: PCT/EP96/03605

§ 371 Date: Jul. 31, 1997

§ 102(e) Date: Jul. 31, 1997

[87] PCT Pub. No.: WO97/14719

PCT Pub. Date: Apr. 24, 1997

[30] Foreign Application Priority Data

Oct. 16, 1995 [GB] United Kingdom .................. 95307332

[51] Int. Cl.[6] ............................ C12P 21/08; C12P 21/06; C07K 16/00; G01N 33/53
[52] U.S. Cl. .................... 435/7.1; 530/387.3; 530/387.1; 530/388.1; 435/69.1
[58] Field of Search .............................. 530/387.1, 387.3, 530/388.1; 435/7.1, 69.1

[56] References Cited

FOREIGN PATENT DOCUMENTS

WO 93/11161  6/1993  WIPO .

OTHER PUBLICATIONS

Burgess et al (J. Cell. Bio, III: 2129–2138), 1990.
Lazar et al (Mol & Cell Bio, 8: 1247–1252), 1988.
Tao et al (J. Immunol, 143: 2595–2601), 1989.
Bowie et al (Science 247: 1306–1310), 1990.
Klausner (Biotechnology, 4: 1042–1043), 1984.
Better et al (Science, 240: 1041–1043), 1988.
Holliger et al (PNAS, 30: 6444–6448), 1993.
Verhoeyen et al: "Antibody fragments for controlled delivery of therapeutic agents" Biochemical Society Transactions, vol. 23, No. 4, Jul. 18–21 1995, pp. 1067–1073 XP000565752, see the whole document.

*Primary Examiner*—Paula K. Hutzell
*Assistant Examiner*—Susan Ungar
*Attorney, Agent, or Firm*—Pillsbury Madison & Sutro LLP

[57] ABSTRACT

A bispecific or bivalent double head antibody fragment, which is composed of a binding complex containing two polypeptide chains, whereby one polypeptide chain has two times a variable domain of a heavy chain ($V_H$) in series and the other polypeptide chain has two times a variable domain of a light chain ($V_L$) in series, and the binding complex contains two pairs of variable domains ($V_H$–A//$V_L$–A and $V_H$–B//$V_L$–B), wherein said double head antibody fragments have binfunctional antigen binding activity. A process for producing such an antibody fragment is disclosed. An immunoassay is also provided for, wherein the improvement is the inclusion of a bispecific or bivalent double head antibody fragment, which is composed of a binding complex containing two polypeptide chains, whereby one polypeptide chain has two times a variable domain of a heavy chain ($V_H$) in series and the other polypeptide chain has two times a variable domain of a light chain ($V_L$) in series, as a binding means.

9 Claims, 44 Drawing Sheets

Fig. 4

```
         D   I   E   L   T   Q   S   P   A   S   L   S   A   S   V   G   E
GAATTCGGCCGACATCGAGCTCACCCAGTCTCCAGCCTCCCTTTCTGCGTCTGTGGAGA
EcoRI           SacI                                                      60

T   V   T   I   T   C   R   A   S   G   N   I   H   N   Y   L   A   W   Y   Q
AACTGTCACCATCACATGTCGAGCAAGTGGGAATATTCACAATTATTTAGCATGGTATCA
                                                                         120

Q   K   Q   G   K   S   P   Q   L   L   V   Y   Y   T   T   L   A   D   G
GCAGAAACAGGGAAAATCTCCTCAGCTCCTGGTCTATTATACAACAACCTTAGCAGATGG
                                                                         180

V   P   S   R   F   S   G   S   G   S   G   T   Q   Y   S   L   K   I   N   S
TGTGCCATCAAGGTTCAGTGGCAGTGGATCAGGAACACAATATTCTCTCAAGATCAACAG
                                                                         240

L   Q   P   E   D   F   G   S   Y   Y   C   Q   H   F   W   S   T   P   R   T
CCTGCAACCTGAAGATTTTGGGAGTTATTACTGTCAACATTTTTGGAGTACTCCTCGGAC
                                                                         300

F   G   G   G   T   K   L   E   I   K   R  |G   G   G   S   G   G   G   G
GTTCGGTGGAGGGACCAAGCTCGAGATCAAACGGGGTGGAGGCGGTTCAGGCGGAGGTGG
                     XhoI                                                360

S   G   G   G   G   S |Q   V   Q   L   Q   E   S   G   P   G   L   V   A   P
CTCTGGCGGTGGCGGATCGCAGGTGCAGCTGCAGGAGTCAGGACCTGGCCTGGTGGCGCC
                                  PstI                                   420

S   Q   S   L   S   I   T   C   T   V   S   G   F   S   L   T   G   Y   G   V
CTCACAGAGCCTGTCCATCACATGCACCGTCTCAGGGTTCTCATTAACCGGCTATGGTGT
                                                                         480

N   W   V   R   Q   P   P   G   K   G   L   E   W   L   G   M   I   W   G   D
AAACTGGGTTCGCCAGCCTCCAGGAAAGGGTCTGGAGTGGCTGGGAATGATTTGGGGTGA
                                                                         540

G   N   T   D   Y   N   S   A   L   K   S   R   L   S   I   S   K   D   N   S
TGGAAACACAGACTATAATTCAGCTCTCAAATCCAGACTGAGCATCAGCAAGGACAACTC
                                                                         600

K   S   Q   V   F   L   K   M   N   S   L   H   T   D   D   T   A   R   Y   Y
CAAGAGCCAAGTTTTCTTAAAAATGAACAGTCTGCACACTGATGACACAGCCAGGTACTA
                                                                         660

C   A   R   E   R   D   Y   R   L   D   Y   W   G   Q   G   T   T   V   T   V
CTGTGCCAGAGAGAGAGATTATAGGCTTGACTACTGGGGCCAAGGGACCACGGTCACCGT
                                                                         720

S   S   *
CTCCTCATGATAAGCTT
        HindIII 737

DIELTQSPAS---GGGTKLEIKR   = VLLys
GGGGSGGGGSGGGGS          = Linker
QVQLQESGPG---GQGTTVTVSS  = VHLys
```

Fig. 5

```
                                      M  K  Y  L  L  P  T  A
pelB      AAGCTTGCAAATTCTATTTCAAGGAGACAGTCATAATGAAATACCTATTGCCTACGGCAG
LEADER
          A  A  G  L  L  L  A  A  Q  P  A  M  A  Q  V  Q  L  Q  Q
          CCGCTGGATTGTTATTACTCGCTGCCCAACCAGCGATGGCCCAGGTGCAGCTGCAGCAGT S  G  P  E  L  V  K  P  G  A  S  V  K  M  S  C  K  A  S  G
          CAGGACCTGAGCTGGTAAAGCCTGGGGCTTCAGTGAAGATGTCCTGCAAGGCTTCTGGAT Y  T  F  T  S  Y  V  M  H  W  V  K  Q  K  P  G  Q  G  L  E
          ACACATTCACTAGCTATGTTATGCACTGGGTGAAACAGAAGCCTGGGCAGGGCCTTGAGT VH3418    W  I  G  Y  I  Y  P  Y  N  D  G  T  K  Y  N  E  K  F  K  G
          GGATTGGATATATTTATCCTTACAATGATGGTACTAAGTACAATGAGAAGTTCAAAGGCA K  A  T  L  T  S  D  K  S  S  S  T  A  Y  M  E  L  S  S  L
          AGGCCACACTGACTTCAGACAAATCCTCCAGCACAGCCTACATGGAGCTCAGCAGCCTGA T  S  E  D  S  A  V  Y  Y  C  S  R  R  F  D  Y  W  G  Q  G
          CCTCTGAGGACTCTGCGGTCTATTACTGTTCAAGACGCTTTGACTACTGGGGCCAAGGGA T  T  V  T  V  S  S
          CCACGGTCACCGTCTCCTCATAATAAGAGCTATGGGAGCTTGCATGCAAATTCTATTTCA M  K  Y  L  L  P  T  A  A  A  G  L  L  L
          AGGAGACAGTCATAATGAAATACCTATTGCCTACGGCAGCCGCTGGATTGTTATTACTCG
pelB
LEADER    A  A  Q  P  A  M  A  D  I  E  L  T  Q  S  P  S  S  M  Y  A
          CTGCCCAACCAGCGATGGCCGACATCGAGCTCACCCAGTCTCCATCTTCCATGTATGCAT S  L  G  E  R  I  T  I  T  C  K  A  S  Q  D  I  N  T  Y  L
          CTCTAGGAGAGAGAATCACTATCACTTGCAAGGCGAGTCAGGACATTAATACCTATTTAA T  W  F  Q  Q  K  P  G  K  S  P  K  T  L  I  Y  R  A  N  R
          CCTGGTTCCAGCAGAAACCAGGGAAATCTCCCAAGACCCTGATCTATCGTGCAAACAGAT VL3418    L  L  D  G  V  P  S  R  F  S  G  S  G  S  G  Q  D  Y  S  L
          TGCTAGATGGGGTCCCATCAAGGTTCAGTGGCAGTGGATCTGGGCAAGATTATTCTCTCA T  I  S  S  L  D  Y  E  D  M  G  I  Y  Y  C  L  Q  Y  D  E
          CCATCAGCAGCCTGGACTATGAAGATATGGGAATTTATTATTGTCTACAATATGATGAGT L  Y  T  F  G  G  G  T  K  L  E  I  K  R
          TGTACACGTTCGGAGGGGGGACCAAGCTCGAGATCAAACGGTAATAATGATCAAACGGT

ATAAGGATCCAGCTCGAATTC
```

Fig. 6

```
                                            M  K  Y  L  L  P  T
pelB      AAGCTTGCATGCAAATTCTATTTCAAGGAGACAGTCATAATGAAATACCTATTGCCTACG
LEADER
          A  A  A  G  L  L  L  L  A  A  Q  P  A  M  A  Q  V  Q  L  Q
          GCAGCCGCTGGATTGTTATTACTCGCTGCCCAACCAGCGATGGCCCAGGTGCAGCTGCAG E  S  G  G  D  L  V  K  P  G  G  S  L  T  L  S  C  A  T  S
          GAGTCAGGGGGAGACTTAGTGAAGCCTGGAGGGTCCCTGACACTCTCCTGTGCAACCTCT G  F  T  F  S  S  Y  A  F  S  W  V  R  Q  T  S  D  K  S  L
          GGATTCACTTTCAGTAGTTATGCCTTTTCTTGGGTCCGCCAGACCTCAGACAAGAGTCTG E  W  V  A  I  S  S  T  D  T  Y  T  Y  Y  S  D  N  V  K
VH4715    GAGTGGGTCGCAACCATCAGTAGTACTGATACTTATACCTATTATTCAGACAATGTGAAG G  R  F  T  I  S  R  D  N  G  K  N  T  L  Y  L  Q  M  S  S
          GGGCGCTTCACCATCTCCAGAGACAATGGCAAGAACACCCTGTACCTGCAAATGAGCAGT L  K  S  E  D  T  A  V  Y  Y  C  A  R  H  G  Y  Y  G  K  G
          CTGAAGTCTGAGGACACAGCCGTGTATTACTGTGCAAGACATGGGTACTATGGTAAAGGC Y  F  D  Y  W  G  Q  G  T  T  V  T  V  S  S
          TATTTTGACTACTGGGGCCAAGGGACCACGGTCACCGTCTCCTCATAATAAGAGCTATGG M  K  Y  L  L  P  T
pelB      GAGCTTGCATGCAAATTCTATTTCAAGGAGACAGTCATAATGAAATACCTATTGCCTACG
LEADER
          A  A  A  G  L  L  L  L  A  A  Q  P  A  M  A  D  I  E  L  T
          GCAGCCGCTGGATTGTTATTACTCGCTGCCCAACCAGCGATGGCCGACATCGAGCTCACT Q  S  P  F  S  L  T  V  T  A  G  E  K  V  T  M  N  C  K  S
          CAGTCTCCATTCTCCCTGACTGTGACAGCAGGAGAGAAGGTCACTATGAATTGCAAGTCC G  Q  S  L  L  N  S  V  N  Q  R  N  Y  L  T  W  Y  Q  Q  K
          GGTCAGAGTCTGTTAAACAGTGTAAATCAGAGGAACTACTTGACCTGGTACCAGCAGAAG P  G  Q  P  P  K  L  L  I  Y  W  A  S  T  R  E  S  G  V  P
VL4715    CCAGGGCAGCCTCCTAAACTGTTGATCTACTGGGCATCCACTAGGGAATCTGGAGTCCCT D  R  F  T  A  S  G  S  G  T  D  F  T  L  T  I  S  S  V  Q
          GATCGCTTCACAGCCAGTGGATCTGGAACAGATTTCACTCTCACCATCAGCAGTGTGCAG A  E  D  L  A  V  Y  Y  C  Q  N  D  Y  T  Y  P  F  T  F  G
          GCTGAAGACCTGGCAGTTTATTACTGTCAGAATGATTATACTTATCCGTTCACGTTCGGA Myc-tag   G  G  T  K  L  E  I  K  R  (E  Q  K  L  I  S  E  E  D  L  N)
          GGGGGGACCAAGCTCGAGATCAAACGGGAACAAAAACTCATCTCAGAAGAGGATCTGAAT

TAATAAGATCAAACGGTAATAAGGATCCAGCTCGAATTC
```

Fig. 7

```
                                                                M  K  Y  L  L  P  T
pelB        AAGCTTGCATGCAAATTCTATTTCAAGGAGACAGTCATAATGAAATACCTATTGCCTACG
LEADER
             A  A  A  G  L  L  L  A  A  Q  P  A  M  A  Q  V  Q  L  Q
            GCAGCCGCTGGATTGTTATTACTCGCTGCCCAACCAGCGATGGCCCAGGTGCAGCTGCAG E  S  G  G  D  L  V  K  P  G  G  S  L  T  L  S  C  A  T  S
            GAGTCAGGGGGAGACTTAGTGAAGCCTGGAGGGTCCCTGACACTCTCCTGTGCAACCTCT G  F  T  F  S  S  Y  A  F  S  W  V  R  Q  T  S  D  K  S  L
            GGATTCACTTTCAGTAGTTATGCCTTTTCTTGGGTCCGCCAGACCTCAGACAAGAGTCTG E  W  V  A  T  I  S  S  T  D  T  Y  T  Y  Y  S  D  N  V  K
VH4715      GAGTGGGTCGCAACCATCAGTAGTACTGATACTTATACCTATTATTCAGACAATGTGAAG G  R  F  T  I  S  R  D  N  G  K  N  T  L  Y  L  Q  M  S  S
            GGGCGCTTCACCATCTCCAGAGACAATGGCAAGAACACCCTGTACCTGCAAATGAGCAGT L  K  S  E  D  T  A  V  Y  Y  C  A  R  H  G  Y  Y  G  K  G
            CTGAAGTCTGAGGACACAGCCGTGTATTACTGTGCAAGACATGGGTACTATGGTAAAGGC Y  F  D  Y  W  G  Q  G  T  T  V  T  V  S  S  G  G  G  G  S
LINKER      TATTTTGACTACTGGGGCCAAGGGACCACGGTCACCGTCTCCTCAGGTGGAGGCGGTTCA G  G  G  S  G  G  G  G  S  D  I  E  L  T  Q  S  P  F  S
            GGCGGAGGTGGCTCTGGCGGTGGCGGATCGGACATCGAGCTCACTCAGTCTCCATTCTCC L  T  V  T  A  G  E  K  V  T  M  N  C  K  S  G  Q  S  L  L
            CTGACTGTGACAGCAGGAGAGAAGGTCACTATGAATTGCAAGTCCGGTCAGAGTCTGTTA N  S  V  N  Q  R  N  Y  L  T  W  Y  Q  Q  K  P  G  Q  P  P
            AACAGTGTAAATCAGAGGAACTACTTGACCTGGTACCAGCAGAAGCCAGGGCAGCCTCCT K  L  L  I  Y  W  A  S  T  R  E  S  G  V  P  D  R  F  T  A
VL4715      AAACTGTTGATCTACTGGGCATCCACTAGGGAATCTGGAGTCCCTGATCGCTTCACAGCC S  G  S  G  T  D  F  T  L  T  I  S  S  V  Q  A  E  D  L  A
            AGTGGATCTGGAACAGATTTCACTCTCACCATCAGCAGTGTGCAGGCTGAAGACCTGGCA V  Y  Y  C  Q  N  D  Y  T  Y  P  F  T  F  G  G  G  T  K  L
            GTTTATTACTGTCAGAATGATTATACTTATCCGTTCACGTTCGGAGGGGGGACCAAGCTC Myc-tag      E  I  K  R  E  Q  K  L  I  S  E  E  D  L  N
            GAGATCAAACGGGAACAAAAACTCATCTCAGAAGAGGATCTGAATTAATAAGATCAAACG

GTAATAAGGATCCAGCTCGAATTC
```

Fig. 8A

```
                                         M  K  Y  L  L  P  T
         AAGCTTGCATGCAAATTCTATTTCAAGGAGACAGTCATAATGAAATACCTATTGCCTACG pelB      A  A  A  G  L  L  L  L  A  A  Q  P  A  M  A  Q  V  Q  L  Q
LEADER   GCAGCCGCTGGATTGTTATTACTCGCTGCCCAACCAGCGATGGCCCAGGTGCAGCTGCAG E  S  G  G  D  L  V  K  P  G  G  S  L  T  L  S  C  A  T  S
         GAGTCAGGGGGAGACTTAGTGAAGCCTGGAGGGTCCCTGACACTCTCCTGTGCAACCTCT VH4715    G  F  T  F  S  S  Y  A  F  S  W  V  R  Q  T  S  D  K  S  L
         GGATTCACTTTCAGTAGTTATGCCTTTTCTTGGGTCCGCCAGACCTCAGACAAGAGTCTG E  W  V  A  T  I  S  S  T  D  T  Y  T  Y  Y  S  D  N  V  K
         GAGTGGGTCGCAACCATCAGTAGTACTGATACTTATACCTATTATTCAGACAATGTGAAG G  R  F  T  I  S  R  D  N  G  K  N  T  L  Y  L  Q  M  S  S
         GGGCGCTTCACCATCTCCAGAGACAATGGCAAGAACACCCTGTACCTGCAAATGAGCAGT L  K  S  E  D  T  A  V  Y  Y  C  A  R  H  G  Y  Y  G  K  G
         CTGAAGTCTGAGGACACAGCCGTGTATTACTGTGCAAGACATGGGTACTATGGTAAAGGC Y  F  D  Y  W  G  Q  G  T  T  V  T  V  S  S  G  G  G  G  S
         TATTTTGACTACTGGGGCCAAGGGACCACGGTCACCGTCTCCTCAGGTGGAGGCGGTTCA LINKER    G  G  G  S  G  G  G  G  S  A  G  S  A  Q  V  Q  L  Q  Q
         GGCGGAGGTGGCTCTGGCGGTGGCGGATCGGCCGGTTCGGCCCAGGTCCAGCTGCAACAG S  G  P  E  L  V  K  P  G  A  S  V  K  M  S  C  K  A  S  G
         TCAGGACCTGAGCTGGTAAAGCCTGGGGCTTCAGTGAAGATGTCCTGCAAGGCTTCTGGA Y  T  F  T  S  Y  V  M  H  W  V  K  Q  K  P  G  Q  G  L  E
         TACACATTCACTAGCTATGTTATGCACTGGGTGAAACAGAAGCCTGGGCAGGGCCTTGAG W  I  G  Y  I  Y  P  Y  N  D  G  T  K  Y  N  E  K  F  K  G
VH3418   TGGATTGGATATATTTATCCTTACAATGATGGTACTAAGTACAATGAGAAGTTCAAAGGC K  A  T  L  T  S  D  K  S  S  S  T  A  Y  M  E  L  S  S  L
         AAGGCCACACTGACTTCAGACAAATCCTCCAGCACAGCCTACATGGAGCTCAGCAGCCTG T  S  E  D  S  A  V  Y  Y  C  S  R  R  F  D  Y  W  G  Q  G
         ACCTCTGAGGACTCTGCGGTCTATTACTGTTCAAGACGCTTTGACTACTGGGGCCAAGGG T  T  V  T  V  S  S
         ACCACCGTCACCGTCTCCTCATAATAAGCTAGCGGAGCTGCATGCAAATTCTATTTCAAG pelB                   M  K  Y  L  L  P  T  A  A  A  G  L  L  L  A
LEADER   GAGACAGTCATAATGAAATACCTATTGCCTACGGCAGCCGCTGGATTGTTATTACTCGCT A  Q  P  A  M  A  D  I  E  L  T  Q  S  P  S  S  M  Y  A  S
         GCCCAACCAGCGATGGCCGACATCGAGCTCACCCAGTCTCCATCTTCCATGTATGCATCT L  G  E  R  I  T  I  T  C  K  A  S  Q  D  I  N  T  Y  L  T
VL3418   CTAGGAGAGAGAATCACTATCACTTGCAAGGCGAGTCAGGACATTAATACCTATTTAACC W  F  Q  Q  K  P  G  K  S  P  K  T  L  I  Y  R  A  N  R  L
         TGGTTCCAGCAGAAACCAGGGAAATCTCCCAAGACCCTGATCTATCGTGCAAACAGATTG
```

Fig. 8B

```
           L  D  G  V  P  S  R  F  S  G  S  G  S  G  Q  D  Y  S  L  T
           CTAGATGGGGTCCCATCAAGGTTCAGTGGCAGTGGATCTGGGCAAGATTATTCTCTCACC

I  S  S  L  D  Y  E  D  M  G  I  Y  Y  C  L  Q  Y  D  E  L
           ATCAGCAGCCTGGACTATGAAGATATGGGAATTTATTATTGTCTACAATATGATGAGTTG

Y  T  F  G  G  G  T  K  L  E  I  K  R  G  G  G  G  S  G  G
           TACACGTTCGGAGGGGGGACCAAGCTCGAGATCAAACGGGGTGGAGGCGGTTCAGGCGGA

LINKER     G  G  S  G  G  G  V  D  I  E  L  T  Q  S  P  F  S  L  T
           GGTGGCTCTGGCGGTGGCGGAGTCGACATCGAACTCACTCAGTCTCCATTCTCCCTGACT

V  T  A  G  E  K  V  T  M  N  C  K  S  G  Q  S  L  L  N  S
           GTGACAGCAGGAGAGAAGGTCACTATGAATTGCAAGTCCGGTCAGAGTCTGTTAAACAGT

V  N  Q  R  N  Y  L  T  W  Y  Q  Q  K  P  G  Q  P  P  K  L
           GTAAATCAGAGGAACTACTTGACCTGGTACCAGCAGAAGCCAGGGCAGCCTCCTAAACTG

VL4715     L  I  Y  W  A  S  T  R  E  S  G  V  P  D  R  F  T  A  S  G
           TTGATCTACTGGGCATCCACTAGGGAATCTGGAGTCCCTGATCGCTTCACAGCCAGTGGA

S  G  T  D  F  T  L  T  I  S  S  V  Q  A  E  D  L  A  V  Y
           TCTGGAACAGATTTCACTCTCACCATCAGCAGTGTGCAGGCTGAAGACCTGGCAGTTTAT

Y  C  Q  N  D  Y  T  Y  P  F  T  F  G  G  G  T  K  L  E  I
           TACTGTCAGAATGATTATACTTATCCGTTCACGTTCGGAGGGGGGACCAAGCTCGAAATC

K  R
           AAACGGTAATAAGCGGCCGCGAATTC
```

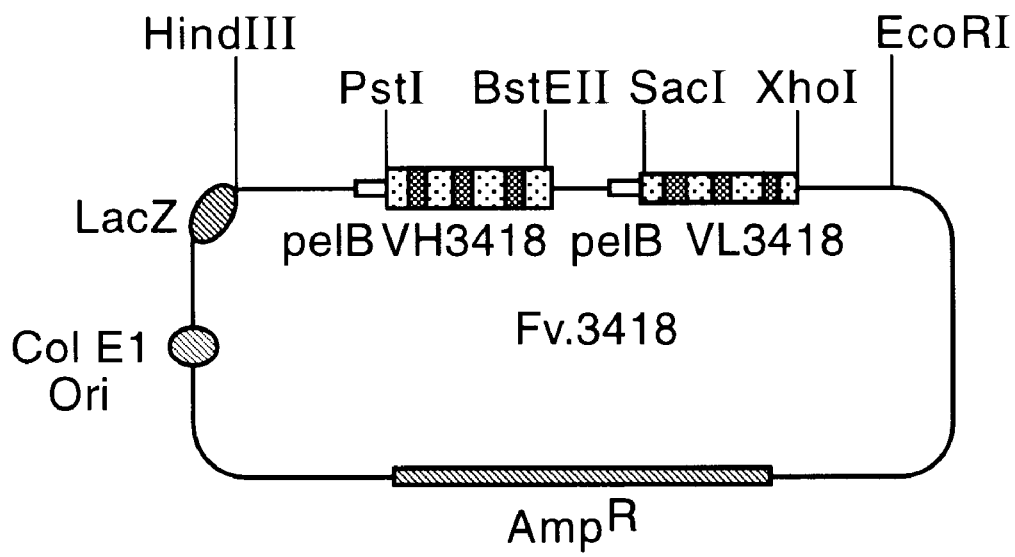
Fig. 37A
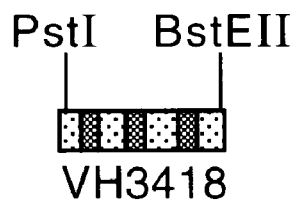

Fig. 43
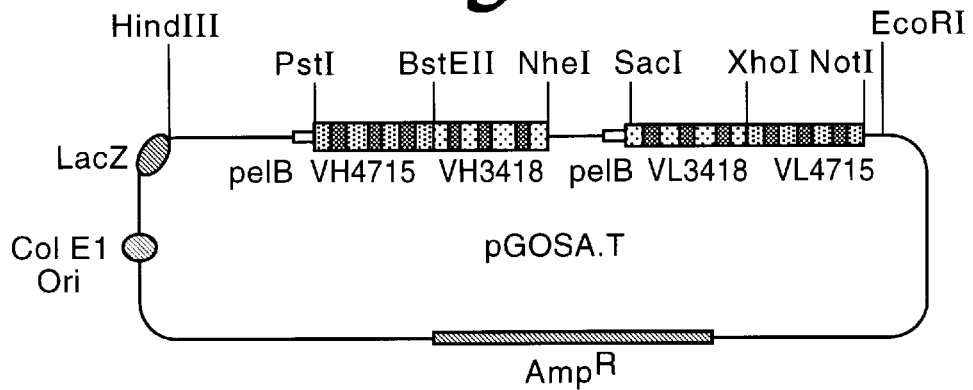
1) REMOVE HindIII/NheI VH4715-VH3418 FRAGMENT FROM pGOSA.T
2) FILL IN ENDS WITH KLENOW DNA POLYMERASE
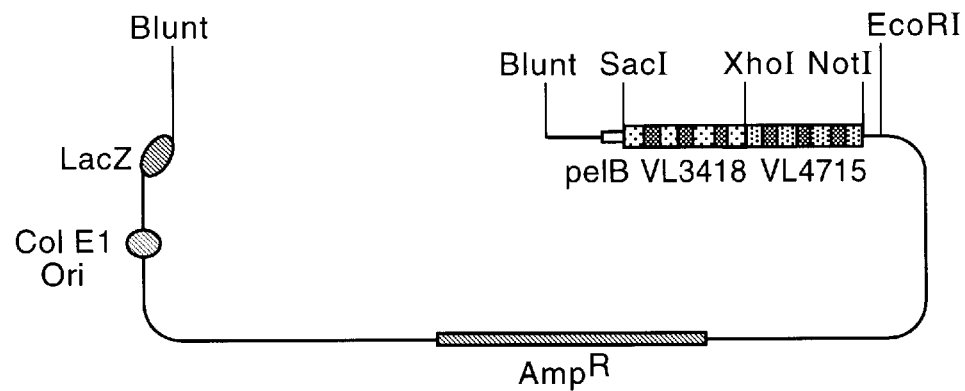
CLOSE VECTOR
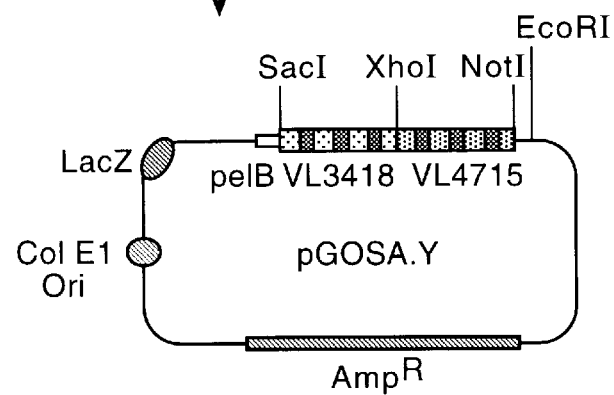

SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
      (A) LENGTH: 737 base pairs
      (B) TYPE: nucleic acid
      (C) STRANDEDNESS: double
      (D) TOPOLOGY: linear (ii) MOLECULE TYPE: other nucleic acid
      (A) DESCRIPTION: /desc = "cDNA domains with synthetic
          linker(s)"

```
       (vii) IMMEDIATE SOURCE:
             (B) CLONE: EcoRI-HindIII insert of pUR4124

(ix) FEATURE:
            (A) NAME/KEY: CDS
            (B) LOCATION:11..730
            (D) OTHER INFORMATION:/product= "VLlys-GS-VHlys"

(ix) FEATURE:
            (A) NAME/KEY: mat_peptide
            (B) LOCATION:11..334
            (D) OTHER INFORMATION:/product= "VLlys"

(ix) FEATURE:
            (A) NAME/KEY: misc_RNA
            (B) LOCATION:335..379
            (D) OTHER INFORMATION:/product= "(Gly4Ser)3 linker"

(ix) FEATURE:
            (A) NAME/KEY: mat_peptide
            (B) LOCATION:380..727
            (D) OTHER INFORMATION:/product= "VHlys"

(xi) SEQUENCE DESCRIPTION: SEQ ID NO: 1:

GAATTCGGCC GAC ATC GAG CTC ACC CAG TCT CCA GCC TCC CTT TCT GCG        49
           Asp Ile Glu Leu Thr Gln Ser Pro Ala Ser Leu Ser Ala
           1               5                   10

TCT GTG GGA GAA ACT GTC ACC ATC ACA TGT CGA GCA AGT GGG AAT ATT       97
Ser Val Gly Glu Thr Val Thr Ile Thr Cys Arg Ala Ser Gly Asn Ile
    15              20                  25

CAC AAT TAT TTA GCA TGG TAT CAG CAG AAA CAG GGA AAA TCT CCT CAG       145
His Asn Tyr Leu Ala Trp Tyr Gln Gln Lys Gln Gly Lys Ser Pro Gln
30              35                  40                  45

CTC CTG GTC TAT TAT ACA ACA ACC TTA GCA GAT GGT GTG CCA TCA AGG       193
Leu Leu Val Tyr Tyr Thr Thr Thr Leu Ala Asp Gly Val Pro Ser Arg
            50                  55                  60

TTC AGT GGC AGT GGA TCA GGA ACA CAA TAT TCT CTC AAG ATC AAC AGC       241
Phe Ser Gly Ser Gly Ser Gly Thr Gln Tyr Ser Leu Lys Ile Asn Ser
            65                  70                  75

CTG CAA CCT GAA GAT TTT GGG AGT TAT TAC TGT CAA CAT TTT TGG AGT       289
Leu Gln Pro Glu Asp Phe Gly Ser Tyr Tyr Cys Gln His Phe Trp Ser
        80                  85                  90

ACT CCT CGG ACG TTC GGT GGA GGG ACC AAG CTC GAG ATC AAA CGG GGT       337
Thr Pro Arg Thr Phe Gly Gly Gly Thr Lys Leu Glu Ile Lys Arg Gly
        95                  100                 105

GGA GGC GGT TCA GGC GGA GGT GGC TCT GGC GGT GGC GGA TCG CAG GTG       385
Gly Gly Gly Ser Gly Gly Gly Gly Ser Gly Gly Gly Gly Ser Gln Val
110             115                 120                 125

CAG CTG CAG GAG TCA GGA CCT GGC CTG GTG GCG CCC TCA CAG AGC CTG       433
Gln Leu Gln Glu Ser Gly Pro Gly Leu Val Ala Pro Ser Gln Ser Leu
            130                 135                 140

TCC ATC ACA TGC ACC GTC TCA GGG TTC TCA TTA ACC GGC TAT GGT GTA       481
Ser Ile Thr Cys Thr Val Ser Gly Phe Ser Leu Thr Gly Tyr Gly Val
            145                 150                 155

AAC TGG GTT CGC CAG CCT CCA GGA AAG GGT CTG GAG TGG CTG GGA ATG       529
Asn Trp Val Arg Gln Pro Pro Gly Lys Gly Leu Glu Trp Leu Gly Met
        160                 165                 170

ATT TGG GGT GAT GGA AAC ACA GAC TAT AAT TCA GCT CTC AAA TCC AGA       577
Ile Trp Gly Asp Gly Asn Thr Asp Tyr Asn Ser Ala Leu Lys Ser Arg
175                 180                 185

CTG AGC ATC AGC AAG GAC AAC TCC AAG AGC CAA GTT TTC TTA AAA ATG       625
Leu Ser Ile Ser Lys Asp Asn Ser Lys Ser Gln Val Phe Leu Lys Met
190                 195                 200                 205

AAC AGT CTG CAC ACT GAT GAC ACA GCC AGG TAC TAC TGT GCC AGA GAG       673
Asn Ser Leu His Thr Asp Asp Thr Ala Arg Tyr Tyr Cys Ala Arg Glu
            210                 215                 220
```

```
AGA GAT TAT AGG CTT GAC TAC TGG GGC CAA GGG ACC ACG GTC ACC GTC      721
Arg Asp Tyr Arg Leu Asp Tyr Trp Gly Gln Gly Thr Thr Val Thr Val
        225                 230                 235

TCC TCA TGA TAAGCTT                                                   737
Ser Ser
```

(2) INFORMATION FOR SEQ ID NO: 2:

(i) SEQUENCE CHARACTERISTICS:
        (A) LENGTH: 239 amino acids
        (B) TYPE: amino acid
        (D) TOPOLOGY: linear (ii) MOLECULE TYPE: protein (xi) SEQUENCE DESCRIPTION: SEQ ID NO: 2:

```
Asp Ile Glu Leu Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Tyr Thr Thr Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
                85                  90                  95

Thr Phe Gly Gly Gly Thr Lys Leu Glu Ile Lys Arg Gly Gly Gly Gly
            100                 105                 110

Ser Gly Gly Gly Gly Ser Gly Gly Gly Ser Gln Val Gln Leu Gln
        115                 120                 125

Glu Ser Gly Pro Gly Leu Val Ala Pro Ser Gln Ser Leu Ser Ile Thr
    130                 135                 140

Cys Thr Val Ser Gly Phe Ser Leu Thr Gly Tyr Gly Val Asn Trp Val
145                 150                 155                 160

Arg Gln Pro Pro Gly Lys Gly Leu Glu Trp Leu Gly Met Ile Trp Gly
                165                 170                 175

Asp Gly Asn Thr Asp Tyr Asn Ser Ala Leu Lys Ser Arg Leu Ser Ile
            180                 185                 190

Ser Lys Asp Asn Ser Lys Ser Gln Val Phe Leu Lys Met Asn Ser Leu
        195                 200                 205

His Thr Asp Asp Thr Ala Arg Tyr Tyr Cys Ala Arg Glu Arg Asp Tyr
    210                 215                 220

Arg Leu Asp Tyr Trp Gly Gln Gly Thr Thr Val Thr Val Ser Ser
225                 230                 235
```

(2) INFORMATION FOR SEQ ID NO: 3:

(i) SEQUENCE CHARACTERISTICS:
        (A) LENGTH: 920 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "cDNA domains with synthetic
            linker(s)"

(vii) IMMEDIATE SOURCE:
        (B) CLONE: HindIII-EcoRI insert Fv.3418

(ix) FEATURE:
    (A) NAME/KEY: CDS
    (B) LOCATION:36..443
    (D) OTHER INFORMATION:/product= "pelB-VH3418"

(ix) FEATURE:
    (A) NAME/KEY: sig_peptide
    (B) LOCATION:36..101
    (D) OTHER INFORMATION:/product= "pectate lyase"

(ix) FEATURE:
    (A) NAME/KEY: mat_peptide
    (B) LOCATION:102..440
    (D) OTHER INFORMATION:/product= "VH3418"

(ix) FEATURE:
    (A) NAME/KEY: CDS
    (B) LOCATION:495..884
    (D) OTHER INFORMATION:/product= "pelB-VL4318"

(ix) FEATURE:
    (A) NAME/KEY: sig_peptide
    (B) LOCATION:495..560
    (D) OTHER INFORMATION: /product= "pectate lyase"

(ix) FEATURE:
    (A) NAME/KEY: mat_peptide
    (B) LOCATION:561..881
    (D) OTHER INFORMATION:/product= "VL3418"

(xi) SEQUENCE DESCRIPTION: SEQ ID NO: 3:

```
AAGCTTGCAA ATTCTATTTC AAGGAGACAG TCATA ATG AAA TAC CTA TTG CCT             53
                                       Met Lys Tyr Leu Leu Pro
                                       -22         -20

ACG GCA GCC GCT GGA TTG TTA TTA CTC GCT GCC CAA CCA GCG ATG GCC           101
Thr Ala Ala Ala Gly Leu Leu Leu Leu Ala Ala Gln Pro Ala Met Ala
    -15                 -10                 -5

CAG GTG CAG CTG CAG CAG TCA GGA CCT GAG CTG GTA AAG CCT GGG GCT           149
Gln Val Gln Leu Gln Gln Ser Gly Pro Glu Leu Val Lys Pro Gly Ala
1               5                   10                  15

TCA GTG AAG ATG TCC TGC AAG GCT TCT GGA TAC ACA TTC ACT AGC TAT           197
Ser Val Lys Met Ser Cys Lys Ala Ser Gly Tyr Thr Phe Thr Ser Tyr
            20                  25                  30

GTT ATG CAC TGG GTG AAA CAG AAG CCT GGG CAG GGC CTT GAG TGG ATT           245
Val Met His Trp Val Lys Gln Lys Pro Gly Gln Gly Leu Glu Trp Ile
        35                  40                  45

GGA TAT ATT TAT CCT TAC AAT GAT GGT ACT AAG TAC AAT GAG AAG TTC           293
Gly Tyr Ile Tyr Pro Tyr Asn Asp Gly Thr Lys Tyr Asn Glu Lys Phe
50                  55                  60

AAA GGC AAG GCC ACA CTG ACT TCA GAC AAA TCC TCC AGC ACA GCC TAC           341
Lys Gly Lys Ala Thr Leu Thr Ser Asp Lys Ser Ser Ser Thr Ala Tyr
65                  70                  75                  80

ATG GAG CTC AGC AGC CTG ACC TCT GAG GAC TCT GCG GTC TAT TAC TGT           389
Met Glu Leu Ser Ser Leu Thr Ser Glu Asp Ser Ala Val Tyr Tyr Cys
                85                  90                  95

TCA AGA CGC TTT GAC TAC TGG GGC CAA GGG ACC ACG GTC ACC GTC TCC           437
Ser Arg Arg Phe Asp Tyr Trp Gly Gln Gly Thr Thr Val Thr Val Ser
                100                 105                 110

TCA TAA TAAGAGCTAT GGGAGCTTGC ATGCAAATTC TATTTCAAGG AGACAGTCAT           493
Ser

A ATG AAA TAC CTA TTG CCT ACG GCA GCC GCT GGA TTG TTA TTA CTC             539
  Met Lys Tyr Leu Leu Pro Thr Ala Ala Ala Gly Leu Leu Leu Leu
  -22         -20                 -15                 -10

GCT GCC CAA CCA GCG ATG GCC GAC ATC GAG CTC ACC CAG TCT CCA TCT           587
Ala Ala Gln Pro Ala Met Ala Asp Ile Glu Leu Thr Gln Ser Pro Ser
            -5                  1                   5
```

```
TCC ATG TAT GCA TCT CTA GGA GAG AGA ATC ACT ATC ACT TGC AAG GCG      635
Ser Met Tyr Ala Ser Leu Gly Glu Arg Ile Thr Ile Thr Cys Lys Ala
 10              15                  20                  25

AGT CAG GAC ATT AAT ACC TAT TTA ACC TGG TTC CAG CAG AAA CCA GGG      683
Ser Gln Asp Ile Asn Thr Tyr Leu Thr Trp Phe Gln Gln Lys Pro Gly
             30                  35                  40

AAA TCT CCC AAG ACC CTG ATC TAT CGT GCA AAC AGA TTG CTA GAT GGG      731
Lys Ser Pro Lys Thr Leu Ile Tyr Arg Ala Asn Arg Leu Leu Asp Gly
         45                  50                  55

GTC CCA TCA AGG TTC AGT GGC AGT GGA TCT GGG CAA GAT TAT TCT CTC      779
Val Pro Ser Arg Phe Ser Gly Ser Gly Ser Gly Gln Asp Tyr Ser Leu
             60                  65                  70

ACC ATC AGC AGC CTG GAC TAT GAA GAT ATG GGA ATT TAT TAT TGT CTA      827
Thr Ile Ser Ser Leu Asp Tyr Glu Asp Met Gly Ile Tyr Tyr Cys Leu
 75                  80                  85

CAA TAT GAT GAG TTG TAC ACG TTC GGA GGG GGG ACC AAG CTC GAG ATC      875
Gln Tyr Asp Glu Leu Tyr Thr Phe Gly Gly Gly Thr Lys Leu Glu Ile
 90                  95                 100                 105

AAA CGG TAA TAATGATCAA ACGGTATAAG GATCCAGCTC GAATTC                  920
Lys Arg (2) INFORMATION FOR SEQ ID NO: 4:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO: 4:

Met Lys Tyr Leu Leu Pro Thr Ala Ala Ala Gly Leu Leu Leu Leu Ala
-22      -20                 -15                 -10

Ala Gln Pro Ala Met Ala Gln Val Gln Leu Gln Gln Ser Gly Pro Glu
     -5              1               5                   10

Leu Val Lys Pro Gly Ala Ser Val Lys Met Ser Cys Lys Ala Ser Gly
                 15              20                  25

Tyr Thr Phe Thr Ser Tyr Val Met His Trp Val Lys Gln Lys Pro Gly
                 30              35                  40

Gln Gly Leu Glu Trp Ile Gly Tyr Ile Tyr Pro Tyr Asn Asp Gly Thr
             45              50                  55

Lys Tyr Asn Glu Lys Phe Lys Gly Lys Ala Thr Leu Thr Ser Asp Lys
 60              65                  70

Ser Ser Ser Thr Ala Tyr Met Glu Leu Ser Ser Leu Thr Ser Glu Asp
 75              80                  85                  90

Ser Ala Val Tyr Tyr Cys Ser Arg Arg Phe Asp Tyr Trp Gly Gln Gly
                 95                 100                 105

Thr Thr Val Thr Val Ser Ser
             110

(2) INFORMATION FOR SEQ ID NO: 5:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO: 5:

Met Lys Tyr Leu Leu Pro Thr Ala Ala Ala Gly Leu Leu Leu Leu Ala
-22      -20                 -15                 -10
```

```
Ala Gln Pro Ala Met Ala Asp Ile Glu Leu Thr Gln Ser Pro Ser Ser
    -5            1               5                    10

Met Tyr Ala Ser Leu Gly Glu Arg Ile Thr Ile Thr Cys Lys Ala Ser
             15                  20                  25

Gln Asp Ile Asn Thr Tyr Leu Thr Trp Phe Gln Gln Lys Pro Gly Lys
             30                  35                  40

Ser Pro Lys Thr Leu Ile Tyr Arg Ala Asn Arg Leu Leu Asp Gly Val
         45                  50                  55

Pro Ser Arg Phe Ser Gly Ser Gly Ser Gly Gln Asp Tyr Ser Leu Thr
         60                  65                  70

Ile Ser Ser Leu Asp Tyr Glu Asp Met Gly Ile Tyr Tyr Cys Leu Gln
 75              80                  85                  90

Tyr Asp Glu Leu Tyr Thr Phe Gly Gly Gly Thr Lys Leu Glu Ile Lys
             95                 100                 105

Arg
```

(2) INFORMATION FOR SEQ ID NO: 6:

(i) SEQUENCE CHARACTERISTICS:
        (A) LENGTH: 999 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "cDNA domains with synthetic
            linker(s)"

(vii) IMMEDIATE SOURCE:
        (B) CLONE: HindIII-EcoRI insert of Fv.4715-myc (ix) FEATURE:
        (A) NAME/KEY: CDS
        (B) LOCATION:40..468
        (D) OTHER INFORMATION:/product= "pelB-VH4715"

(ix) FEATURE:
        (A) NAME/KEY: sig_peptide
        (B) LOCATION:40..105
        (D) OTHER INFORMATION:/product= "pectate lyase"

(ix) FEATURE:
        (A) NAME/KEY: mat_peptide
        (B) LOCATION:106..465
        (D) OTHER INFORMATION:/product= "VH4715"

(ix) FEATURE:
        (A) NAME/KEY: CDS
        (B) LOCATION:520..963
        (D) OTHER INFORMATION:/product= "pelB-VL4715-myc"

(ix) FEATURE:
        (A) NAME/KEY: sig_peptide
        (B) LOCATION:520..585
        (D) OTHER INFORMATION:/product= "pectate lyase"

(ix) FEATURE:
        (A) NAME/KEY: mat_peptide
        (B) LOCATION:586..927
        (D) OTHER INFORMATION:/product= "VL4715"

(ix) FEATURE:
        (A) NAME/KEY: misc RNA
        (B) LOCATION:928..960
        (D) OTHER INFORMATION:/product= "myc-tag"

(xi) SEQUENCE DESCRIPTION: SEQ ID NO: 6:

```
AAGCTTGCAT GCAAATTCTA TTTCAAGGAG ACAGTCATA ATG AAA TAC CTA TTG         54
                                          Met Lys Tyr Leu Leu
                                          -22         -20
```

```
CCT ACG GCA GCC GCT GGA TTG TTA TTA CTC GCT GCC CAA CCA GCG ATG        102
Pro Thr Ala Ala Ala Gly Leu Leu Leu Leu Ala Ala Gln Pro Ala Met
        -15                 -10                 -5

GCC CAG GTG CAG CTG CAG GAG TCA GGG GGA GAC TTA GTG AAG CCT GGA        150
Ala Gln Val Gln Leu Gln Glu Ser Gly Gly Asp Leu Val Lys Pro Gly
    1               5                   10                  15

GGG TCC CTG ACA CTC TCC TGT GCA ACC TCT GGA TTC ACT TTC AGT AGT        198
Gly Ser Leu Thr Leu Ser Cys Ala Thr Ser Gly Phe Thr Phe Ser Ser
                20                  25                  30

TAT GCC TTT TCT TGG GTC CGC CAG ACC TCA GAC AAG AGT CTG GAG TGG        246
Tyr Ala Phe Ser Trp Val Arg Gln Thr Ser Asp Lys Ser Leu Glu Trp
            35                  40                  45

GTC GCA ACC ATC AGT AGT ACT GAT ACT TAT ACC TAT TAT TCA GAC AAT        294
Val Ala Thr Ile Ser Ser Thr Asp Thr Tyr Thr Tyr Tyr Ser Asp Asn
        50                  55                  60

GTG AAG GGG CGC TTC ACC ATC TCC AGA GAC AAT GGC AAG AAC ACC CTG        342
Val Lys Gly Arg Phe Thr Ile Ser Arg Asp Asn Gly Lys Asn Thr Leu
    65                  70                  75

TAC CTG CAA ATG AGC AGT CTG AAG TCT GAG GAC ACA GCC GTG TAT TAC        390
Tyr Leu Gln Met Ser Ser Leu Lys Ser Glu Asp Thr Ala Val Tyr Tyr
80                  85                  90                  95

TGT GCA AGA CAT GGG TAC TAT GGT AAA GGC TAT TTT GAC TAC TGG GGC        438
Cys Ala Arg His Gly Tyr Tyr Gly Lys Gly Tyr Phe Asp Tyr Trp Gly
                100                 105                 110

CAA GGG ACC ACG GTC ACC GTC TCC TCA TAA TAAGAGCTAT GGGAGCTTGC          488
Gln Gly Thr Thr Val Thr Val Ser Ser
            115                 120

ATGCAAATTC TATTTCAAGG AGACAGTCAT A ATG AAA TAC CTA TTG CCT ACG         540
                                  Met Lys Tyr Leu Leu Pro Thr
                                  -22         -20

GCA GCC GCT GGA TTG TTA TTA CTC GCT GCC CAA CCA GCG ATG GCC GAC        588
Ala Ala Ala Gly Leu Leu Leu Leu Ala Ala Gln Pro Ala Met Ala Asp
-15                 -10                 -5                  1

ATC GAG CTC ACT CAG TCT CCA TTC TCC CTG ACT GTG ACA GCA GGA GAG        636
Ile Glu Leu Thr Gln Ser Pro Phe Ser Leu Thr Val Thr Ala Gly Glu
        5                   10                  15

AAG GTC ACT ATG AAT TGC AAG TCC GGT CAG AGT CTG TTA AAC AGT GTA        684
Lys Val Thr Met Asn Cys Lys Ser Gly Gln Ser Leu Leu Asn Ser Val
            20                  25                  30

AAT CAG AGG AAC TAC TTG ACC TGG TAC CAG CAG AAG CCA GGG CAG CCT        732
Asn Gln Arg Asn Tyr Leu Thr Trp Tyr Gln Gln Lys Pro Gly Gln Pro
        35                  40                  45

CCT AAA CTG TTG ATC TAC TGG GCA TCC ACT AGG GAA TCT GGA GTC CCT        780
Pro Lys Leu Leu Ile Tyr Trp Ala Ser Thr Arg Glu Ser Gly Val Pro
50                  55                  60                  65

GAT CGC TTC ACA GCC AGT GGA TCT GGA ACA GAT TTC ACT CTC ACC ATC        828
Asp Arg Phe Thr Ala Ser Gly Ser Gly Thr Asp Phe Thr Leu Thr Ile
                70                  75                  80

AGC AGT GTG CAG GCT GAA GAC CTG GCA GTT TAT TAC TGT CAG AAT GAT        876
Ser Ser Val Gln Ala Glu Asp Leu Ala Val Tyr Tyr Cys Gln Asn Asp
            85                  90                  95

TAT ACT TAT CCG TTC ACG TTC GGA GGG GGG ACC AAG CTC GAG ATC AAA        924
Tyr Thr Tyr Pro Phe Thr Phe Gly Gly Gly Thr Lys Leu Glu Ile Lys
        100                 105                 110

CGG GAA CAA AAA CTC ATC TCA GAA GAG GAT CTG AAT TAA TAAGATCAAA         973
Arg Glu Gln Lys Leu Ile Ser Glu Glu Asp Leu Asn
115                 120                 125

CGGTAATAAG GATCCAGCTC GAATTC                                           999
```

(2) INFORMATION FOR SEQ ID NO: 7:

(i) SEQUENCE CHARACTERISTICS:
        (A) LENGTH: 142 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Lys Tyr Leu Leu Pro Thr Ala Ala Ala Gly Leu Leu Leu Ala
-22     -20             -15             -10

Ala Gln Pro Ala Met Ala Gln Val Gln Leu Gln Glu Ser Gly Gly Asp
    -5          1                   5                       10

Leu Val Lys Pro Gly Gly Ser Leu Thr Leu Ser Cys Ala Thr Ser Gly
                15                  20                  25

Phe Thr Phe Ser Ser Tyr Ala Phe Ser Trp Val Arg Gln Thr Ser Asp
                30                  35                  40

Lys Ser Leu Glu Trp Val Ala Thr Ile Ser Ser Thr Asp Thr Tyr Thr
                45                  50                  55

Tyr Tyr Ser Asp Asn Val Lys Gly Arg Phe Thr Ile Ser Arg Asp Asn
                60              65                  70

Gly Lys Asn Thr Leu Tyr Leu Gln Met Ser Ser Leu Lys Ser Glu Asp
75              80                  85                  90

Thr Ala Val Tyr Tyr Cys Ala Arg His Gly Tyr Tyr Gly Lys Gly Tyr
                    95              100                 105

Phe Asp Tyr Trp Gly Gln Gly Thr Thr Val Thr Val Ser Ser
                110                 115             120
```

(2) INFORMATION FOR SEQ ID NO: 8:

(i) SEQUENCE CHARACTERISTICS:
        (A) LENGTH: 147 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Lys Tyr Leu Leu Pro Thr Ala Ala Ala Gly Leu Leu Leu Ala
-22     -20             -15             -10

Ala Gln Pro Ala Met Ala Asp Ile Glu Leu Thr Gln Ser Pro Phe Ser
    -5          1                   5                       10

Leu Thr Val Thr Ala Gly Glu Lys Val Thr Met Asn Cys Lys Ser Gly
                15                  20                  25

Gln Ser Leu Leu Asn Ser Val Asn Gln Arg Asn Tyr Leu Thr Trp Tyr
                30                  35                  40

Gln Gln Lys Pro Gly Gln Pro Pro Lys Leu Leu Ile Tyr Trp Ala Ser
                45                  50                  55

Thr Arg Glu Ser Gly Val Pro Asp Arg Phe Thr Ala Ser Gly Ser Gly
60              65                  70

Thr Asp Phe Thr Leu Thr Ile Ser Ser Val Gln Ala Glu Asp Leu Ala
75              80                  85                  90

Val Tyr Tyr Cys Gln Asn Asp Tyr Thr Tyr Pro Phe Thr Phe Gly Gly
                95              100                 105

Gly Thr Lys Leu Glu Ile Lys Arg Glu Gln Lys Leu Ile Ser Glu Glu
                110                 115                 120

Asp Leu Asn
    125
```

(2) INFORMATION FOR SEQ ID NO: 9:

(i) SEQUENCE CHARACTERISTICS:
        (A) LENGTH: 924 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "cDNA domains with synthetic
            linker(s)"

(vii) IMMEDIATE SOURCE:
        (B) CLONE: HindIII-EcoRI insert of scFv.4715-myc (ix) FEATURE:
        (A) NAME/KEY: sig_peptide
        (B) LOCATION:40..105
        (D) OTHER INFORMATION:/product= "pectate lyase"

(ix) FEATURE:
        (A) NAME/KEY: mat_peptide
        (B) LOCATION:106..465
        (D) OTHER INFORMATION:/product= "VH4715"

(ix) FEATURE:
        (A) NAME/KEY: misc_RNA
        (B) LOCATION:466..510
        (D) OTHER INFORMATION:/product= "(Gly4Ser)3-linker"

(ix) FEATURE:
        (A) NAME/KEY: mat_peptide
        (B) LOCATION:511..852
        (D) OTHER INFORMATION:/product= "VL4715"

(ix) FEATURE:
        (A) NAME/KEY: misc_RNA
        (B) LOCATION:853..885
        (D) OTHER INFORMATION:/product= "myc-tag"

(ix) FEATURE:
        (A) NAME/KEY: CDS
        (B) LOCATION:40..888
        (D) OTHER INFORMATION:/product= "pelB-VH4715-(Gly4Ser)3-
           VL4715-myc"

(xi) SEQUENCE DESCRIPTION: SEQ ID NO: 9:

```
AAGCTTGCAT GCAAATTCTA TTTCAAGGAG ACAGTCATA ATG AAA TAC CTA TTG       54
                                            Met Lys Tyr Leu Leu
                                            -22         -20

CCT ACG GCA GCC GCT GGA TTG TTA TTA CTC GCT GCC CAA CCA GCG ATG     102
Pro Thr Ala Ala Ala Gly Leu Leu Leu Leu Ala Ala Gln Pro Ala Met
        -15                 -10                 -5

GCC CAG GTG CAG CTG CAG GAG TCA GGG GGA GAC TTA GTG AAG CCT GGA     150
Ala Gln Val Gln Leu Gln Glu Ser Gly Gly Asp Leu Val Lys Pro Gly
 1           5                  10                  15

GGG TCC CTG ACA CTC TCC TGT GCA ACC TCT GGA TTC ACT TTC AGT AGT     198
Gly Ser Leu Thr Leu Ser Cys Ala Thr Ser Gly Phe Thr Phe Ser Ser
            20                  25                  30

TAT GCC TTT TCT TGG GTC CGC CAG ACC TCA GAC AAG AGT CTG GAG TGG     246
Tyr Ala Phe Ser Trp Val Arg Gln Thr Ser Asp Lys Ser Leu Glu Trp
            35                  40                  45

GTC GCA ACC ATC AGT AGT ACT GAT ACT TAT ACC TAT TAT TCA GAC AAT     294
Val Ala Thr Ile Ser Ser Thr Asp Thr Tyr Thr Tyr Tyr Ser Asp Asn
            50                  55                  60

GTG AAG GGG CGC TTC ACC ATC TCC AGA GAC AAT GGC AAG AAC ACC CTG     342
Val Lys Gly Arg Phe Thr Ile Ser Arg Asp Asn Gly Lys Asn Thr Leu
 65                  70                  75

TAC CTG CAA ATG AGC AGT CTG AAG TCT GAG GAC ACA GCC GTG TAT TAC     390
Tyr Leu Gln Met Ser Ser Leu Lys Ser Glu Asp Thr Ala Val Tyr Tyr
 80                  85                  90                  95
```

-continued

```
TGT GCA AGA CAT GGG TAC TAT GGT AAA GGC TAT TTT GAC TAC TGG GGC        438
Cys Ala Arg His Gly Tyr Tyr Gly Lys Gly Tyr Phe Asp Tyr Trp Gly
            100                 105                 110

CAA GGG ACC ACG GTC ACC GTC TCC TCA GGT GGA GGC GGT TCA GGC GGA        486
Gln Gly Thr Thr Val Thr Val Ser Ser Gly Gly Gly Gly Ser Gly Gly
        115                 120                 125

GGT GGC TCT GGC GGT GGC GGA TCG GAC ATC GAG CTC ACT CAG TCT CCA        534
Gly Gly Ser Gly Gly Gly Gly Ser Asp Ile Glu Leu Thr Gln Ser Pro
        130                 135                 140

TTC TCC CTG ACT GTG ACA GCA GGA GAG AAG GTC ACT ATG AAT TGC AAG        582
Phe Ser Leu Thr Val Thr Ala Gly Glu Lys Val Thr Met Asn Cys Lys
        145                 150                 155

TCC GGT CAG AGT CTG TTA AAC AGT GTA AAT CAG AGG AAC TAC TTG ACC        630
Ser Gly Gln Ser Leu Leu Asn Ser Val Asn Gln Arg Asn Tyr Leu Thr
160                 165                 170                 175

TGG TAC CAG CAG AAG CCA GGG CAG CCT CCT AAA CTG TTG ATC TAC TGG        678
Trp Tyr Gln Gln Lys Pro Gly Gln Pro Pro Lys Leu Leu Ile Tyr Trp
                180                 185                 190

GCA TCC ACT AGG GAA TCT GGA GTC CCT GAT CGC TTC ACA GCC AGT GGA        726
Ala Ser Thr Arg Glu Ser Gly Val Pro Asp Arg Phe Thr Ala Ser Gly
            195                 200                 205

TCT GGA ACA GAT TTC ACT CTC ACC ATC AGC AGT GTG CAG GCT GAA GAC        774
Ser Gly Thr Asp Phe Thr Leu Thr Ile Ser Ser Val Gln Ala Glu Asp
        210                 215                 220

CTG GCA GTT TAT TAC TGT CAG AAT GAT TAT ACT TAT CCG TTC ACG TTC        822
Leu Ala Val Tyr Tyr Cys Gln Asn Asp Tyr Thr Tyr Pro Phe Thr Phe
225                 230                 235

GGA GGG GGG ACC AAG CTC GAG ATC AAA CGG GAA CAA AAA CTC ATC TCA        870
Gly Gly Gly Thr Lys Leu Glu Ile Lys Arg Glu Gln Lys Leu Ile Ser
240                 245                 250                 255

GAA GAG GAT CTG AAT TAA TAAGATCAAA CGGTAATAAG GATCCAGCTC GAATTC        924
Glu Glu Asp Leu Asn
                260
```

(2) INFORMATION FOR SEQ ID NO: 10:

(i) SEQUENCE CHARACTERISTICS:
       (A) LENGTH: 282 amino acids
       (B) TYPE: amino acid
       (D) TOPOLOGY: linear (ii) MOLECULE TYPE: protein (xi) SEQUENCE DESCRIPTION: SEQ ID NO: 10:

```
Met Lys Tyr Leu Leu Pro Thr Ala Ala Ala Gly Leu Leu Leu Leu Ala
-22         -20                 -15                 -10

Ala Gln Pro Ala Met Ala Gln Val Gln Leu Gln Glu Ser Gly Gly Asp
    -5                  1                   5                   10

Leu Val Lys Pro Gly Gly Ser Leu Thr Leu Ser Cys Ala Thr Ser Gly
                15                  20                  25

Phe Thr Phe Ser Ser Tyr Ala Phe Ser Trp Val Arg Gln Thr Ser Asp
                30                  35                  40

Lys Ser Leu Glu Trp Val Ala Thr Ile Ser Ser Thr Asp Thr Tyr Thr
                45                  50                  55

Tyr Tyr Ser Asp Asn Val Lys Gly Arg Phe Thr Ile Ser Arg Asp Asn
            60                  65                  70

Gly Lys Asn Thr Leu Tyr Leu Gln Met Ser Ser Leu Lys Ser Glu Asp
75                  80                  85                  90

Thr Ala Val Tyr Tyr Cys Ala Arg His Gly Tyr Tyr Gly Lys Gly Tyr
                    95                  100                 105
```

```
Phe Asp Tyr Trp Gly Gln Gly Thr Thr Val Thr Val Ser Ser Gly Gly
            110                 115                 120

Gly Gly Ser Gly Gly Gly Ser Gly Gly Gly Ser Asp Ile Glu
            125                 130                 135

Leu Thr Gln Ser Pro Phe Ser Leu Thr Val Thr Ala Gly Glu Lys Val
            140                 145                 150

Thr Met Asn Cys Lys Ser Gly Gln Ser Leu Leu Asn Ser Val Asn Gln
155                 160                 165                 170

Arg Asn Tyr Leu Thr Trp Tyr Gln Gln Lys Pro Gly Gln Pro Pro Lys
                175                 180                 185

Leu Leu Ile Tyr Trp Ala Ser Thr Arg Glu Ser Gly Val Pro Asp Arg
                190                 195                 200

Phe Thr Ala Ser Gly Ser Gly Thr Asp Phe Thr Leu Thr Ile Ser Ser
            205                 210                 215

Val Gln Ala Glu Asp Leu Ala Val Tyr Tyr Cys Gln Asn Asp Tyr Thr
            220                 225                 230

Tyr Pro Phe Thr Phe Gly Gly Gly Thr Lys Leu Glu Ile Lys Arg Glu
235                 240                 245                 250

Gln Lys Leu Ile Ser Glu Glu Asp Leu Asn
                255                 260

(2) INFORMATION FOR SEQ ID NO: 11:

(i) SEQUENCE CHARACTERISTICS:
        (A) LENGTH: 1706 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "cDNA domains with synthetic
            linker(s)"

(vii) IMMEDIATE SOURCE:
        (B) CLONE: HindIII-EcoRI insert of pGOSA.E (ix) FEATURE:
        (A) NAME/KEY: CDS
        (B) LOCATION:40..864
        (D) OTHER INFORMATION:/product= "pelB-VH4715-LiA-VH3418"

(ix) FEATURE:
        (A) NAME/KEY: sig_peptide
        (B) LOCATION:40..105
        (D) OTHER INFORMATION:/product= "pectate lyase"

(ix) FEATURE:
        (A) NAME/KEY: mat_peptide
        (B) LOCATION:106..465
        (D) OTHER INFORMATION:/product= "VH4715"

(ix) FEATURE:
        (A) NAME/KEY: misc_RNA
        (B) LOCATION:466..522
        (D) OTHER INFORMATION:/product= "linkerA (Gly4Ser)
            3AlaGlySerAla"

(ix) FEATURE:
        (A) NAME/KEY: mat_peptide
        (B) LOCATION:523..861
        (D) OTHER INFORMATION:/product= "VH3418"

(ix) FEATURE:
        (A) NAME/KEY: CDS
        (B) LOCATION:913..1689
        (D) OTHER INFORMATION:/product= "pelB-VL3418-LiV-VL4715"

(ix) FEATURE:
        (A) NAME/KEY: sig_peptide
```

(B) LOCATION:913..978
(D) OTHER INFORMATION:/product= "pectate lyase"

(ix) FEATURE:
(A) NAME/KEY: mat_peptide
(B) LOCATION:979..1299
(D) OTHER INFORMATION:/product= "VL3418"

(ix) FEATURE:
(A) NAME/KEY: misc_RNA
(B) LOCATION:1300..1344
(D) OTHER INFORMATION:/product= "linker V (Gly4Ser)2Gly4Val"

(ix) FEATURE:
(A) NAME/KEY: mat_peptide
(B) LOCATION:1345..1686
(D) OTHER INFORMATION:/product= "VL4715"

(xi) SEQUENCE DESCRIPTION: SEQ ID NO: 11:

```
AAGCTTGCAT GGAAATTCTA TTTCAAGGAG ACAGTCATA ATG AAA TAC CTA TTG                  54
                                             Met Lys Tyr Leu Leu
                                             -22         -20

CCT ACG GCA GCC GCT GGA TTG TTA TTA CTC GCT GCC CAA CCA GCG ATG                102
Pro Thr Ala Ala Ala Gly Leu Leu Leu Leu Ala Ala Gln Pro Ala Met
        -15                 -10                 -5

GCC CAG GTG CAG CTG CAG GAG TCA GGG GGA GAC TTA GTG AAG CCT GGA                150
Ala Gln Val Gln Leu Gln Glu Ser Gly Gly Asp Leu Val Lys Pro Gly
 1               5                  10                  15

GGG TCC CTG ACA CTC TCC TGT GCA ACC TCT GGA TTC ACT TTC AGT AGT                198
Gly Ser Leu Thr Leu Ser Cys Ala Thr Ser Gly Phe Thr Phe Ser Ser
             20                  25                  30

TAT GCC TTT TCT TGG GTC CGC CAG ACC TCA GAC AAG AGT CTG GAG TGG                246
Tyr Ala Phe Ser Trp Val Arg Gln Thr Ser Asp Lys Ser Leu Glu Trp
         35                  40                  45

GTC GCA ACC ATC AGT AGT ACT GAT ACT TAT ACC TAT TAT TCA GAC AAT                294
Val Ala Thr Ile Ser Ser Thr Asp Thr Tyr Thr Tyr Tyr Ser Asp Asn
     50                  55                  60

GTG AAG GGG CGC TTC ACC ATC TCC AGA GAC AAT GGC AAG AAC ACC CTG                342
Val Lys Gly Arg Phe Thr Ile Ser Arg Asp Asn Gly Lys Asn Thr Leu
 65                  70                  75

TAC CTG CAA ATG AGC AGT CTG AAG TCT GAG GAC ACA GCC GTG TAT TAC                390
Tyr Leu Gln Met Ser Ser Leu Lys Ser Glu Asp Thr Ala Val Tyr Tyr
 80              85                  90                  95

TGT GCA AGA CAT GGG TAC TAT GGT AAA GGC TAT TTT GAC TAC TGG GGC                438
Cys Ala Arg His Gly Tyr Tyr Gly Lys Gly Tyr Phe Asp Tyr Trp Gly
             100                 105                 110

CAA GGG ACC ACG GTC ACC GTC TCC TCA GGT GGA GGC GGT TCA GGC GGA                486
Gln Gly Thr Thr Val Thr Val Ser Ser Gly Gly Gly Gly Ser Gly Gly
         115                 120                 125

GGT GGC TCT GGC GGT GGC GGA TCG GCC GGT TCG GCC CAG GTC CAG CTG                534
Gly Gly Ser Gly Gly Gly Gly Ser Ala Gly Ser Ala Gln Val Gln Leu
     130                 135                 140

CAA CAG TCA GGA CCT GAG CTG GTA AAG CCT GGG GCT TCA GTG AAG ATG                582
Gln Gln Ser Gly Pro Glu Leu Val Lys Pro Gly Ala Ser Val Lys Met
 145                 150                 155

TCC TGC AAG GCT TCT GGA TAC ACA TTC ACT AGC TAT GTT ATG CAC TGG                630
Ser Cys Lys Ala Ser Gly Tyr Thr Phe Thr Ser Tyr Val Met His Trp
160                 165                 170                 175

GTG AAA CAG AAG CCT GGG CAG GGC CTT GAG TGG ATT GGA TAT ATT TAT                678
Val Lys Gln Lys Pro Gly Gln Gly Leu Glu Trp Ile Gly Tyr Ile Tyr
                 180                 185                 190

CCT TAC AAT GAT GGT ACT AAG TAC AAT GAG AAG TTC AAA GGC AAG GCC                726
Pro Tyr Asn Asp Gly Thr Lys Tyr Asn Glu Lys Phe Lys Gly Lys Ala
             195                 200                 205
```

| | | |
|---|---|---|
| ACA CTG ACT TCA GAC AAA TCC TCC AGC ACA GCC TAC ATG GAG CTC AGC | | 774 |
| Thr Leu Thr Ser Asp Lys Ser Ser Ser Thr Ala Tyr Met Glu Leu Ser | | |
| 210 215 220 | | |
| AGC CTG ACC TCT GAG GAC TCT GCG GTC TAT TAC TGT TCA AGA CGC TTT | | 822 |
| Ser Leu Thr Ser Glu Asp Ser Ala Val Tyr Tyr Cys Ser Arg Arg Phe | | |
| 225 230 235 | | |
| GAC TAC TGG GGC CAA GGG ACC ACC GTC ACC GTC TCC TCA TAA | | 864 |
| Asp Tyr Trp Gly Gln Gly Thr Thr Val Thr Val Ser Ser | | |
| 240 245 250 | | |
| TAAGCTAGCG GAGCTGCATG CAAATTCTAT TTCAAGGAGA CAGTCATA ATG AAA TAC | | 921 |
| Met Lys Tyr | | |
| -22 -20 | | |
| CTA TTG CCT ACG GCA GCC GCT GGA TTG TTA TTA CTC GCT GCC CAA CCA | | 969 |
| Leu Leu Pro Thr Ala Ala Ala Gly Leu Leu Leu Leu Ala Ala Gln Pro | | |
| -15 -10 -5 | | |
| GCG ATG GCC GAC ATC GAG CTC ACC CAG TCT CCA TCT TCC ATG TAT GCA | | 1017 |
| Ala Met Ala Asp Ile Glu Leu Thr Gln Ser Pro Ser Ser Met Tyr Ala | | |
| 1 5 10 | | |
| TCT CTA GGA GAG AGA ATC ACT ATC ACT TGC AAG GCG AGT CAG GAC ATT | | 1065 |
| Ser Leu Gly Glu Arg Ile Thr Ile Thr Cys Lys Ala Ser Gln Asp Ile | | |
| 15 20 25 | | |
| AAT ACC TAT TTA ACC TGG TTC CAG CAG AAA CCA GGG AAA TCT CCC AAG | | 1113 |
| Asn Thr Tyr Leu Thr Trp Phe Gln Gln Lys Pro Gly Lys Ser Pro Lys | | |
| 30 35 40 45 | | |
| ACC CTG ATC TAT CGT GCA AAC AGA TTG CTA GAT GGG GTC CCA TCA AGG | | 1161 |
| Thr Leu Ile Tyr Arg Ala Asn Arg Leu Leu Asp Gly Val Pro Ser Arg | | |
| 50 55 60 | | |
| TTC AGT GGC AGT GGA TCT GGG CAA GAT TAT TCT CTC ACC ATC AGC AGC | | 1209 |
| Phe Ser Gly Ser Gly Ser Gly Gln Asp Tyr Ser Leu Thr Ile Ser Ser | | |
| 65 70 75 | | |
| CTG GAC TAT GAA GAT ATG GGA ATT TAT TAT TGT CTA CAA TAT GAT GAG | | 1257 |
| Leu Asp Tyr Glu Asp Met Gly Ile Tyr Tyr Cys Leu Gln Tyr Asp Glu | | |
| 80 85 90 | | |
| TTG TAC ACG TTC GGA GGG GGG ACC AAG CTC GAG ATC AAA CGG GGT GGA | | 1305 |
| Leu Tyr Thr Phe Gly Gly Gly Thr Lys Leu Glu Ile Lys Arg Gly Gly | | |
| 95 100 105 | | |
| GGC GGT TCA GGC GGA GGT GGC TCT GGC GGT GGC GGA TCG GAC ATC GAA | | 1353 |
| Gly Gly Ser Gly Gly Gly Gly Ser Gly Gly Gly Gly Val Asp Ile Glu | | |
| 110 115 120 125 | | |
| CTC ACT CAG TCT CCA TTC TCC CTG ACT GTG ACA GCA GGA GAG AAG GTC | | 1401 |
| Leu Thr Gln Ser Pro Phe Ser Leu Thr Val Thr Ala Gly Glu Lys Val | | |
| 130 135 140 | | |
| ACT ATG AAT TGC AAG TCC GGT CAG AGT CTG TTA AAC AGT GTA AAT CAG | | 1449 |
| Thr Met Asn Cys Lys Ser Gly Gln Ser Leu Leu Asn Ser Val Asn Gln | | |
| 145 150 155 | | |
| AGG AAC TAC TTG ACC TGG TAC CAG CAG AAG CCA GGG CAG CCT CCT AAA | | 1497 |
| Arg Asn Tyr Leu Thr Trp Tyr Gln Gln Lys Pro Gly Gln Pro Pro Lys | | |
| 160 165 170 | | |
| CTG TTG ATC TAC TGG GCA TCC ACT AGG GAA TCT GGA GTC CCT GAT CGC | | 1545 |
| Leu Leu Ile Tyr Trp Ala Ser Thr Arg Glu Ser Gly Val Pro Asp Arg | | |
| 175 180 185 | | |
| TTC ACA GCC AGT GGA TCT GGA ACA GAT TTC ACT CTC ACC ATC AGC AGT | | 1593 |
| Phe Thr Ala Ser Gly Ser Gly Thr Asp Phe Thr Leu Thr Ile Ser Ser | | |
| 190 195 200 205 | | |
| GTG CAG GCT GAA GAC CTG GCA GTT TAT TAC TGT CAG AAT GAT TAT ACT | | 1641 |
| Val Gln Ala Glu Asp Leu Ala Val Tyr Tyr Cys Gln Asn Asp Tyr Thr | | |
| 210 215 220 | | |
| TAT CCG TTC ACG TTC GGA GGG GGG ACC AAG CTC GAA ATC AAA CGG TAA | | 1689 |
| Tyr Pro Phe Thr Phe Gly Gly Gly Thr Lys Leu Glu Ile Lys Arg | | |
| 225 230 235 | | |

TAAGCGGCCG CGAATTC                                                         1706

(2) INFORMATION FOR SEQ ID NO: 12:

(i) SEQUENCE CHARACTERISTICS:
        (A) LENGTH: 274 amino acids
        (B) TYPE: amino acid
        (D) TOPOLOGY: linear (ii) MOLECULE TYPE: protein (xi) SEQUENCE DESCRIPTION: SEQ ID NO: 12:

Met Lys Tyr Leu Leu Pro Thr Ala Ala Ala Gly Leu Leu Leu Ala
-22      -20              -15              -10

Ala Gln Pro Ala Met Ala Gln Val Gln Leu Gln Glu Ser Gly Gly Asp
 -5              1               5                       10

Leu Val Lys Pro Gly Gly Ser Leu Thr Leu Ser Cys Ala Thr Ser Gly
                 15              20                  25

Phe Thr Phe Ser Ser Tyr Ala Phe Ser Trp Val Arg Gln Thr Ser Asp
             30              35                  40

Lys Ser Leu Glu Trp Val Ala Thr Ile Ser Ser Thr Asp Thr Tyr Thr
         45              50              55

Tyr Tyr Ser Asp Asn Val Lys Gly Arg Phe Thr Ile Ser Arg Asp Asn
 60              65              70

Gly Lys Asn Thr Leu Tyr Leu Gln Met Ser Ser Leu Lys Ser Glu Asp
75              80              85                      90

Thr Ala Val Tyr Tyr Cys Ala Arg His Gly Tyr Gly Lys Gly Tyr
             95              100             105

Phe Asp Tyr Trp Gly Gln Gly Thr Thr Val Thr Val Ser Ser Gly Gly
            110             115                 120

Gly Gly Ser Gly Gly Gly Gly Ser Gly Gly Gly Gly Ser Ala Gly Ser
        125             130             135

Ala Gln Val Gln Leu Gln Gln Ser Gly Pro Glu Leu Val Lys Pro Gly
    140             145             150

Ala Ser Val Lys Met Ser Cys Lys Ala Ser Gly Tyr Thr Phe Thr Ser
155             160             165             170

Tyr Val Met His Trp Val Lys Gln Lys Pro Gly Gln Gly Leu Glu Trp
            175             180             185

Ile Gly Tyr Ile Tyr Pro Tyr Asn Asp Gly Thr Lys Tyr Asn Glu Lys
            190             195             200

Phe Lys Gly Lys Ala Thr Leu Thr Ser Asp Lys Ser Ser Ser Thr Ala
        205             210             215

Tyr Met Glu Leu Ser Ser Leu Thr Ser Glu Asp Ser Ala Val Tyr Tyr
220             225             230

Cys Ser Arg Arg Phe Asp Tyr Trp Gly Gln Gly Thr Thr Val Thr Val
235             240             245             250

Ser Ser (2) INFORMATION FOR SEQ ID NO: 13:

(i) SEQUENCE CHARACTERISTICS:
        (A) LENGTH: 258 amino acids
        (B) TYPE: amino acid
        (D) TOPOLOGY: linear (ii) MOLECULE TYPE: protein (xi) SEQUENCE DESCRIPTION: SEQ ID NO: 13:

Met Lys Tyr Leu Leu Pro Thr Ala Ala Ala Gly Leu Leu Leu Ala

```
-22         -20             -15                 -10
```

Ala Gln Pro Ala Met Ala Asp Ile Glu Leu Thr Gln Ser Pro Ser Ser
        -5              1               5                  10

Met Tyr Ala Ser Leu Gly Glu Arg Ile Thr Ile Thr Cys Lys Ala Ser
                15                  20                  25

Gln Asp Ile Asn Thr Tyr Leu Thr Trp Phe Gln Gln Lys Pro Gly Lys
                30                  35              40

Ser Pro Lys Thr Leu Ile Tyr Arg Ala Asn Arg Leu Leu Asp Gly Val
            45                  50              55

Pro Ser Arg Phe Ser Gly Ser Gly Ser Gly Gln Asp Tyr Ser Leu Thr
        60                  65              70

Ile Ser Ser Leu Asp Tyr Glu Asp Met Gly Ile Tyr Tyr Cys Leu Gln
75                  80              85                  90

Tyr Asp Glu Leu Tyr Thr Phe Gly Gly Gly Thr Lys Leu Glu Ile Lys
                95                  100                 105

Arg Gly Gly Gly Gly Ser Gly Gly Gly Ser Gly Gly Gly Gly Gly Val
                110                 115                 120

Asp Ile Glu Leu Thr Gln Ser Pro Phe Ser Leu Thr Val Thr Ala Gly
                125                 130                 135

Glu Lys Val Thr Met Asn Cys Lys Ser Gly Gln Ser Leu Leu Asn Ser
    140                 145                 150

Val Asn Gln Arg Asn Tyr Leu Thr Trp Tyr Gln Gln Lys Pro Gly Gln
155                 160                 165                 170

Pro Pro Lys Leu Leu Ile Tyr Trp Ala Ser Thr Arg Glu Ser Gly Val
                175                 180                 185

Pro Asp Arg Phe Thr Ala Ser Gly Ser Gly Thr Asp Phe Thr Leu Thr
                190                 195                 200

Ile Ser Ser Val Gln Ala Glu Asp Leu Ala Val Tyr Tyr Cys Gln Asn
            205                 210                 215

Asp Tyr Thr Tyr Pro Phe Thr Phe Gly Gly Gly Thr Lys Leu Glu Ile
            220                 225                 230

Lys Arg
235

(2) INFORMATION FOR SEQ ID NO: 14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(vii) IMMEDIATE SOURCE:
        (B) CLONE: primer DBL.1

(xi) SEQUENCE DESCRIPTION: SEQ ID NO: 14:

CACCATCTCC AGAGACAATG GCAAG                                     25

(2) INFORMATION FOR SEQ ID NO: 15:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(vii) IMMEDIATE SOURCE:
              (B) CLONE: primer DBL.2

(xi) SEQUENCE DESCRIPTION: SEQ ID NO: 15:

GAGCGCGAGC TCGGCCGAAC CGGCCGATCC GCCACCGCCA GAGCC                              45

(2) INFORMATION FOR SEQ ID NO: 16:

(i) SEQUENCE CHARACTERISTICS:
              (A) LENGTH: 45 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "synthetic DNA"

(vii) IMMEDIATE SOURCE:
              (B) CLONE: primer DBL.3

(xi) SEQUENCE DESCRIPTION: SEQ ID NO: 16:

CAGGATCCGG CCGGTTCGGC CCAGGTCCAG CTGCAACAGT CAGGA                              45

(2) INFORMATION FOR SEQ ID NO: 17:

(i) SEQUENCE CHARACTERISTICS:
              (A) LENGTH: 53 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "synthetic DNA"

(vii) IMMEDIATE SOURCE:
              (B) CLONE: primer DBL.4

(xi) SEQUENCE DESCRIPTION: SEQ ID NO: 17:

CTACATGAAT TCGCTAGCTT ATTATGAGGA GACGGTGACG GTGGTCCCTT GGC                     53

(2) INFORMATION FOR SEQ ID NO: 18:

(i) SEQUENCE CHARACTERISTICS:
              (A) LENGTH: 36 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "synthetic DNA"

(vii) IMMEDIATE SOURCE:
              (B) CLONE: primer DBL.5

(xi) SEQUENCE DESCRIPTION: SEQ ID NO: 18:

TAATAAGCTA GCGGAGCTGC ATGCAAATTC TATTTC                                        36

(2) INFORMATION FOR SEQ ID NO: 19:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "synthetic DNA"

(vii) IMMEDIATE SOURCE:
              (B) CLONE: primer DBL.6

(xi) SEQUENCE DESCRIPTION: SEQ ID NO: 19:

ACCAAGCTCG AGATCAAACG GGG                                                            23

(2) INFORMATION FOR SEQ ID NO: 20:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(vii) IMMEDIATE SOURCE:
        (B) CLONE: primer DBL.7

(xi) SEQUENCE DESCRIPTION: SEQ ID NO: 20:

AATGTCGAAT TCGTCGACTC CGCCACCGCC AGAGCC                                              36

(2) INFORMATION FOR SEQ ID NO: 21:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = synthetic DNA"

(vii) IMMEDIATE SOURCE:
        (B) CLONE: primer DBL.8

(xi) SEQUENCE DESCRIPTION: SEQ ID NO: 21:

ATTGGAGTCG ACATCGAACT CACTCAGTCT CCATTCTCC                                           39

(2) INFORMATION FOR SEQ ID NO: 22:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(vii) IMMEDIATE SOURCE:
        (B) CLONE: primer DBL.9

(xi) SEQUENCE DESCRIPTION: SEQ ID NO: 22:

TGAAGTGAAT TCGCGGCCGC TTATTACCGT TTGATTTCGA GCTTGGTCCC                               50

(2) INFORMATION FOR SEQ ID NO: 23:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(vii) IMMEDIATE SOURCE:
        (B) CLONE: primer DBL.10

(xi) SEQUENCE DESCRIPTION: SEQ ID NO: 23:

CGAATTCGGT CACCGTCTCC TCACAGGTCC AGTTGCAACA G                                        41

(2) INFORMATION FOR SEQ ID NO: 24:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(vii) IMMEDIATE SOURCE:
        (B) CLONE: primer DBL.11

(xi) SEQUENCE DESCRIPTION: SEQ ID NO: 24:

CGAATTCTCG AGATCAAACG GGACATCGAA CTCACTCAGT CTCC        44

(2) INFORMATION FOR SEQ ID NO: 25:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(vii) IMMEDIATE SOURCE:
        (B) CLONE: primer DBL.12

(xi) SEQUENCE DESCRIPTION: SEQ ID NO: 25:

CGAATTCGGT CACCGTCTCC TCACAGGTGC AGTTGCAGGA G        41

(2) INFORMATION FOR SEQ ID NO: 26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(vii) IMMEDIATE SOURCE:
        (B) CLONE: primer PCR.51

(xi) SEQUENCE DESCRIPTION: SEQ ID NO: 26:

AGGTSMAMCT GCAGSAGTCW GG        22

(2) INFORMATION FOR SEQ ID NO: 27:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(vii) IMMEDIATE SOURCE:
        (B) CLONE: primer PCR.89

(xi) SEQUENCE DESCRIPTION: SEQ ID NO: 27:

TGAGGAGACG GTGACCGTGG TCCCTTGGCC CC        32

(2) INFORMATION FOR SEQ ID NO: 28:

(i) SEQUENCE CHARACTERISTICS:

```
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(vii) IMMEDIATE SOURCE:
        (B) CLONE: primer PCR.90

(xi) SEQUENCE DESCRIPTION: SEQ ID NO: 28:

GACATTGAGC TCACCCAGTC TCCA                                              24

(2) INFORMATION FOR SEQ ID NO: 29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(vii) IMMEDIATE SOURCE:
        (B) CLONE: primer PCR.116

(xi) SEQUENCE DESCRIPTION: SEQ ID NO: 29:

GTTAGATCTC GAGCTTGGTC CC                                                22

(2) INFORMATION FOR SEQ ID NO: 30:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 30:

Thr Thr Val Thr Val Ser Ser Gln Val Gln Leu Gln Gln
1               5                  10

(2) INFORMATION FOR SEQ ID NO: 31:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO: 31:

Lys Leu Glu Ile Lys Arg Asp Ile Glu Leu Thr Gln
1               5                  10
```

BIFUNCTIONAL OR BIVALENT ANTIBODY FRAGMENT ANALOGUE

This application is the national phase filing of International application PCT/EP96/03605, filed Aug. 14, 1996, which designated the U.S. and claims priority based on GB 95307332.7, filed in Great Britain on Oct. 16, 1995.

The invention relates to new bispecific or bivalent antibody fragment analogues, a process for preparing such antibody fragment analogues and various uses of such antibody fragment analogues.

BACKGROUND OF THE INVENTION AND PRIOR ART

1. Antibody Structure

Antibody molecules typically are Y-shaped molecules whose basic unit consist of four polypeptides, two identical heavy chains and two identical light chains, which are covalently linked together by disulfide bonds. Each of these chains is folded in discrete domains. The C-terminal regions of both heavy and light chains are conserved in sequence and are called the constant regions, also known as C-domains. The N-terminal regions, also known as V-domains, are variable in sequence and are responsible for the antibody specificity. The antibody specifically recognizes and binds to an antigen mainly through six short complementarity-determining regions located in their V-domains (see FIG. 1).

In this specification abbreviations are used having the following meaning.

C-domain: Constant domain
V-domain: Variable domain
V: Variable domain of the light chain
$V_H$: Variable domain of the heavy chain
Fv: dual chain antibody fragment containing both a $V_H$ and a $V_L$
scFv: single-chain Fv ($V_H$ and $V_L$ genetically linked either directly or via a peptide linker)
CDR: Complementarity-determining region
ELISA: Enzyme Linked Immuno Sorbent Assay
PCR: Polymerase Chain Reaction
IPTG: IsoPropyl-β-ThioGalactopyranoside
PBS: Phosphate Buffered Saline
PBST: Phosphate Buffered Saline with 0.15% Tween
TMB: 3,3',5,5'-TetraMethylBenzidine It is generally known that proteolytic digestion of an antibody with papain yields three fragments. The fragment containing the $CH_2$ and $CH_3$ domains of the two heavy chains connected by the complete hinge (see FIG. 1) crystallises very easily and was therefore called Fc fragment. The two other fragments are identical and were called Fab fragments, as they contained the antigen-binding site. Digestion with pepsin is such that the two Fab's remain connected via the hinge, forming only two fragments: Fc' and $Fab_2$.

The Fv is the smallest unit of an antibody which still contains the complete binding site (see FIG. 1) and full antigen binding activity. It consists of only the V-domains of the heavy and light chains thus forming a small, heterodimeric variable fragment or Fv. Fv's have a molecular weight of about 25 kD, which is only one sixth of the parent whole antibody (in the case of an IgG). Previously Fv's were only available by proteolysis in a select number of cases (Givol, 1991). The production of Fv's can now be achieved more routinely using genetic engineering methods through cloning and expressing DNA encoding only the V-domains of the antibody of interest. Smaller fragments, such as individual V-domains (Domain Antibodies or dABs, Ward et al., 1989), and even individual CDR's (Williams et al., 1989; Taub et al., 1989) were shown to retain the binding characteristics of the parent antibody. However, this is not achievable on a routine basis: most naturally occurring antibodies need both a $V_H$ and a $V_L$ to retain full immunoreactivity. For example, in the case of $V_H$ D1.3 (Ward et al., 1989), although it still binds hen egg lysozyme (HEL) with an affinity close to that of the parent antibody, it was shown that loss of specificity was observed in that it can no longer distinguish turkey lysozyme from HEL, whereas the Fv can (Berry and Davies, 1992). Although murine dABs can be obtained more routinely from spleen libraries (Ward et al., 1989), the approach is unsustainable because of the many problems associated with their production and physical behaviour: expression is extremely poor, affinity tends to be low, stability and solubility in water is low, and non-specific binding is usually very high. According to the literature a possible explanation of these undesirable characteristics is the exposure of the hydrophobic residues which are normally buried in the $V_H$–$V_L$ interface. The exposed hydrophobic patches are thought to contribute to aggregation of the protein inside the cells and/or in the culture medium, leading to poor expression and/or poor solubility (Anthony et al., 1992; Ward et al., 1989). The hydrophobic patches can also explain the high non-specific binding described by Berry and Davies, 1992. These problems clearly limit the usefulness of these molecules. Most of the Camelid antibodies appear to be an exception to this rule in that they only need one V-domain, namely $V_H$, to specifically and effectively bind an antigen (Hamers-Castermans et al., 1993). In addition, preliminary data indicate that they seem not to suffer from the disadvantages of mouse dABs, as these camelid antibodies or fragments thereof are soluble and have been shown to express well in yeast and Aspergillus moulds. These observations can have important consequences for the production and exploitation of antibody-based products, see patent application WO 94/25591 (UNILEVER et al., first priority date Apr. 29, 1993).

2. Production of Antibody Fragments

Several microbial expression systems have already been developed for producing active antibody fragments, e.g. the production of Fab in various hosts, such as E. coli (Better et al., 1988, Skerra and Plückthun, 1988, Carter et al., 1992), yeast (Horwitz et al., 1988), and the filamentous fungus Trichoderma reesei (Nyyssönen et al., 1993) has been described. The recombinant protein yields in these alternative systems can be relatively high (1–2 g/l for Fab secreted to the periplasmic space of E. coli in high cell density fermentation, see Carter et al., 1992), or at a lower level, e.g. about 0.1 mg/l for Fab in yeast in fermenters (Horwitz et al., 1988), and 150 mg/l for a fusion protein CBHI-Fab and 1 mg/l for Fab in Trichoderma in fermenters (Nyyssönen et al., 1993) and such production is very cheap compared to whole antibody production in mammalian cells (hybridoma, myeloma, CHO). Although the latter can give yields of the order of 1 g/l in high cell density fermentation, it is a time-consuming and very expensive manufacturing method resulting in a cost price of about 1000 £/gram of antibody. It was further demonstrated that plants can be used as hosts for the production of both whole antibodies (Hiatt et al., 1989) and scFv's (Owen et al., 1992, Firek et al., 1993), whereby yields of up to 0.5% of the total soluble protein content in tobacco leaves were mentioned.

The fragments can be produced as Fab's or as Fv's, but additionally it has been shown that a $V_H$ and a $V_L$ can be genetically linked in either order by a flexible polypeptide linker, which combination is known as an scFv (Bird et al. (1988), Huston et al. (1988), and granted patent EP-B-0281604 (GENEX/ENZON LABS INC.; first priority date Sep. 2, 1986).

3. Bivalent and Bispecific Antibodies and Antibody Fragments

The antibody fragments Fab, Fv and scFv differ from whole antibodies in that the antibody fragments carry only a single antigen-binding site. Recombinant fragments with two binding sites have been made in several ways, for example, by chemical cross-linking of cysteine residues introduced at the C-terminus of the $V_H$ of an Fv (Cumber et al., 1992), or at the C-terminus of the $V_L$ of an scFv (Pack and Plückthun, 1992), or through the hinge cysteine residues of Fab's (Carter et al., 1992). Another approach to produce bivalent antibody fragments is described by Kostelny et al. (1992) and Pack and Plückthun (1992) and is based on the inclusion of a C-terminal peptide that promotes dimerization.

When two different specificities are desired, one can generate bispecific antibody fragments. The traditional approach to generate bispecific whole antibodies was to fuse two hybridoma cell lines each producing an antibody having the desired specificity. Because of the random association of immunoglobulin heavy and light chains, these hybrid hybridomas produce a mixture of up to 10 different heavy and light chain combinations, only one of which is the bispecific antibody (Milstein and Cuello, 1983). Therefore, these bispecific antibodies have to be purified with cumbersome procedures, which considerably decrease the yield of the desired product.

Alternative approaches include in-vitro linking of two antigen specificities by chemical cross-linking of cysteine residues either in the hinge or via a genetically introduced C-terminal Cys as described above. An improvement of such in vitro assembly was achieved by using recombinant fusions of Fab's with peptides that promote formation of heterodimers (Kostelny et al., 1992). However, the yield of bispecific product in these methods is far less than 100%.

A more efficient approach to produce bivalent or bispecific antibody fragments, not involving in vitro chemical assembly steps, was described by Holliger et al. (1993). This approach takes advantage of the observation that scFv's secreted from bacteria are often present as both monomers and dimers. This observation suggested that the $V_H$ and $V_L$ of different chains can pair, thus forming dimers and larger complexes. The dimeric antibody fragments, also named "diabodies" by Hollinger et al., in fact are small bivalent antibody fragments that assembled in vivo. By linking the $V_H$ and $V_L$ of two different antibodies 1 and 2, to form "cross-over" chains $V_H1V_L2$ and $V_H2-V_L1$ (see FIG. 2B), the dimerisation process was shown to reassemble both antigen-binding sites. The affinity of the two binding sites was shown to be equal to the starting scFv's, or even to be 10-fold increased when the polypeptide linker covalently linking $V_H$ and $V_L$ was removed, thus generating two proteins each consisting of a $V_H$ directly and covalently linked to a $V_L$ not pairing with the $V_H$ (see FIG. 2C). This strategy of producing bispecific antibody fragments was also described in several patent applications. Patent application WO 94/09131 (SCOTGEN LTD; priority date Oct. 15, 1992) relates to a bispecific binding protein in which the binding domains are derived from both a $V_H$ and a $V_L$ region either present at two chains or linked in an scFv, whereas other fused antibody domains, e.g. C-terminal constant domains, are used to stabilise the dimeric constructs. Patent application WO 94/13804 (CAMBRIDGE ANTIBODY TECHNOLOGY/MEDICAL RESEARCH COUNCIL; first priority date Dec. 4, 1992) relates to a polypeptide containing a $V_H$ and a $V_L$ which are incapable of associating with each other, whereby the V-domains can be connected with or without a linker.

Mallender and Voss, 1994 (also described in patent application WO 94/13806; DOW CHEMICAL CO; priority date Dec. 11, 1992) reported the in vivo production of a single-chain bispecific antibody fragment in E. coli. The bispecificity of the bivalent protein was based on two previously produced monovalent scFv molecules possessing distinct specificities, being linked together at the genetic level by a flexible polypeptide linker. The thus formed $V_H1$-linker-$V_L1$-linker-$V_H2$-linker-$V_L2$ fragment (see FIG. 2A) was shown to contain both antigen binding specificities 1 and 2. (1=anti-fluorescein, 2=anti-single-stranded DNA). Traditionally, whenever single-chain antibody fragments are referred to, a single molecule consisting of one heavy chain linked to one (corresponding) light chain in the presence or absence of a polypeptide linker is implicated. When making bivalent or bispecific antibody fragments through the 'diabody' approach (Holliger et al., (1993) and patent application WO 94/09131) or by the 'double scFv' approach (Mallender and Voss, 1994 and patent application WO 94/13806), again the $V_H$ is linked to a (the corresponding) $V_L$.

It is realised that claims 32 and 33 of patent application WO 93/11161 (ENZON INC.; priority date Nov. 25, 1991) and the corresponding passages in that specification on page 22, lines 1–10 may read on a polypeptide comprising two $V_L$'s fused together via a flexible polypeptide linker, and on a polypeptide comprising two $V_H$'s fused together via a flexible polypeptide linker, respectively. However, no examples were given to substantiate this approach, thus it was in fact a hypothetical possibility instead of an actually produced compound.

A skilled person would not have expected that such approach would be viable for at least three reasons. Firstly, it is widely recognised that immunoglobulin heavy chains (excluding the above described camel immunoglobulins) have very limited solubility and spontaneously precipitate out of aqueous solution when isolated from their light chain partners. Secondly, several groups have shown (Ward et al., 1989, Berry and Davies, 1992, and Anthony et al., 1992) that expression of $V_H$'s in the absence of $V_L$'s is hampered by extremely poor yields of unstable product with many undesirable properties, e.g. non-specific binding. Thirdly in patent application WO 94/13804 it was described on page 31 lines 10–12, that in computer modelling experiments they could not model as heterodimers $V_H$—$V_H$ and $V_L$—$V_L$ given the constraints of short linkers.

Thus the simple suggestion given in patent application WO 93/11161 is not an enabling disclosure leading a skilled person to try with a reasonable expectation of success whether such suggestion would work; therefore, that patent application should not be considered as relevant prior art for the present invention.

SUMMARY OF THE INVENTION

The present invention provides a bispecific or bivalent antibody fragment analogue, which comprises a binding complex containing two polypeptide chains, one of which comprises two times a variable domain of a heavy chain ($V_H$) in series and the other comprises two times a variable domain of a light chain ($V_L$) in series.

In one aspect of the invention one chain of the antibody fragment analogue comprises a first $V_H$ ($V_H$-A) connected to a second $V_H$ ($V_H$–B) and the other chain comprises a first $V_L$ ($V_L$–A) connected to a second $V_L$ ($V_L$–B). In a preferred embodiment of this aspect one chain comprises a first $V_H$ ($V_H$–A) followed by a second $V_H$ ($V_H$–B), thus [$V_H$–A * $V_H$–B], and the other chain comprises a first $V_L$ ($V_L$–A) preceded by a second $V_L$ ($V_L$–B), thus [$V_L$–B * $V_L$–A]. For some embodiments of this aspect the two $V_H$'s are directly connected to each other, but for other embodiments of this aspect of the invention the two $V_L$'s are directly connected to each other. According to another embodiment of this aspect of the invention the two $V_H$'s are connected to each other by a linker and also the two $V_L$'s are connected to each other by a linker. Such a linker usually comprises at least one amino acid residue.

According to a special embodiment of this aspect of the invention one chain comprises a first $V_H$ ($V_H$–A) followed by a second $V_H$ ($V_H$–B), thus [$V_H$–A * $V_H$–B], and the other chain comprises a first $V_L$ ($V_L$–A) followed by a second $V_L$ ($V_L$–B), thus [$V_L$–A * $V_L$–B], and in which the two $V_H$'s are connected to each other by a linker and also the two $V_L$'s are connected to each other by a linker, whereas each linker comprises at least 10 amino acid residues.

According to the above aspect of the invention with A being different from B there are provided bispecific antibody fragment analogues.

According to another aspect of the invention the specificities A and B are the same resulting in a bivalent antibody fragment.

According to a further aspect of the invention the bispecific or bivalent antibody fragment analogues can be used in a diagnostic technique or for immunoassays, in a purification method, for therapy, or in other methods in which immunoglobulins or fragments thereof are used. Such uses are well-known in the art.

The invention also provides a process for producing the antibody fragments of the invention in that a host is transformed by incorporating into that host a DNA encoding the two $V_H$'s with or without a connecting linker and a DNA encoding the two $V_L$'s with or without a connecting linker. Preferably the two DNA's are placed in a dicistronic arrangement.

It is also possible that the two linked $V_H$'s and the two linked $V_L$'s are produced separately by different hosts, after which the linked $V_H$'s produced by one host can be combined with the linked $V_L$'s produced by the other host. The hosts can be selected from the group consisting of prokaryotic bacteria of which examples are Gram-negative bacteria, e.g. *E. coli*, and Gram-positive bacteria, e.g. *B. subtilis* or lactic acid bacteria, lower eukaryotes examples of which are yeasts, e.g. belonging to the genera Saccharomyces, Kluyveromyces, or Trichoderma, moulds, e.g. belonging to the genera Aspergillus and Neurospora, and higher eukaryotes, examples of which are plants, e.g. tobacco, and animal cells, examples of which are myeloma cells and CHO cells. The techniques to transform a host by genetic engineering methods in order to have a desirable polypeptide produced by such host are well-known to persons skilled in the art as is evident from the literature mentioned above under the heading "Background of the invention and prior art".

BRIEF DESCRIPTION OF THE DRAWINGS

FIG. 4 shows the nucleotide sequence of the EcoRI-HindIII insert of pUR.4124 containing DNA (see SEQ ID NO: 1) encoding $V_L$Lys-Linker-$V_H$Lys (see SEQ ID NO: 2).

FIG. 5 shows the nucleotide sequence of the HindIII-EcoRI insert of plasmid Fv.3418 (see SEQ ID NO: 3) containing DNA encoding pelB leader-$V_H$3418 (see SEQ ID NO: 4) and DNA encoding pelB leader-$V_L$3418 (see SEQ ID NO: 5).

FIG. 6 shows the nucleotide sequence of the HindIII-EcoRI insert of plasmid Fv.4715-myc (see SEQ ID NO: 6) containing DNA encoding pelB leader-$V_H$4715 (see SEQ ID NO: 7) and DNA encoding pelB leader-$V_L$4715-Myc tag (see SEQ ID NO: 8).

FIG. 7 shows the nucleotide sequence of the HindIII-EcoRI insert of scFv.4715-myc containing DNA (see SEQ ID NO: 9) encoding pelB leader-$V_H$4715-Linker-$V_L$4715-Myc tag (see SEQ ID NO: 10).

FIGS. 8A and 8B show the nucleotide sequence of the HindIII-EcoRI insert of pGOSA.E (see SEQ ID NO: 11) containing DNA encoding pelB leader-$V_H$4715-Linker-V$_L$3418 (see SEQ ID NO: 12) and DNA encoding pelB leader-$V_L$3418-Linker-$V_H$4715 (see SEQ ID NO: 13).

FIGS. 37A and 37B show the construction of plasmid pGOSA.G.

FIG. 43 shows the construction of plasmid PGOSA.Y.

Figure 1:
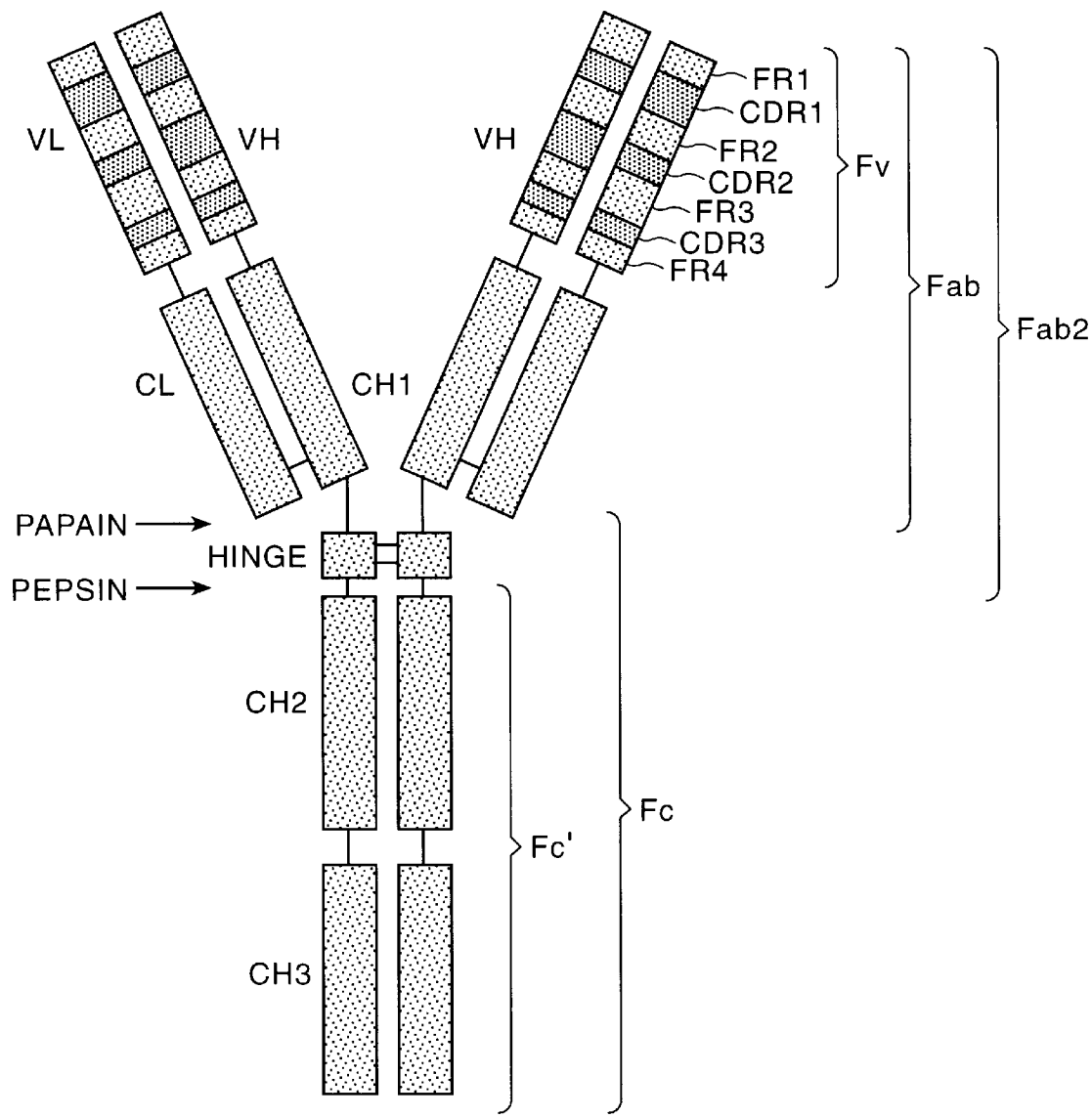
FIG. 1 depicts in schematic form the structure of a typical antibody (immunoglobulin) molecule.
Figure 2A:
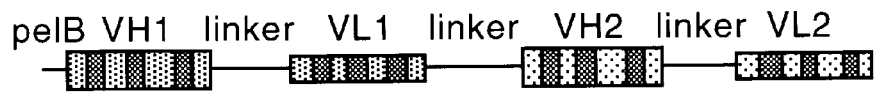
FIG. 2 shows a schematic representation of published arrangements of heavy and light chain V-domain gene fragments that have been proven to produce bispecific antibody fragments.
Figure 2B:
Figure 2C:
Figure 3:
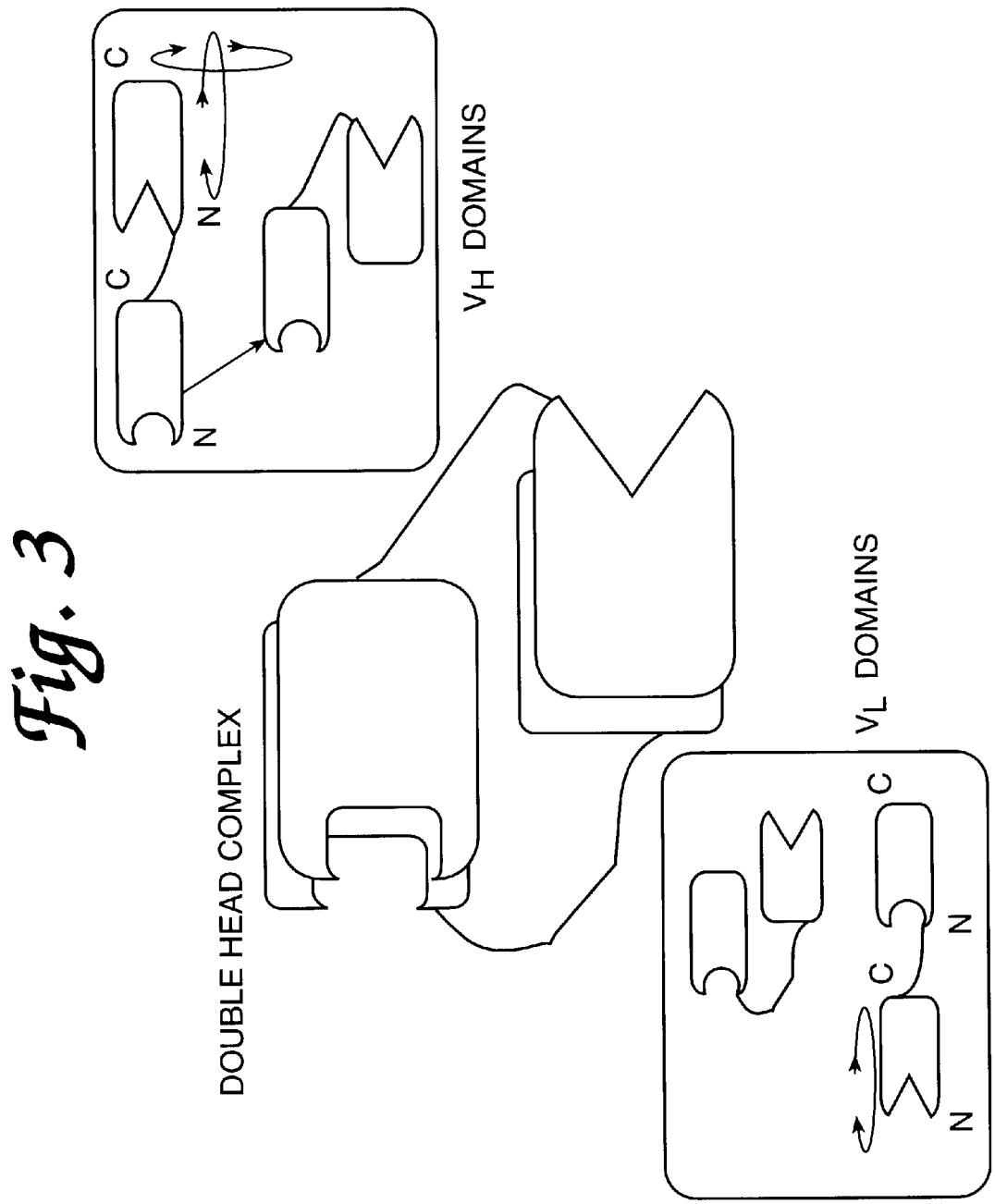
FIG. 3 shows in diagrammatic form the suggested arrangement of the V-domains of a double head antibody fragment according to the invention with the V-domains in the following order: $V_H$A–$V_H$B+$V_L$B–$V_L$A.

Table 1 shows the nucleotide sequence of the oligonucleotides used to produce the constructs described in this specification. Restriction sites encoded by these primers are underlined.

Table 2 gives an overview of all GOSA constructs described in this specification.

Table 2A describes intermediate constructs that were not further tested.

Table 2B describes the dicistronic constructs.

Table 2C describes the monocistronic constructs.

DETAILED DESCRIPTION OF THE INVENTION

In this specification the construction of an antibody fragment analogue consisting of a two chain protein complex is described, in which one of the chains consists of two heavy chain V-domains and the other chain consists of the two corresponding light chain V-domains in either order. The variable domains are linked either directly or through a polypeptide linker. Subsequent molecular modelling of this combination suggested that the protein chains could fold such that both binding sites are fully accessible, provided that the connecting linkers are kept long enough to span 30 to 35 Å.

Whereas in patent application WO 93/11161 it is explicitly described that for the above described bispecific complexes two flexible polypeptide linkers in the self assembling complex are required, the present invention illustrated here describes in particular the construction of a two chain protein complex containing only one linker or no linkers at all. The latter antibody fragment analogue thus consists of a two chain protein complex containing one polypeptide chain comprising heavy chain V-domains fused directly together and another polypeptide chain comprising the corresponding light chain V-domains fused together, both fusions in the absence of linkers. But also two chain protein complexes in which each chain comprises a linker between the two variable domains can be used as antibody fragment analogues according to the invention as described below with construct pGOSA.E. However, the two chain complexes containing only one linker or no linker at all are preferred. The abbreviation GOSA used in this specification relates to a combination of glucose oxidase and *Streptococcus sanguis*.

In this specification evidence is provided that these antibody fragment analogues ("double heads") contain both antigen binding specificities of the Fv's used to generate these bispecific antibody fragments. It is exemplified that these type of constructs according to the invention can be used to target the enzyme glucose oxidase to whole bacteria, using antibody fragments derived from hybridomas expressing antibodies directed against these antigens.

The present invention is now described by reference to some specific examples, which are included for purposes of illustration only and are not intended to limit the scope of the invention.

EXAMPLES

General Experimental

Strains, Plasmids and Media

All cloning steps were performed in *E. coli* JM109 (endA1, recA1, gyrA96, thi, hsdR17($r_K^-$, $m_K^+$), relA1, supE44, Δ(lac-proAB), [F', traD36, proAB, lacI$^q$ZΔM15]. *E. coli* cultures were grown in 2×TY medium (16 g tryptone, 10 g yeast extract, 5 g NaCl per liter $H_2O$), where indicated supplemented with 2% glucose and/or 100 μg/ml ampicillin. Transformations were plated out on SOBAG plates (20 g tryptone, 5 g yeast extract, 15 g agar, 0.5 g NaCl per liter $H_2O$ plus 10 mM $MgCl_2$, 2% glucose, 100 μg/ml ampicillin) The expression vectors used are derivatives of pUC19. The oligonucleotide primers used in the PCR reactions were synthesized on an Applied Biosystems 381A DNA Synthesiser by the phosphoramidite method.

Expression of GOSA Constructs

Colonies from freshly transformed JM109 plated onto SOBAG plates were used to inoculate 2×TY medium supplemented with 100 μg/ml ampicillin, 2% glucose. Cultures were shaken at 37° C. to an $OD_{600}$ in the range of 0.5 to 1.0. Cells were pelleted by centrifugation and the supernatant was removed. The pelleted cells were resuspended in 2×TY medium with 100 μg/ml ampicillin, 1 mM IPTG, and grown for a further 18 hours at 25° C. Cells were pelleted by centrifugation and the supernatant, containing the secreted chains, used directly in an ELISA. The proteins in the periplasm of the pelleted cells were extracted by resuspending the cell pellet in 1/20 of the original culture volume of lysis buffer (20% sucrose, 200 mM Tris-HCl pH 7.5, 1 mM EDTA, 500 μg/ml lysozyme). After incubation at 25° C. for 20 minutes an equal volume of $H_2O$ was added and the incubation was continued for another 20 minutes. The suspension was spun at 10.000 g for 15 minutes and the supernatant containing the periplasmic proteins was used directly in an ELISA.

Figure 11:
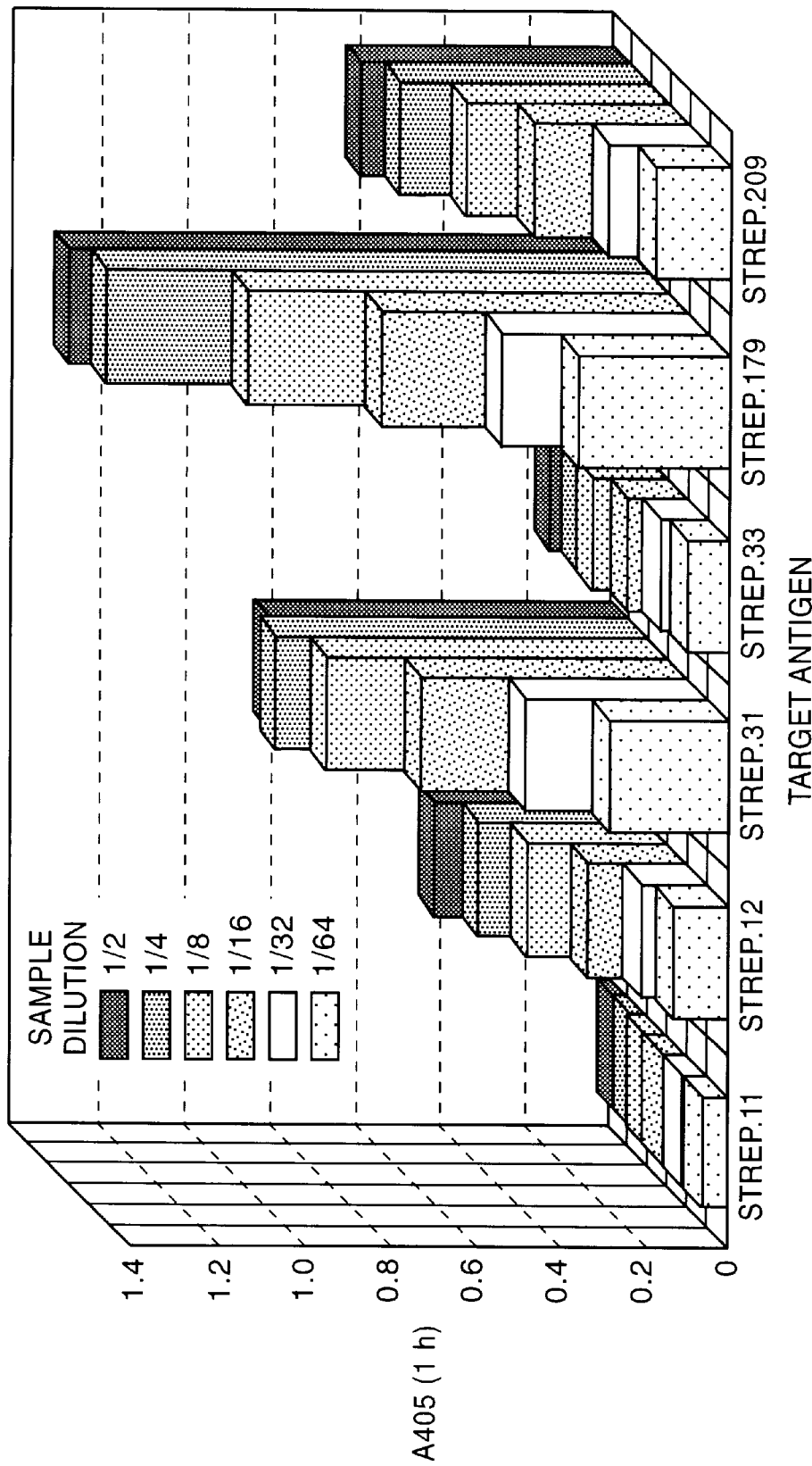
FIG. 11 shows the specificity of Streptococcus binding of scFv.4715-myc.

ELISA 96 well ELISA plates (Greiner HC plates) were activated overnight at 37° C. with 200 μl/well of an 1/10 dilution of an over night culture of Streptococcus cells in 0.05 M sodium carbonate buffer at pH=9.5. Following one wash with PBST, the antigen sensitised plates were pre-blocked for 1 hour at 37° C. with 200 μl/well blocking buffer (2% BSA, 0.15% Tween in PBS). Samples containing 50 μl blocking buffer plus 50 μl culture supernatants or periplasmic cell extracts (neat or diluted with PBS) were added to the Streptococcus sensitised plate and incubated for 2 hours at 37° C. Following 4 washes with PBS-T, 100 μl of blocking buffer containing glucose oxidase (50 μg/ml) was added to every well. After incubation at 37° C. for 1 hour unbound glucose oxidase was removed by 4 washes with PBS-T. Bound glucose oxidase was detected by adding 100 μl substrate to each well (70 mM Na-citrate, 320 mM Na-phosphate, 27 mg/ml glucose, 0.5 μg/ml HRP, 100 μg/ml TMB). The colour reaction was stopped after 1 hour by the addition of 35 μl 2 M HCl and the A450 was measured (compare FIGS. 11/15).

Affinity Purification of GOSA Antibody Fragments

GOSA.E, GOSA.V, GOSA.S and GOSA.T were partially purified by affinity chromatography. 100 ml periplasmic extract of each of these constructs was loaded onto a Glucose-oxidase-Sepharose column (CNBr-Sepharose, Pharmacia) prepared according to the manufacturer's instructions. After extensive washes with PBS the bound GOSA antibody fragments were eluted in 0.1M glycine buffer at pH=2.8. The fractions were neutralised with Tris and analysed by polyacrylamide gel electrophoresis followed by silver staining and tested for the presence of double head activity.

EXAMPLE 1

Construction of the pGOSA Double Head Expression Vectors

In this Example the construction of a two chain protein complex is described, in which one of the chains consists of two heavy chain V-domains and the other chain consists of the two corresponding light chain V-domains. The variable domains are linked either directly or through a polypeptide linker. The expression vectors used are derivatives of a pUC19 derived plasmid containing a HindIII-EcoRI fragment that in the case of plasmid scFv.4715-myc contains a DNA fragment encoding one pelB signal sequence fused to the N-terminus of the $V_H$ that is directly linked to the corresponding $V_L$ of the antibody through a connecting flexible peptide linker, $(Gly_4Ser)_3$ (present in SEQ ID NO: 2 as amino acids 109–123 and in SEQ ID NO: 10 as amino acids 121–135), thus generating a single-chain molecule (see FIG. 7).

In the dual-chain Fv and the pGOSA expression vectors, the DNA fragments encoding both the $V_H$ and $V_L$ of the antibody are preceded by a ribosome binding site and a DNA sequence encoding the pelB signal sequence in an artificial dicistronic operon under the control of a single inducible promoter (see FIGS. 5, 6 and 8A and 8B). Expression of these constructs is driven by the inducible lacZ promoter. The nucleotide sequence of the HindIII-EcoRI inserts of the plasmids pUR.4124, Fv.3418, Fv.4715-myc and scFv.4715-myc constructs used for the generation of the bispecific antibody fragments are given in FIGS. 4–7, respectively. Moreover, a culture of E. coli cells harbouring plasmid scFv.4715-myc and a culture of E. coli cells harbouring plasmid Fv.3418 were deposited under the Budapest Treaty at the National Collection of Type Cultures (Central Public Health Laboratory) in London (United Kingdom) with deposition numbers NCTC 12916 and NCTC 12915, respectively. In agreement with Rule 28 (4) EPC, or a similar arrangement for a State not being a Contracting State of the EPC, it is hereby requested that a sample of such deposit, when requested, will be submitted to an expert only. The construction of PGOSA.E (see FIGS. 8A and 8B for the HindIll-EcoRI insert of pUC19) involved several cloning steps. The appropriate restriction sites in the various domains were introduced by PCR directed mutagenesis using the oligonucleotides listed in Table 1 below. The PGOSA.E derivatives pGOSA.V, pGOSA.S and PGOSA.T with only one or no linker sequence are derived from the pGOSA.E construct by removing the linker sequences by means of PCR directed mutagenesis with oligonucleotides listed in Table 1 below.

TABLE 1

| DBL.1 | 5'-CAC CAT CTC CAG AGA CAA TGG CAA G-3' | (= SEQ ID NO: 14) |
| DBL.2 | 5'-GAG CGC GAG CTC <u>GGC CGA ACC GGC C</u>[1]GA TCC GCC ACC GCC AGA GCC-3' | (= SEQ ID NO: 15) |
| DBL.3 | 5'-CAG GAT CC<u>G GCC GGT TCG GCC</u>[1] CAG GTC CAG CTG CAA CAG TCA GGA-3' | (= SEQ ID NO: 16) |
| DBL.4 | 5'-CTA CAT <u>GAA TTC</u>[2] <u>GCT AGC</u>[3] TTA TTA TGA GGA GAC GGT GAC GGT GGT CCC TTG GC-3' | (= SEQ ID NO: 17) |
| DBL.5 | 5'-TAA TAA <u>GCT AGC</u>[3] GGA GCT GCA TGC AAA TTC TAT TTC-3' | (= SEQ ID NO: 18) |
| DBL.6 | 5'-ACC AAG <u>CTC GAG</u>[4] ATC AAA CGG GG-3' | (= SEQ ID NO: 19) |
| DBL.7 | 5'-AAT GTC <u>GAA TTC</u>[2] <u>GTC GAC</u>[5] TCC GCC ACC GCC AGA GCC-3' | (= SEQ ID NO: 20) |
| DBL.8 | 5'-ATT GGA <u>GTC GAC</u>[5] ATC GAA CTC ACT CAG TCT CCA | (= SEQ ID NO: 21) |

TABLE 1-continued

```
         TTC TCC-3'

DBL.9    5'-TGA AGT GAA TTC² GCG GCC GC⁶T TAT TAC CGT TTG    (= SEQ ID NO: 22)
         ATT TCG AGC TTG GTC CC-3'

DBL.10   5'-CGA ATT CGG TCA CC⁸G TCT CCT CAC AGG TCC AGT     (= SEQ ID NO: 23)
         TGC AAC AG-3'

DBL.11   5'-CGA ATT CTC GAG⁴ ATC AAA CGG GAC ATC GAA CTC     (= SEQ ID NO: 24)
         ACT CAG TCT CC-3'

DBL.12   5'-CGA ATT CGG TCA CC⁸G TCT CCT CAC AGG TGC AGT     (= SEQ ID NO: 25)
         TGC AGG AG-3'

PCR.51   5'-AGG T(C/G)(A/C) A(C/A)C TGC AG⁷(C/G) AGT C(A/T)G (= SEQ ID NO: 26)
         G-3'

PCR.89   5'-TGA GGA GAC GGT GAC C⁸GT GGT CCC TTG GCC CC-3'   (= SEQ ID NO: 27)

PCR.90   5'-GAC ATT GAG CTC⁹ ACC CAG TCT CCA-3'              (= SEQ ID NO: 28)

PCR.116  5'-GTT AGA TCT CGA G⁴CT TGG TCC C-3'                (= SEQ ID NO: 29)
```

1=SfiI, 2=EcoRI, 3=NheI, 4=XhoI, 5=SalI, 6=NotI, 7=PstI, 8=BstEII, 9=SacI

Figure 9:
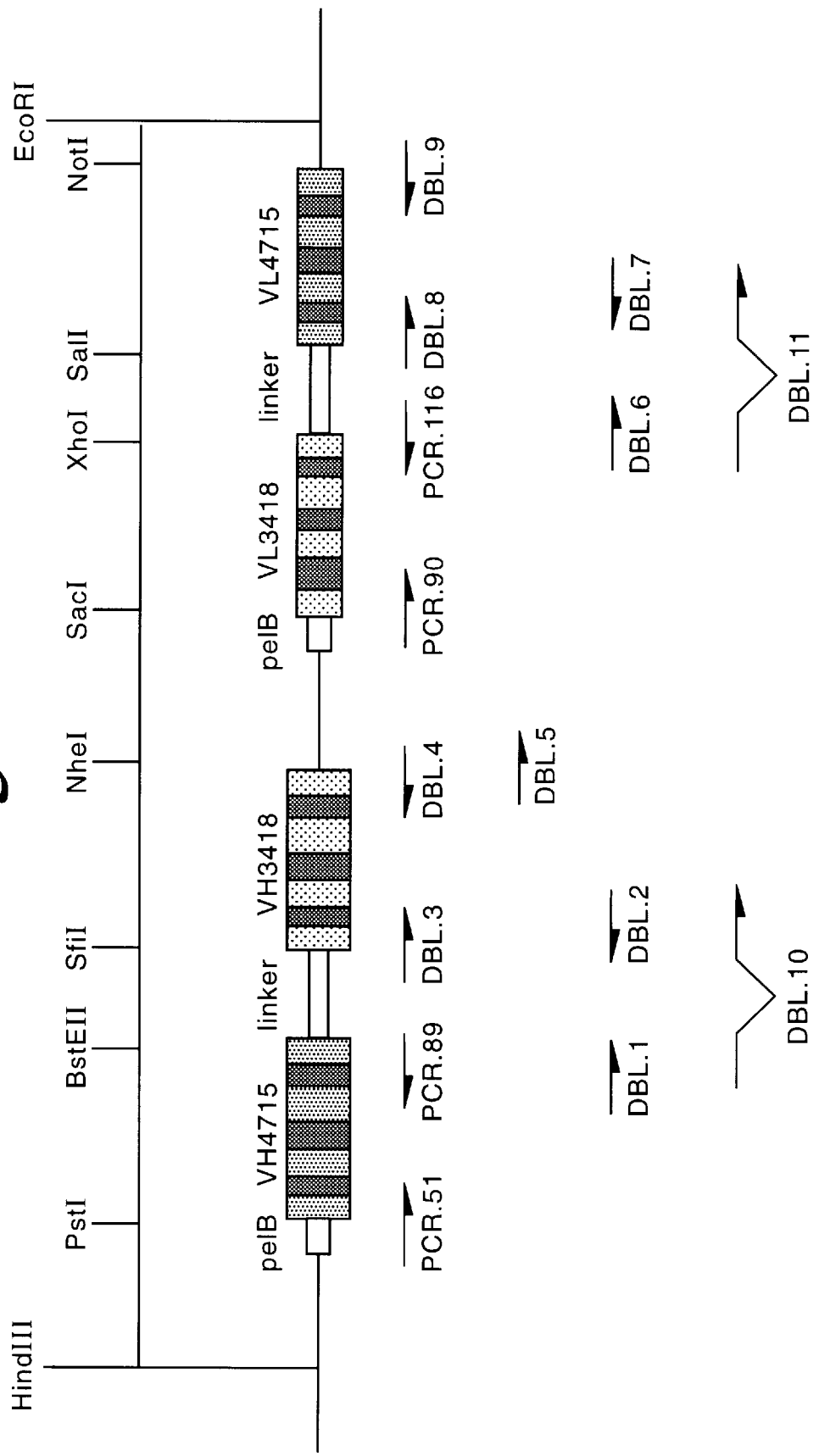
FIG. 9 gives an overview of the oligonucleotides and their positions in pGOSA.E that can be used to replace V-domain gene fragments.
Figure 10:
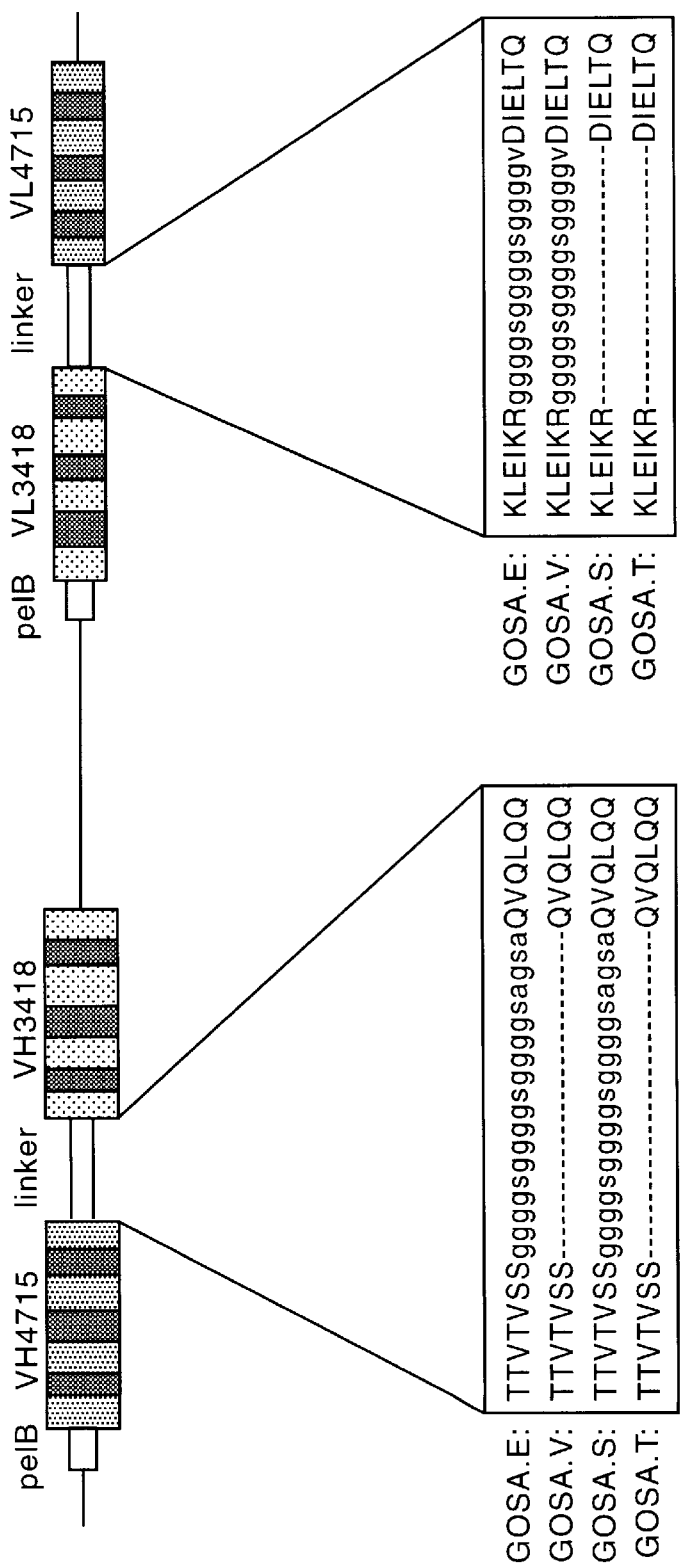
FIG. 10 illustrates the amino acid sequence of the $V_H$—$V_H$ and $V_L$—$V_L$ domain junctions in fusion polypeptides GOSA.E (see amino acids 114–145 in SEQ ID NO: 12 and amino acids 102–128 in SEQ ID NO: 13), GOSA.V (see SEQ ID NO: 30 and amino acids 102–128 in SEQ ID NO: 13), GOSA.S (see amino acids 114–145 in SEQ ID NO: 12 and SEQ ID NO: 31) and GOSA.T (see SEQ ID NO: 30 and SEQ ID NO: 31).

These three constructs lack some of the restriction sites at the new joining points. The $V_H A$–$V_H B$ gene fragment without a linker lacks the 5' $V_H B$ SfiI site. The $V_L B$–$V_L A$ gene fragment without a linker lacks the 5' $V_L A$ SalI site. The position of the oligonucleotides in the PGOSA constructs given in Table 1 are shown in FIG. 9. The pGOSA expression vectors and the oligonucleotides in Table 1 have been designed to enable most specificities to be cloned into the pGOSA constructs. FIG. 10 shows the amino acid sequence of the junctions between the $V_H A$–$V_H B$ and $V_L B$–$V_L A$ fragments encoded by DNA present in pGOSA.E, pGOSA.V, pGOSA.S and pGOSA.T. A more detailed description of the preparation of pGOSA.E, pGOSA.V, PGOSA.S and pGOSA.T is given in Example 5.

EXAMPLE 2

Bifunctional Binding Activity of GOSA Double Heads

In this Example we provide evidence that the above described molecules ("double heads"), i.e. the two chain protein complexes, contain both antigen binding specificities of the Fv's used to generate these multi-functional antibody fragment analogues. FIG. 12–15 show that GOSA.E, GOSA.V, GOSA.S and GOSA.T can be used to specifically target the enzyme glucose oxidase to several *Streptococcus sanguis* strains using antibody fragments derived from hybridoma's expressing antibodies directed against these antigens.

Comparison of the binding specificity of the GOSA constructs (see FIGS. 12–15) and the binding specificity of the scFv.4715-myc (see FIG. 11) shows that the fine specificity of the anti-*Streptococcus sanguis* scFv.4715 is preserved in the GOSA "double heads".

EXAMPLE 3

FPLC Analysis of GOSA Double Heads

Partially purified GOSA.E, GOSA.V, GOSA.S and GOSA.T samples (estimated to be 50–80% pure by polyacrylamide gel electrophoresis) were analysed on a Pharmacia FPLC Superose 12 column. The analysis was performed using PBS at a flow rate of 0.3 ml/minute. Eluate was monitored at 280 nm and 0.3 ml fractions were collected and analysed by ELISA. Usually GOSA.E, GOSA.V, GOSA.S and GOSA.T samples only gave one GOSA double head activity peak as determined by ELISA (see FIGS. 16–18). The position of this peak in the elution pattern indicated that the molecular weight of the GOSA double head is 40–50 kD. Since this molecular weight corresponds to the expected molecular weight of the $V_H 2 + V_L 2$ double head dimer, the conclusion is justified that GOSA.E, GOSA.V, GOSA.S and GOSA.T are primarily produced as dimeric molecules. Occasionally an activity peak with an apparent molecular weight of ≈200 kD was observed (see FIG. 16). The presence of Glucose Oxidase activity in these fractions (data not shown) indicate that these fractions contain GOSA double head complexed with glucose oxidase that was eluted with the GOSA sample from the glucose oxidase-sepharose affinity matrix.

EXAMPLE 4

Production of Other Double Heads

The methods described in the previous Examples were used to produce other double heads, which also appeared to be active against the antigens for which they were developed. These other double heads had the following specificities:

anti-*S. sanguis*/anti-beta-HCG,
anti-*S. sanguis*/anti-urease,
anti-*S. sanguis*/anti-hen-egg-lysozyme,
anti-beta-HCG/anti-hen-egg-lysozyme,
anti-hen-egg-lysozyme/anti-glucose oxidase,
anti-huIgG/anti-glucose oxidase,
anti-urease/anti-glucose oxidase,
anti-lacto-peroxidase/anti-glucose oxidase,
anti-alpha-HCG/anti-glucose oxidase, and
anti-reactive-Red-6/anti-glucose oxidase.

EXAMPLE 5

Detailed Description of the Preparation of Intermediate Constructs pGOSA.A, pGOSA.B pGOSA.C and pGOSA.D and Their Use for the Preparation of Plasmid pGOSA.E and Its Derivatives PGOSA.V, PGOSA.S and PGOSA.T

Oligonucleotides and PCR

The primary structures of the oligonucleotide primers used in the construction of the bispecific 'pGOSA' constructs are shown in Table 1 above. Reaction mixture used for amplification of DNA fragments were 10 mM Tris-HCl, pH 8.3, 2.5 mM $MgCl_2$, 50 mM KCl, 0.01% gelatin (w/v), 0.1% Triton X-100, 400 mM of each dNTP, 5.0 units of Vent DNA polymerase (New England Biolabs), 100 ng of template DNA, and 500 ng of each primer (for 100 µl reactions). Reaction conditions were: 94° C. for 4 minutes, followed by 33 cycles of each 1 minute at 94° C., 1 minute at 55° C., and 1 minute 72° C.

Plasmid DNA\Vector\Insert Preparation and Ligation\Transformation

Plasmid DNA was prepared using the 'Qiagen P-100 Midi-DNA Preparation' system. Vectors and inserts were prepared by digestion of 10 µg (for vector preparation) or 20 µg (for insert preparation) with the specified restriction endonucleases under appropriate conditions (buffers and temperatures as specified by suppliers). Modification of the DNA ends with Klenow DNA polymerase and dephosphorylation with Calf Intestine Phosphorylase were performed according to the manufacturers instructions. Vector DNAs and inserts were separated through agarose gel electrophoresis and purified with DEAE-membranes NA45 (Schleicher & Schuell) as described by Maniatis et al. Ligations were performed in 20 µl volumes containing 30 mM Tris-HCl pH 7.8, 10 mM $MgCl_2$, 10 mM DTT, 1 mM ATP, 300–400 ng vector DNA, 100–200 ng insert DNA and 1 Weiss unit $T_4$ DNA ligase. After ligation for 2–4 h at room temperature, $CaCl_2$ competent *E. coli* JM109 (Maniatis) were transformed using 7.5 µl ligation reaction. The transformation mixtures were plated onto SOBAG plates and grown overnight at 37° C. Correct clones were identified by restriction analysis and verified by automated dideoxy sequencing (Applied Biosystems).

Restriction Digestion of PCR Products

Following amplification each reaction was checked for the presence of a band of the appropriate size by agarose gel electrophoresis. One or two 100 µl PCR reaction mixtures of each of the PCR reactions PCR.I–PCR.X (FIG. 20–29), together containing approximately 2–4 µg DNA product were subjected to phenol-chloroform extraction, chloroform extraction and ethanol precipitation. The DNA pellets were washed twice with 70% ethanol and allowed to dry. Next, the PCR products were digested overnight (18 h) in the presence of excess restriction enzyme in the following mixes at the specified temperatures and volumes.

PCR.I 50 mM Tris-HCl pH 8.0, 10 mM $MgCl_2$, 50 mM NaCl, 4 mM spermidine, 0.4 µg/ml BSA, 4 µl (=40 U) SacI, 4 µl (=40 U) BstEII, in 100 µl total volume at 37° C.

PCR.II 10 mM Tris-Acetate pH 7.5, 10 mM $MgAc_2$, 50 mM KAc (1x "One-Phor-All" buffer ex Pharmacia), 4 µl (=48 U) SfiI, in 50 µl total volume at 50° C. under mineral oil. After overnight digestion, PCR.II-SfiI was digested with EcoRI (overnight at 37° C.) by the addition of 16 µl $H_2O$, 30 µl 10x "One-Phor-All" buffer (Phanmacia) (100 mM Tris-Acetate pH 7.5, 100 mM $MgAc_2$, 500 mM KAc) and 4 µl (=40 U) EcoRI.

PCR. III 10 mM Tris-Acetate pH 7.5, 10 mM $MgAc_2$, 50 mM KAc (1x "One-Phor-All" buffer {Pharmacia}), 4 µl (=40 U) NheI, 4 µl (=40 U) SacI, in 100 µl total volume at 37° C.

PCR.IV 20 mM Tris-Acetate pH 7.5, 20 mM $MgAc_2$, 100 mM KAc (2x "One-Phor-All" buffer {Pharmacia}), 4 µl (=40 U) XhoI, 4 µl (=40 U) EcoRI, in 100 µl total volume at 37° C.

PCR.V 20 nM Tris-Acetate pH 7.5, 20 mM $MgAc_2$, 100 mM KAc (2x "One-Phor-All" buffer {Pharmacia}), 4 µl (=40 U) SalI, 4 µl (=40 U) EcoRI, in 100 µl total volume at 37° C.

PCR.VI 10 mM Tris-Acetate pH 7.5, 10 mM $MgAc_2$, 50 mM KAc (1x "One-Phor-All" buffer {Pharmacia}), 4 µl (=48 U) SfiI, in 50 µl total volume at 50° C. under mineral oil. After overnight digestion, PCR.VI-SfiI was digested with NheI (overnight at 37° C.) by the addition of 41 µl $H_2O$, 5 µl 10x "One-Phor-All" buffer (Pharmacia) (100 mM Tris-Acetate pH 7.5, 100 mM $MgAc_2$, 500 mM KAc) and 4 µl (=40 U) NheI.

PCR.VII 50 mM Tris-HCl, pH 8.0, 10 mM $MgCl_2$, 50 mM NaCl, 4 mM spermidine, 0.4 µg/ml BSA, 4 µl (=40 U) NheI, 4 µl (=40 U) BstEII, in 100 µl total volume at 37° C.

PCR.VIII 20 mM Tris-Acetate pH 7.5, 20 mM $MgAc_2$, 100 mM KAc (2x "One-Phor-All" buffer {Pharmacia}), 4 µl (=40 U) EcoRI, in 50 µl total volume at 37° C. After overnight digestion, PCR.VIII-EcoRI was digested with XhoI (overnight at 37° ) by the addition of 46 µl $H_2O$ and 4 µl (=40 U) XhoI.

PCR.IX 25 mM Tris-Acetate, pH 7.8, 100 mM KAc, 10 mM MgAc, 1 mM DTT (1x "Multi-Core" buffer {Promega}), 4 mM spermidine, 0.4 µg/ml BSA, 4 µl (=40 U) NheI, 4 µl (=40 U) BstEII, in 100 µl total volume at 37° C.

PCR.X 50 mM Tris-HCl, pH 8.0, 10 mM $MgCl_2$, 50 mM NaCl, 4 mM permidine, 0.4 µg/ml BSA, 4 µl (=40 U) PstI, 4 µl (=40 U) EcoRI, in 100 µl total volume at 37° C.

| The digested PCR fragments | |
|---|---|
| PCR.I-SacI/BstEII, | PCR.II-SfiI/EcoRI, |
| PCR.III-NheI/SacI, | PCR.IV-XhoI/EcoRI, |
| PCR.V-SalI/EcoRI, | PCR.VI-SfiI/NheI, |
| PCR.VII-BstEII/NheI, | PCR.VIII-XhoI/EcoRI, |
| PCR.IX-BstEII/NheI, and | PCR.X-PstI/EcoRI | were purified on an 1.2% agarose gel using DEAE-membranes NA45 (Schleicher & Schuell) as described by Maniatis et al. The purified fragments were dissolved in $H_2O$ at a concentration of 100–150 ng/µl.

Construction of the pGOSA Double Head Expression Vectors

The construction of pGOSA.E (see FIGS. 8A and 8B) involved several cloning steps that produced 4 intermediate constructs PGOSA.A to pGOSA.D (see FIG. 29–33). The final expression vector pGOSA.E and the oligonucleotides in Table 1 above have been designed to enable most specificities to be cloned into the final pGOSA.E construct (FIG. 9). The upstream $V_H$ domain can be replaced by any PstI-BstEII $V_H$ gene fragment obtained with oligonucleotides PCR.51 and PCR.89 (see Table 1 above). The oligonucleotides DBL.3 and DBL.4 (see Table 1 above) were designed to introduce SfiI and NheI restriction sites in the $V_H$ gene fragments thus allowing cloning of those $V_H$ gene fragments into the SfiI-NheI sites as the downstream $V_H$ domain. All $V_L$ gene fragments obtained with oligonucleotides PCR.116 and PCR.90 (see Table 1 above) can be cloned into the position of the $V_L$.3418 gene fragment as a SacI-XhoI fragment. A complication here however is the presence of an internal SacI site in the $V_H$.3418 gene fragment. Oligonucleotides DBL.8 and DBL.9 (see Table 1 above) are designed to allow cloning of $V_L$ gene fragments into the position of the $V_L$.4715 gene fragment-as a SalI-NotI fragment. The pGOSA.E derivatives PGOSA.V, pGOSA.S and PGOSA.T with only one or no linker sequences contain some aberrant restriction sites at the new joining points. The $V_HA$-$V_HB$ construct without a linker lacks the 5' $V_HB$ SfiI site. The $V_HB$ fragment is cloned into these constructs as a BstEII/NheI fragment using oligonucleotides DBL.10 or DBL.11 and DBL.4 (see Table 1 above). The $V_LB$-$V_LA$ construct without a linker lacks the 5' $V_LA$ SalI site. The $V_LA$ fragment is cloned into these constructs as a XhoI/EcoRI fragment using oligonucleotides DBL.11 and DBL.9 (see Table 1 above).

In the following part of the description the following linkers are mentioned which are also present in the sequence listing:

the $(Gly_4Ser)_3$ linker, present in SEQ ID NO: 2 as amino acids 109–123 and SEQ ID NO: 10 as amino acids 121–135, the $(Gly_4Ser)_3AlaGlySerAla$ linker (=linkerA), present in SEQ ID NO: 12 as amino acids 121–139, and the $(Gly_4Ser)_2Gly_4Val$ linker (=linkerV), present in SEQ ID NO: 13 as amino acids 108–122.

pGOSA.A

This plasmid is derived from both the Fv.4715-myc construct and the scFv.4715-myc construct.

Figure 19:
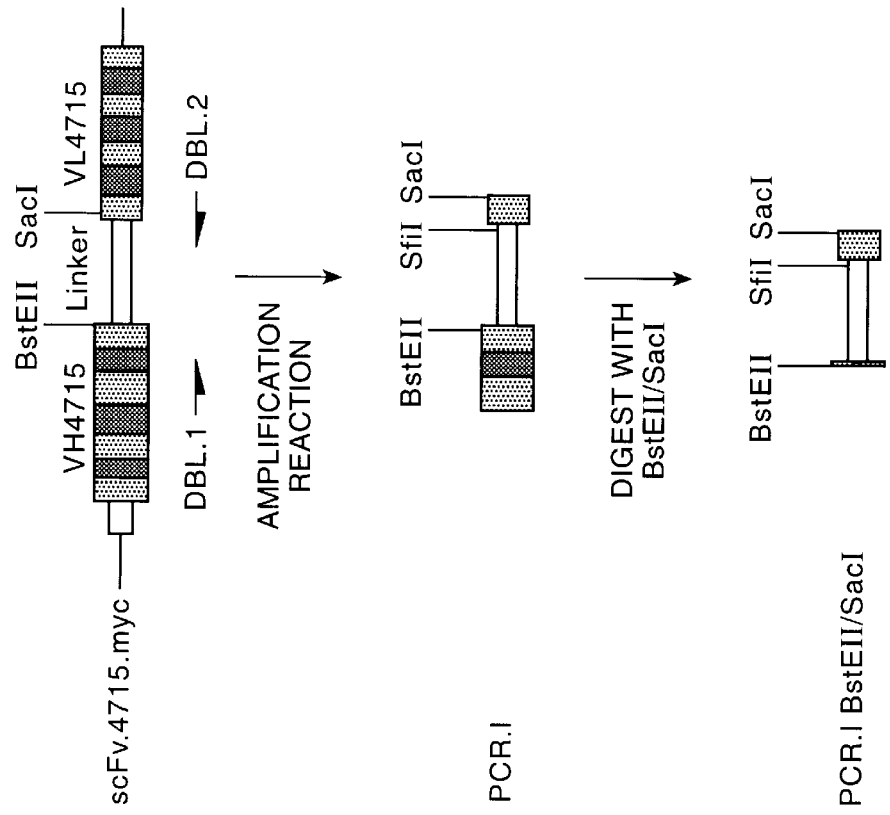
FIG. 19 shows the source of fragment PCR.I BstEII/SacI.
Figure 30:
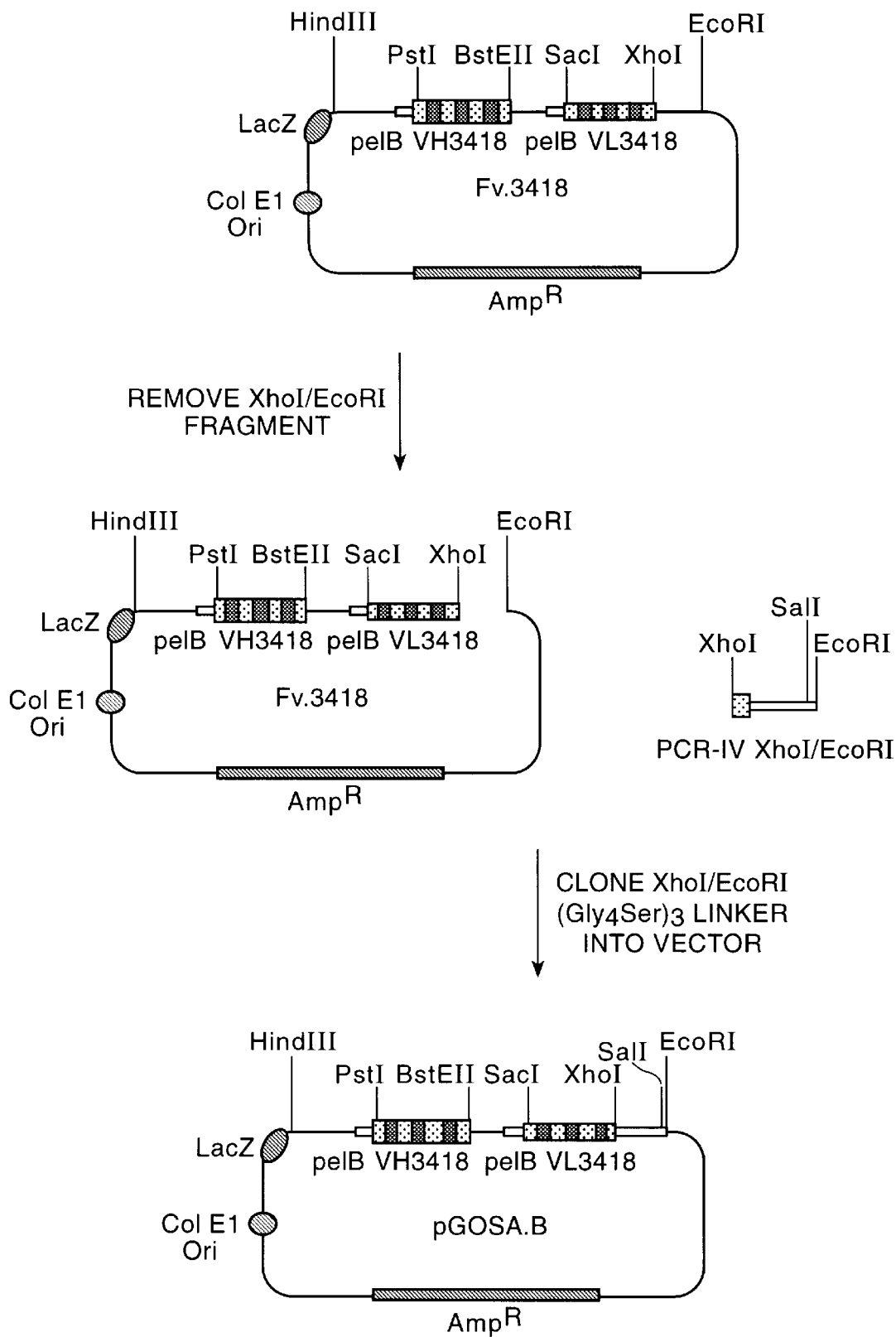
FIG. 30 shows the construction of plasmid pGOSA.B.

An SfiI restriction site was introduced between the DNA sequence encoding the $(Gly_4Ser)_3$ linker and the gene fragment encoding the $V_L$ of the scFv.4715-myc construct (see FIG. 30). This was achieved by replacing the BstEII-SacI fragment of the latter construct by the fragment PCR-I BstEII/SacI (FIG. 19) that contains an SfiI site between the DNA encoding the $(Gly_4Ser)_3$ linker and the $V_L$.4715 gene fragment. The introduction of the SfiI site also introduced 4 additional amino acids (AlaGlySerAla) between the $(Gly_4Ser)_3$ linker and $V_L$.4715 resulting in a $(Gly_4Ser)_3AlaGlySerAla$ linker (linkerA). The oligonucleotides used to produce PCR-I (DBL.1 and DBL.2, see Table 1 above) were designed to match the sequence of the framework-3 region of $V_H$.4715 and to prime at the junction of the DNA encoding the $(Gly_4Ser)_3$ linker and the $V_L$.4715 gene fragment, respectively. Thus PGOSA.A can be indicated as: pelB-$V_H$4715-linkerA- (SfiI) -$V_L$4715-myc.

pGOSA.B

Figure 22:
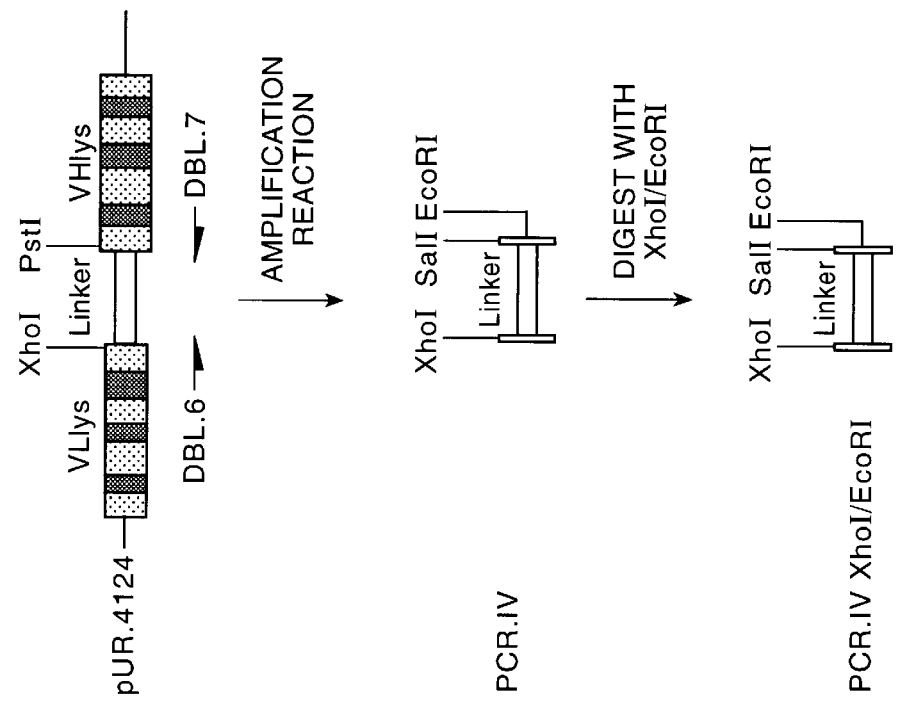
FIG. 22 shows the source of fragment PCR.IV XhoI/EcoRI.
Figure 21:
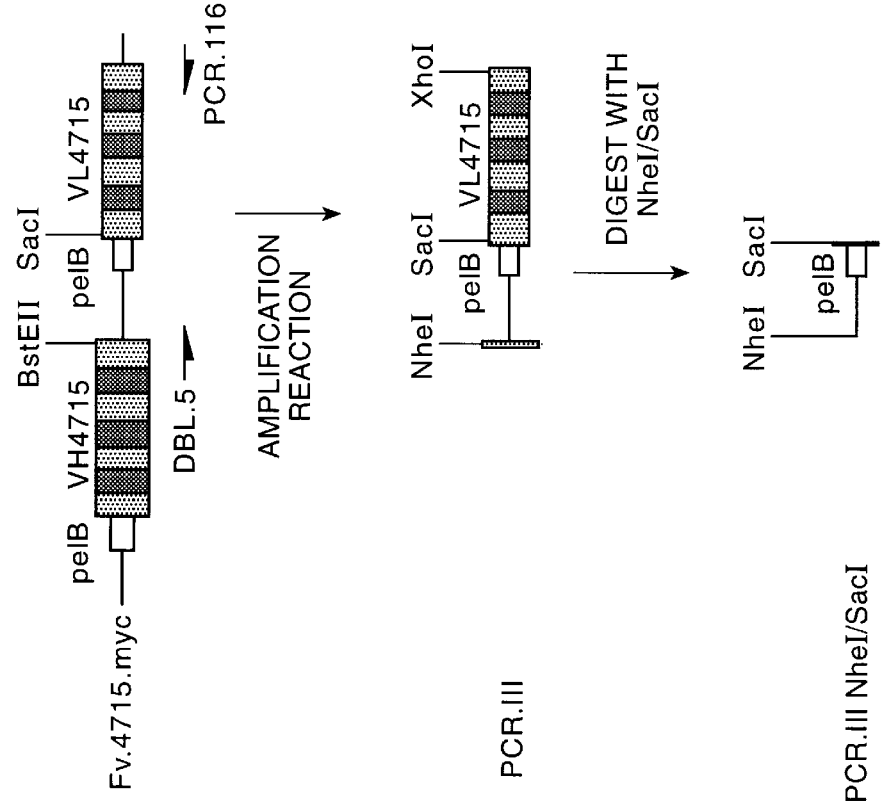
FIG. 21 shows the source of fragment PCR.III NheI/SacI.
Figure 24:
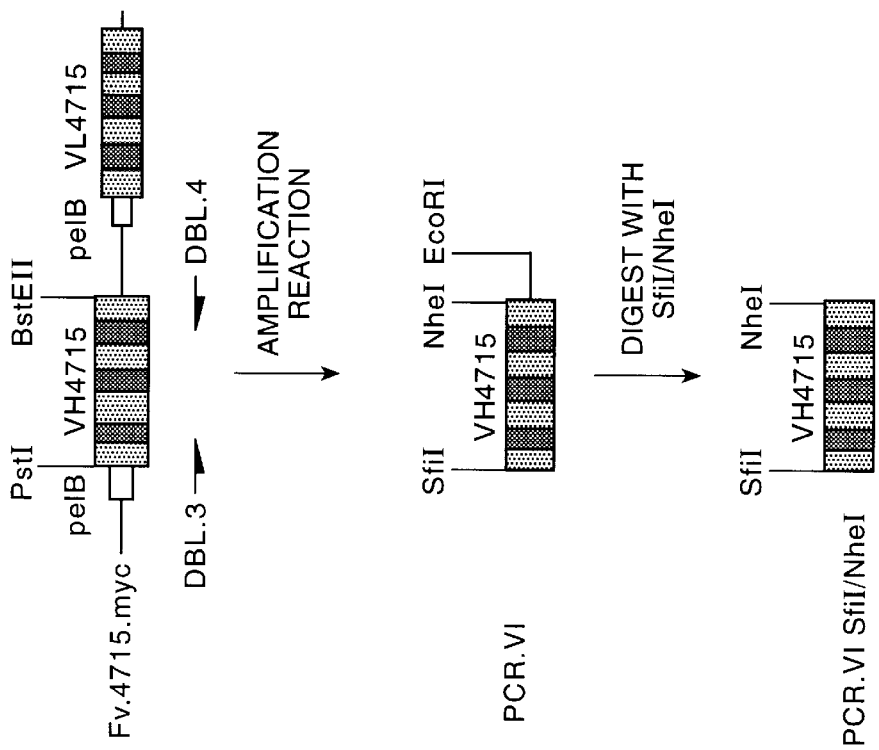
FIG. 24 shows the source of fragment PCR.VI SfiI/NheI.
Figure 23:
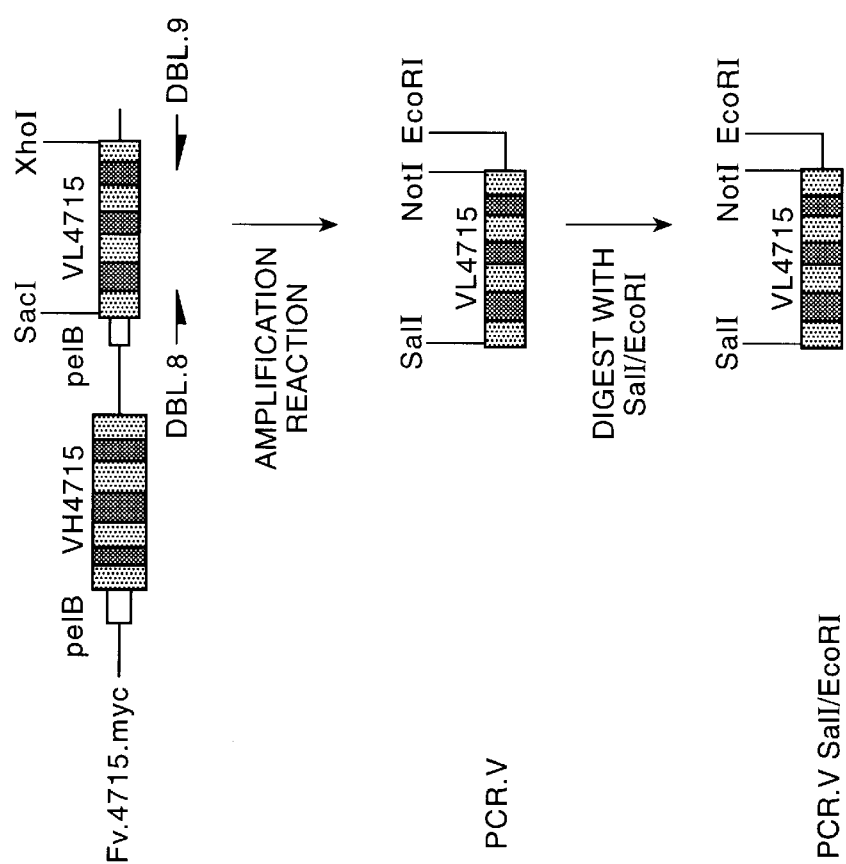
FIG. 23 shows the source of fragment PCR.V SalI/EcoRI.
Figure 31:
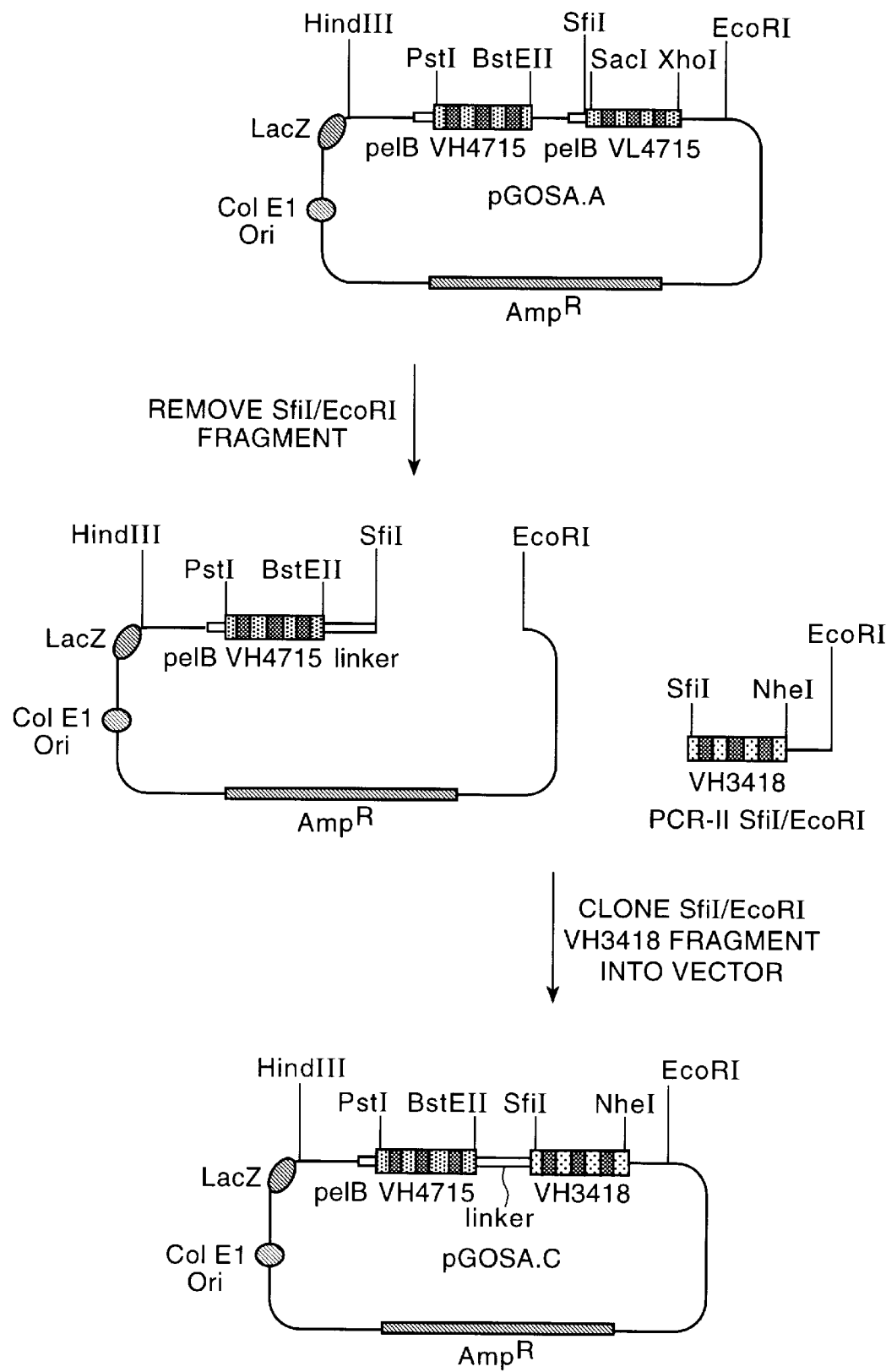
FIG. 31 shows the construction of plasmid PGOSA.C.
Figure 32:
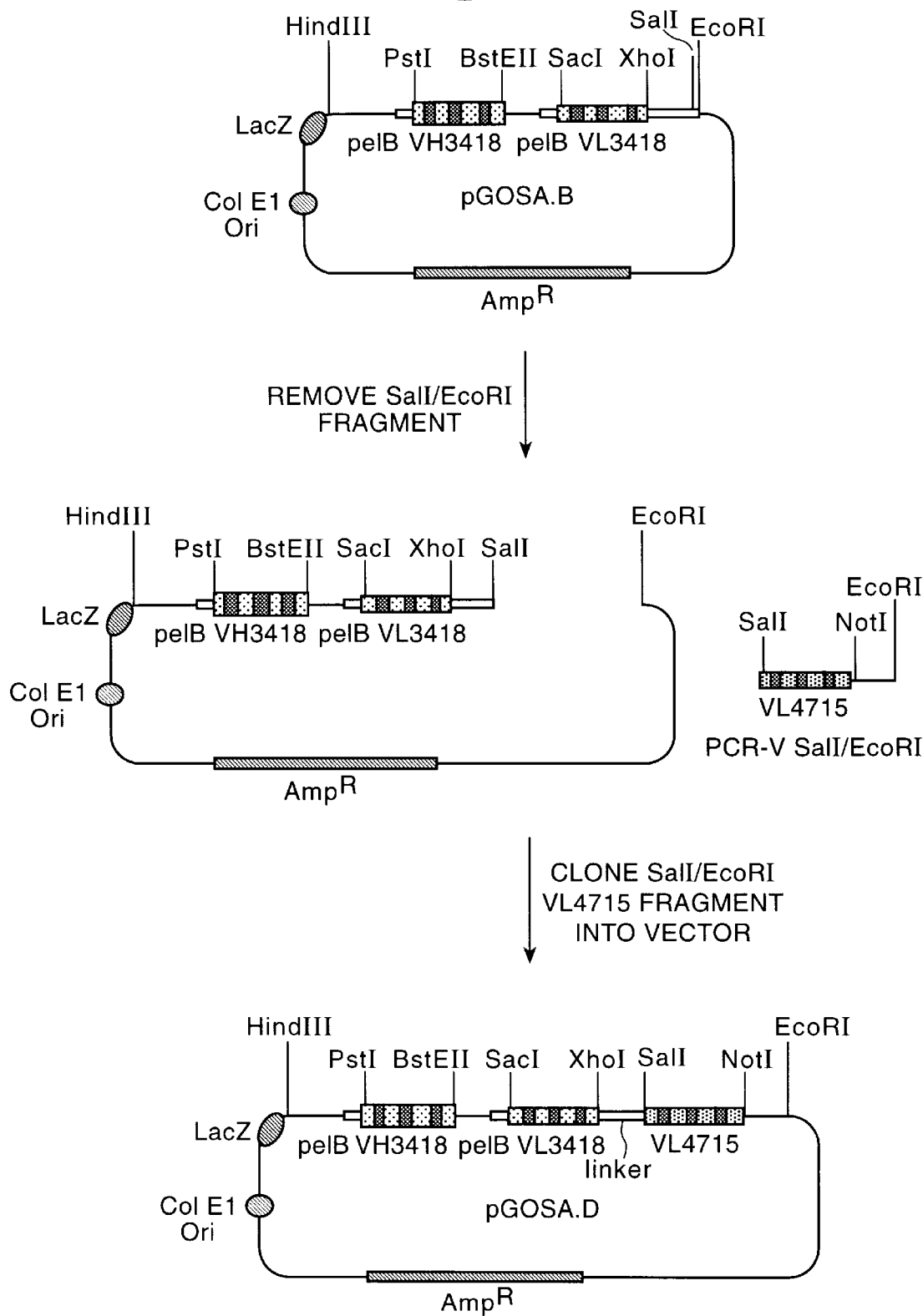
FIG. 32 shows the construction of plasmid pGOSA.D.
Figure 33:
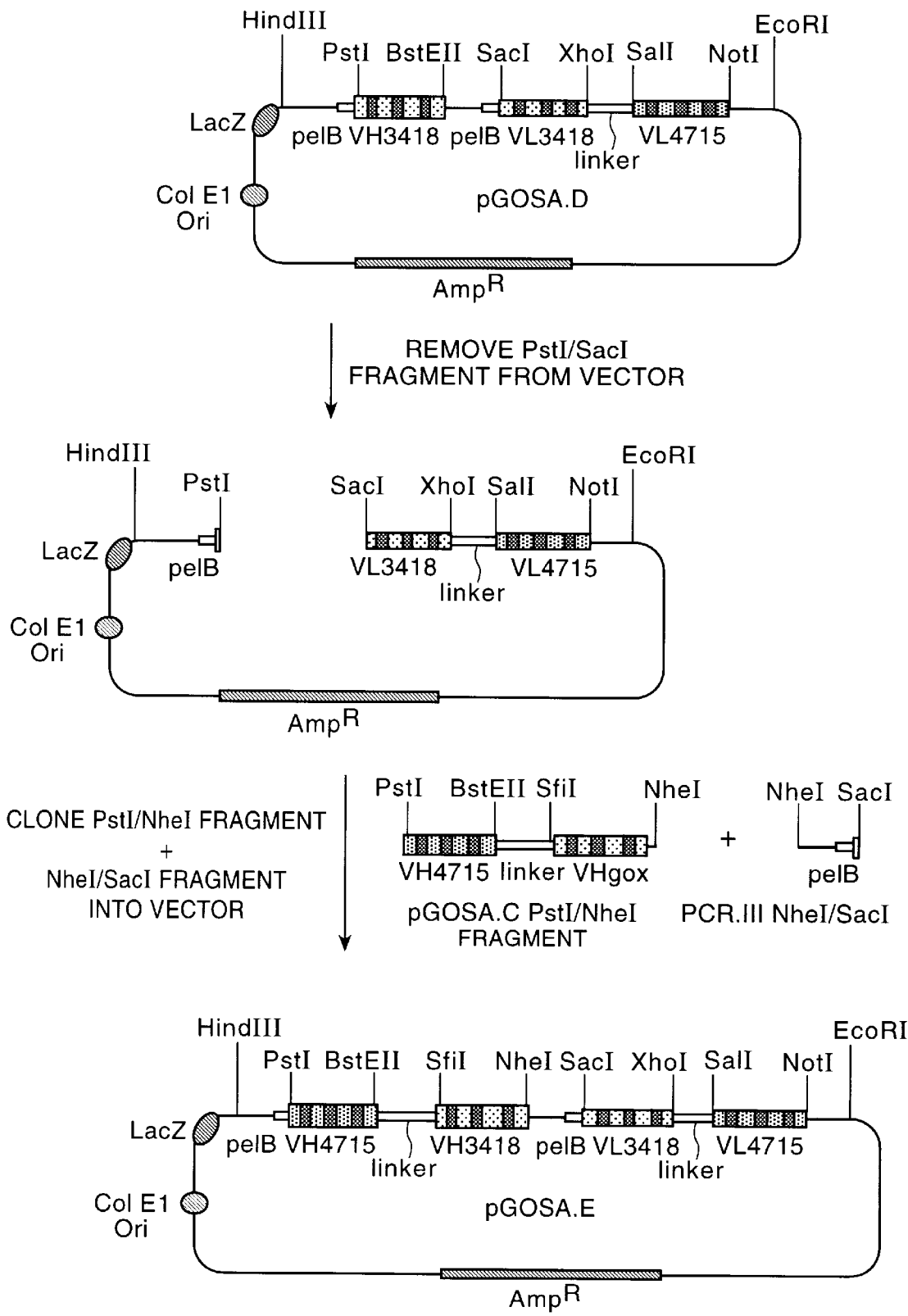
FIG. 33 shows the construction of plasmid pGOSA.E.
Figure 34:
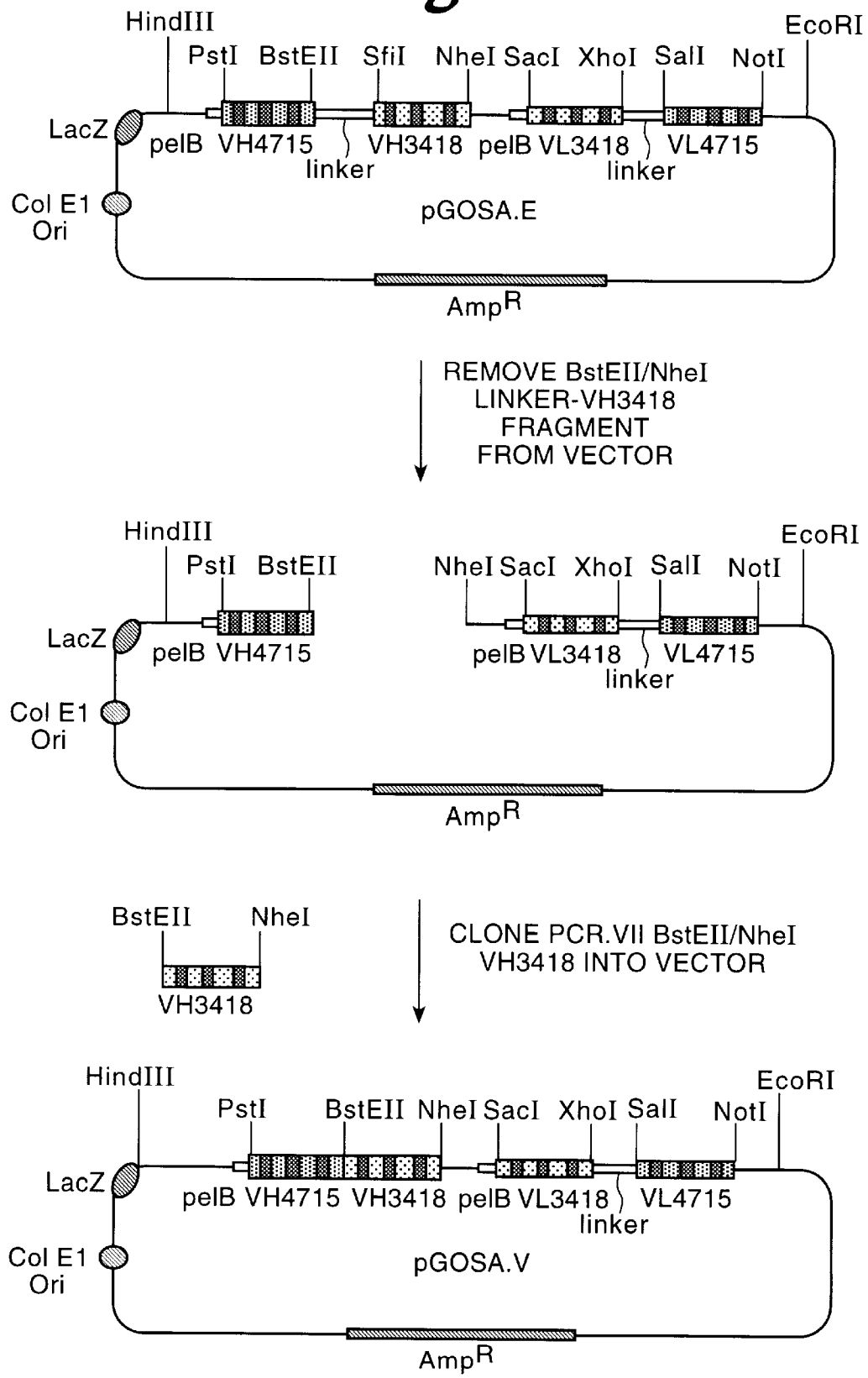
FIG. 34 shows the construction of plasmid pGOSA.V.

This plasmid is derived from plasmid Fv.3418 (see FIG. 31). The XhoI-EcoRI fragment of plasmid Fv.3418 comprising the 3' end of DNA encoding framework-4 of the $V_L$ including the stop codon was removed and replaced by the fragment PCR-IV XhoI/EcoRI (FIG. 22). The oligonucleotides used to produce PCR-IV (DBL.6 and DBL.7, see Table 1 above) were designed to match the sequence at the junction of the $V_L$ and the $(Gly_4Ser)_3$ linker perfectly (DBL.6), and to be able to prime at the junction of the $(Gly_4Ser)_3$ linker and the $V_H$ in pUR.4124 (DBL.7). DBL.7 removed the PstI site in the $V_H$ (silent mutation) and introduced a SalI restriction site at the junction of the $(Gly_4Ser)_3$ linker and the $V_H$, thereby replacing the last Ser of the linker by a Val residue resulting in a $(Gly_4Ser)_2Gly_4Val$ linker (linkerV). Thus pGOSA.B can be indicated as:

pelB-$V_H$3418+pelB-$V_L$3418-linkerV- (SalI-EcoRI)

pGOSA.C

This plasmid contains DNA encoding $V_H$.4715 linked by the $(Gly_4Ser)_3AlaGlySerAla$ linker to $V_H$.3418 (see FIG. 31), thus: pelB-$V_H$4715-linkerA-$V_H$3418.

Figure 20:
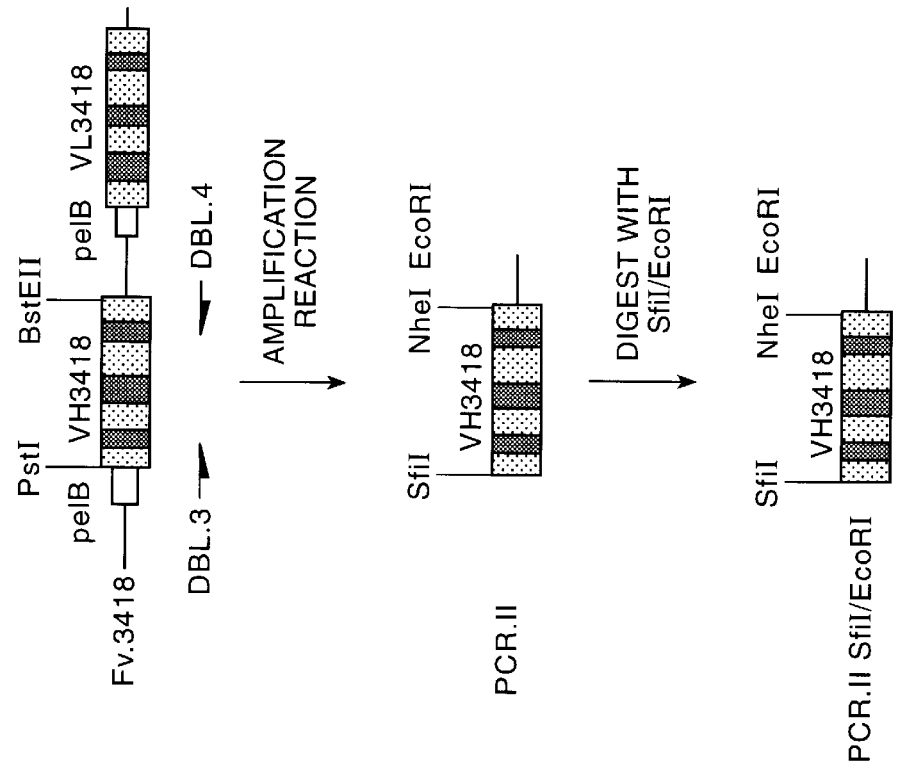
FIG. 20 shows the source of fragment PCR.II SfiI/EcoRI.

This construct was obtained by replacing the SfiI-EcoRI fragment from pGOSA.A encoding $V_L$.4715 by the fragment PCR-II SfiI/EcoRI containing the $V_H$.3418 gene (see FIG. 20). The oligonucleotides used to produce PCR-II (DBL.3 and DBL.4, see Table 1 above) hybridize in the framework-1 and framework-4 region of the gene encoding $V_H$.3418, respectively. DBL.3 was designed to remove the PstI restriction site (silent mutation) and to introduce an SfiI restriction site upstream of the $V_H$ gene. DBL.4 destroys the BstEII restriction site in the framework-4 region and introduces an NheI restriction site downstream of the stopcodon.

pGOSA.D

This plasmid contains a dicistronic operon comprising the $V_H$.3418 gene and DNA encoding $V_L$.3418 linked by the $(Gly_4Ser)_2Gly_4Val$ linker to $V_L$.4715 (see FIG. 32), thus:

pelB-$V_H$3418+pelB-$V_L$3418-linkerV-$V_L$4715.

This construct was obtained by digesting plasmid pGOSA.B with SalI-EcoRI and inserting the fragment PCR-V SalI/EcoRI (FIG. 23) containing the $V_L$.4715 gene. The oligonucleotides used to obtain PCR-V (DBL.8 and DBL.9, see Table 1 above) were designed to match the nucleotide sequence of the framework-1 and framework-4 regions of the $V_L$.4715 gene, respectively. DBL.8 removed the SacI site from the framework-1 region (silent mutation) and introduced a SalI restriction site upstream of the $V_L$.4715 gene. DBL.9 destroyed the XhoI restriction site in the framework-4 region of the $V_L$.4715 gene (silent mutation) and introduced a NotI and an EcoRI restriction site downstream of the stop codon.

PGOSA.E

This plasmid contains a dicistronic operon comprising DNA encoding $V_H$.4715 linked by the (Gly4Ser)$_3$AlaGlySerAla linker to $V_H$.3418 plus DNA encoding $V_L$.3418 linked by the $(Gly_4Ser)_2Gly_4Val$ linker to $V_L$.4715 (see FIG. 33), thus:

pelB-$V_H$4715-linkerA-$V_H$3418+pelB-$V_L$3418-linkerV-$V_L$4715.

Both translational units are preceded by a ribosome binding site and DNA encoding a pelB leader sequence. This plasmid was obtained by a three-point ligation by mixing the vector resulting from pGOSA.D after removal of the $V_H$3418-encoding PstI-SacI insert with the PstI-NheI pGOSA.C insert containing $V_H$.4715 linked to $V_H$.3418 and the PCR-III NheI/SacI fragment (see FIG. 21). The remaining PstI-SacI pGOSA.D vector contains the 5' end of the framework-1 region of $V_H$3418 up to the PstI restriction site and $V_L$.3418 linked by the (Gly$_4$Ser)$_2$Gly$_4$Val linker to $V_L$.4715 starting from the SacI restriction site in $V_L$.3418. The PstI-NheI PGOSA.C insert contains $V_H$.4715 linked by the (Gly$_4$Ser)$_3$-AlaGlySerAla linker to $V_H$.3418, starting from the PstI restriction site in the framework-1 region in $V_H$.4715. The NheI-SacI PCR-III fragment provides the ribosome binding site and DNA encoding the pelB leader sequence for the $V_L$.3418-(Gly$_4$Ser)$_2$Gly$_4$Val-$V_L$.4715 construct. The oligo-nucleotides DBL.5 and PCR.116 (see Table 1 above) used to generate PCR-III were designed to match the sequence upstream of the ribosome binding site of $V_L$.4715 in Fv.4715 and to introduce an NheI restriction site (DBL.5), and to match the framework-4 region of $V_L$.3418 (PCR.116).

pGOSA.V

Figure 25:
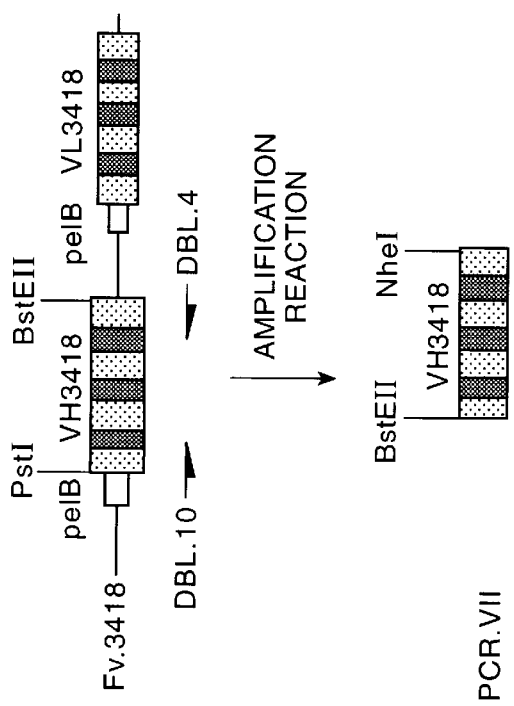
FIG. 25 shows the source of fragment PCR.VII BstEII/NheI.
Figure 35:
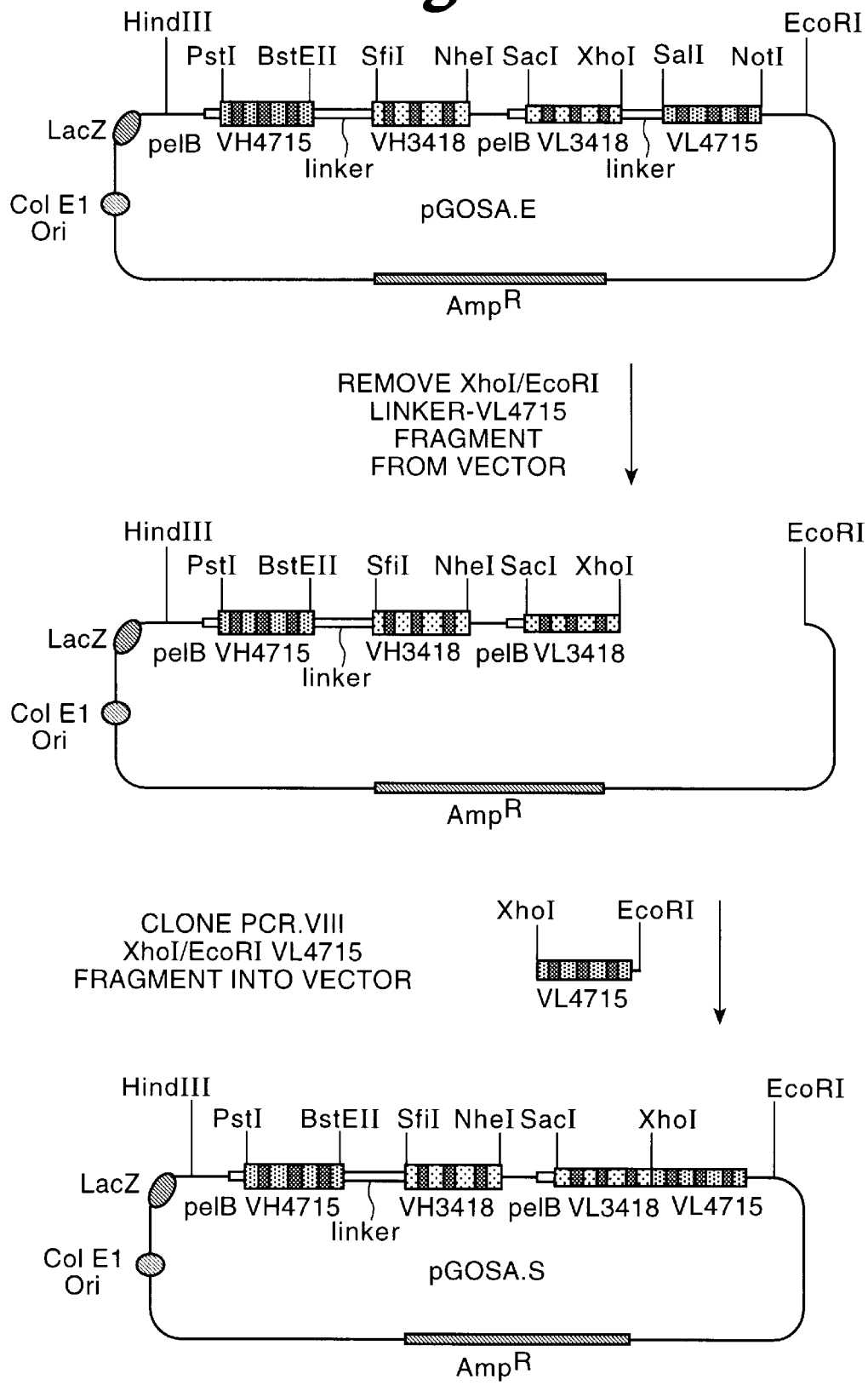
FIG. 35 shows the construction of plasmid pGOSA.S.

This plasmid is derived from PGOSA.E (see FIG. 35) from which the BstEII/NheI fragment containing DNA encoding linkerA-$V_H$.3418 was excised and replaced by the fragment PCR-VII BstEII/NheI containing the $V_H$.3418 gene (see FIG. 25). The resulting plasmid pGOSA.V contains $V_H$.3418 linked directly to the framework-4 region of $V_H$.4715, plus $V_L$.4715 linked by the (Gly$_4$Ser)$_2$Gly$_4$Val linker to the framework-4 region of $V_L$.3418, thus:

pelB-$V_H$4715*$V_H$3418+pelB-$V_L$3418-linkerV-$V_L$4715.

pGOSA.S

Figure 26:
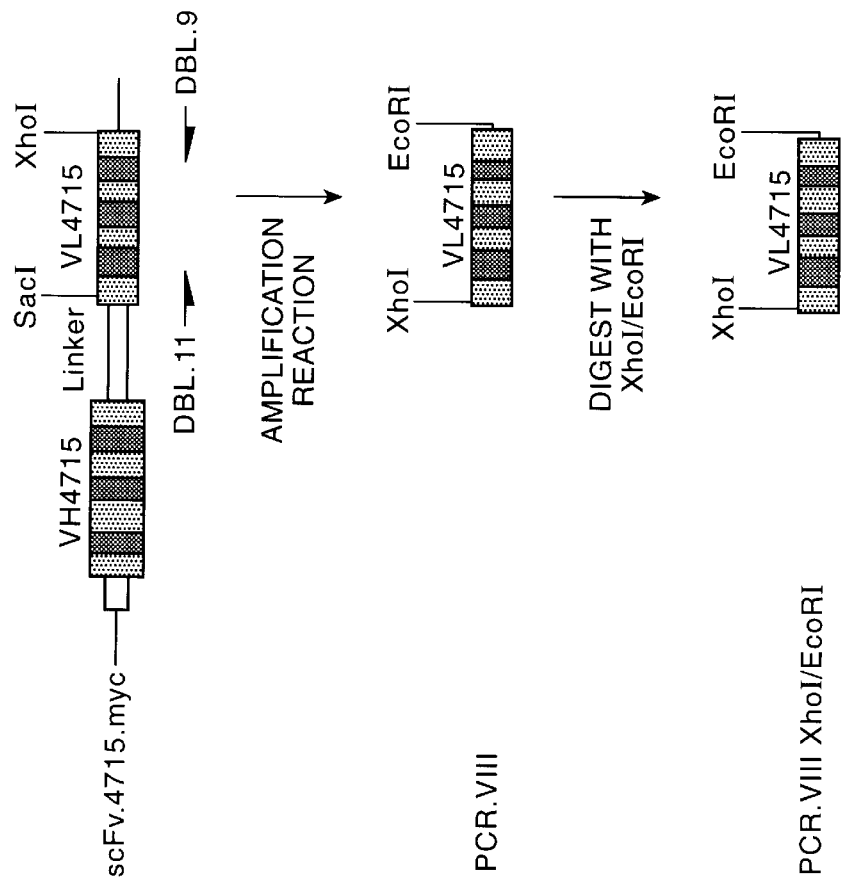
FIG. 26 shows the source of fragment PCR.VIII XhoI/EcoRI.

This plasmid is derived from pGOSA.E (see FIG. 35) from which the (Gly$_4$Ser)$_2$Gly$_4$Val-$V_L$4715 XhoI/EcoRI fragment was excised and replaced by the fragment PCR-VIII XhoI/EcoRI which contains $V_L$.4715 (see FIG. 26). The resulting plasmid pGOSA.S contains $V_H$.4715 linked by the (Gly$_4$Ser)$_3$-AlaGlySerAla linker to $V_H$.3418 plus $V_L$.3418 linked directly to the 5' end of the framework-1 region of $V_L$.4715, thus:

pelB-$V_H$.4715-linkerA-$V_H$.3418+pelB-$V_L$.3418*$V_L$.4715.

pGOSA.T

Figure 36:
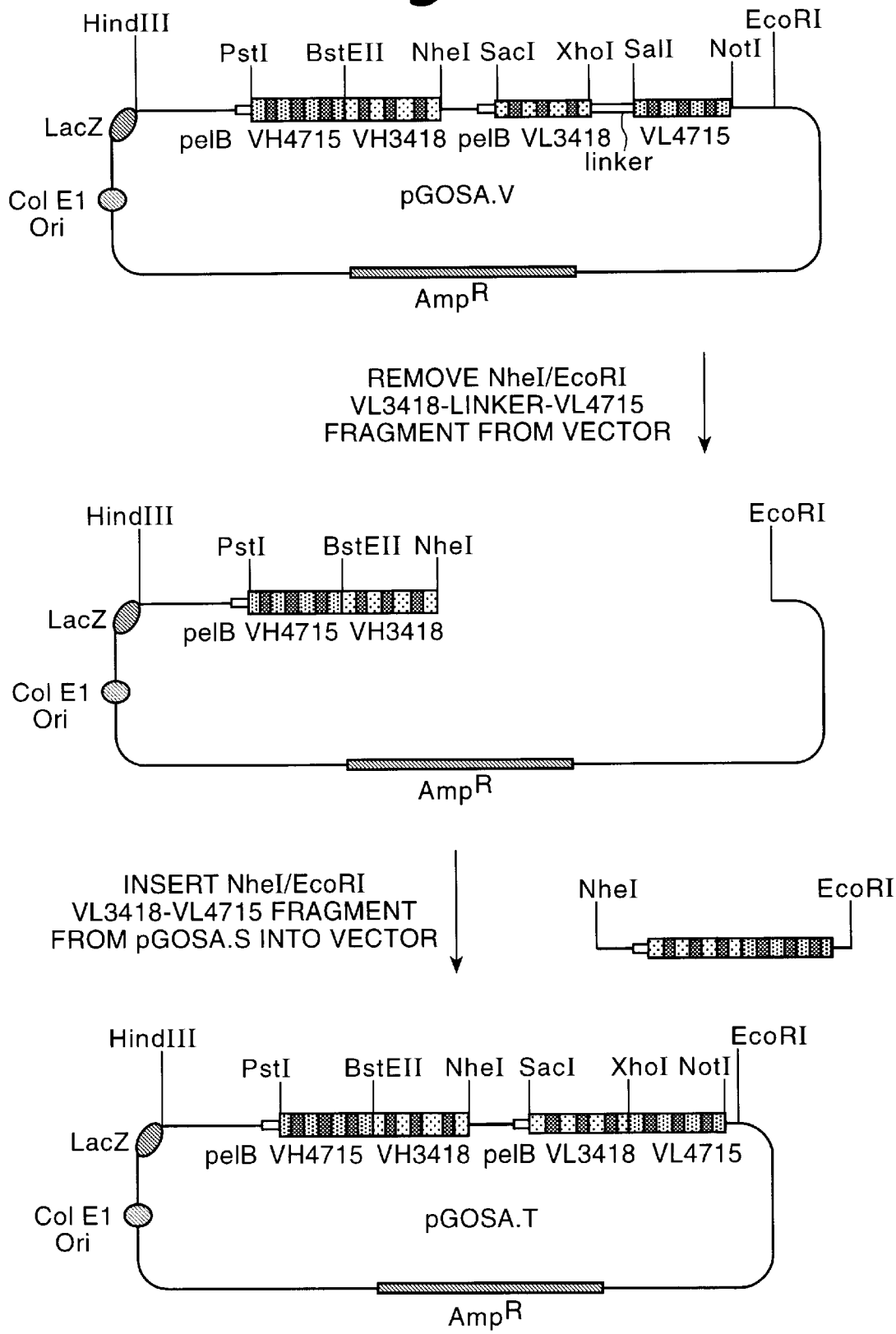
FIG. 36 shows the construction of plasmid PGOSA.T.

This plasmid contains a dicistronic operon consisting of $V_H$.3418 directly to the framework-4 region of $V_H$.4715 plus $V_L$.3418 linked directly to the 5' end of the framework-1 region of $V_L$.4715 (see FIG. 36). Both transcriptional units are preceded by a ribosome binding site and a pelB leader sequence, thus:

pelB-$V_H$.4715*$V_H$.3418+pelB-$V_L$.3418*$V_L$.4715.

This construct was obtained by inserting the NheI/EcoRI fragment of pGOSA.S which contains $V_L$.3418 linked directly to the 5' end of the framework-1 region of $V_L$.4715, into the vector pGOSA.V from which the NheI/EcoRI fragment containing $V_L$.3418 linked by the (Gly$_4$Ser)$_2$Gly$_4$Val linker to $V_L$.4715 was removed.

EXAMPLE 6

Detailed Description of the Preparation of Other Dicistronic Constructs pGOSA.G, and pGOSA.J, pGOSA.Z, PGOSA.AA and PGOSA.AB pGOSA.G

Figure 37B:
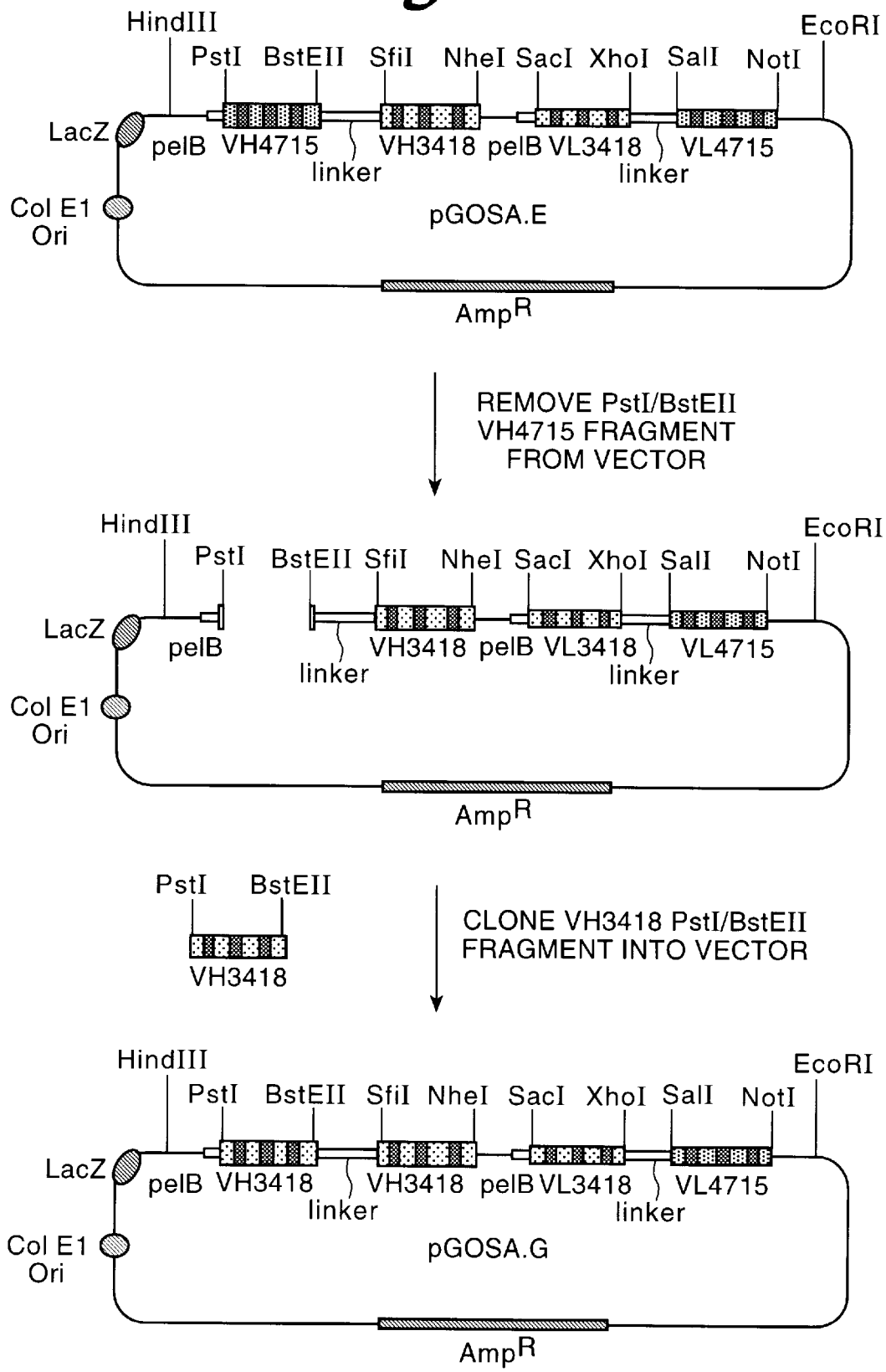
Figure 38:
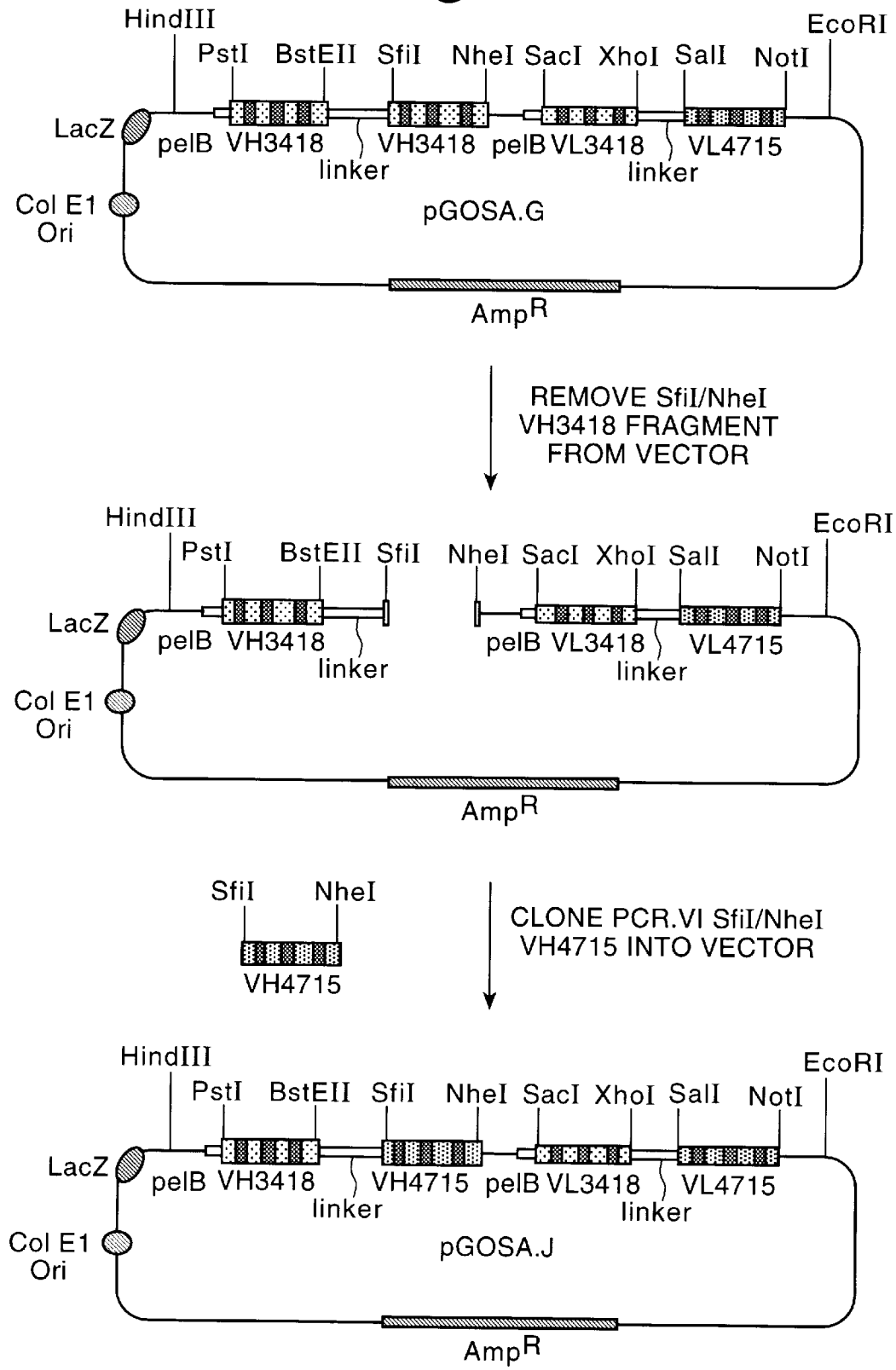
FIG. 38 shows the construction of plasmid pGOSA.J.

This plasmid is an intermediate for the synthesis of pGOSA.J. It is derived from pGOSA.E from which the $V_H$4715 PstI/BstEII fragment has been excised and replaced by the $V_H$3418 PstI/BstEII fragment (excised from Fv.3418). The resulting plasmid pGOSA.G (see FIGS. 37A and 37B) contains two copies of $V_H$.3418 linked by the (Gly$_4$Ser)$_3$AlaGlySerAla linker, plus $V_L$.4715 linked by the (Gly$_4$Ser)$_2$Gly$_4$Val linker to the framework-4 region of $V_L$.3418, thus:

pelB-$V_H$.3418-linkerA-$V_H$.3418+pelB-$V_L$.3418-linkerV-$V_L$.4715.

pGOSA.J

Figure 39:
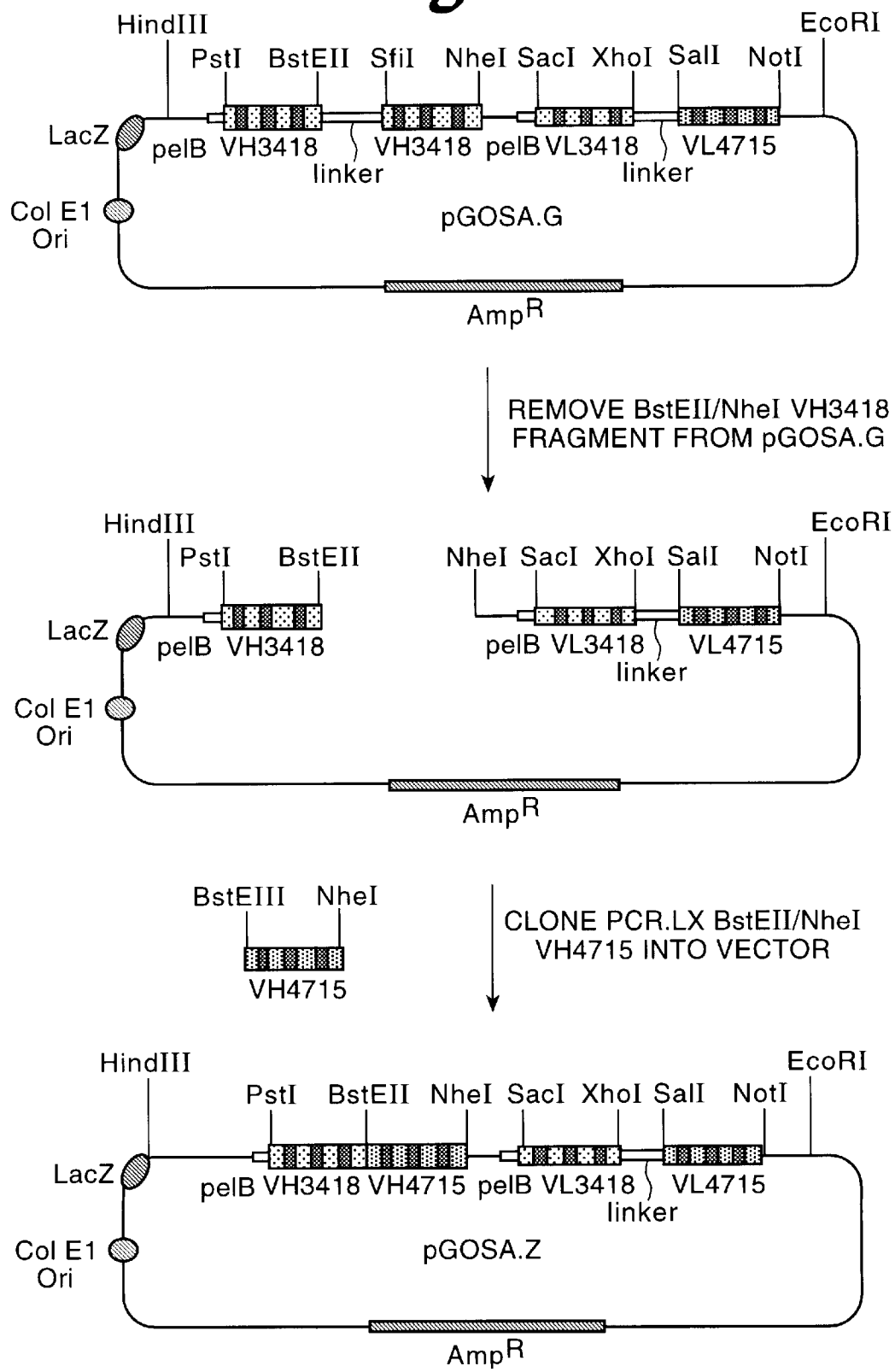
FIG. 39 shows the construction of plasmid pGOSA.Z.

This plasmid contains a dicistronic operon consisting of $V_H$.3418 linked by the (Gly$_4$Ser)$_3$AlaGlySerAla linker to $V_H$.4715 plus $V_L$.3418 linked by the (Gly$_4$Ser)$_2$Gly$_4$Val linker to $V_L$.4715. Both transcriptional units are preceded by a ribosome binding site and a pelB leader sequence (see FIG. 39), thus:

pelB-$V_H$.3418-linkerA-$V_H$.4715+pelB-$V_L$.3418-linkerV-$V_L$.4715.

This construct was obtained by inserting the fragment PCR-VI SfiI/NheI which contains $V_H$4715 (FIG. 24), into the vector pGOSA.G from which the SfiI/NheI $V_H$3418 fragment was removed.

pGOSA.Z

Figure 27:
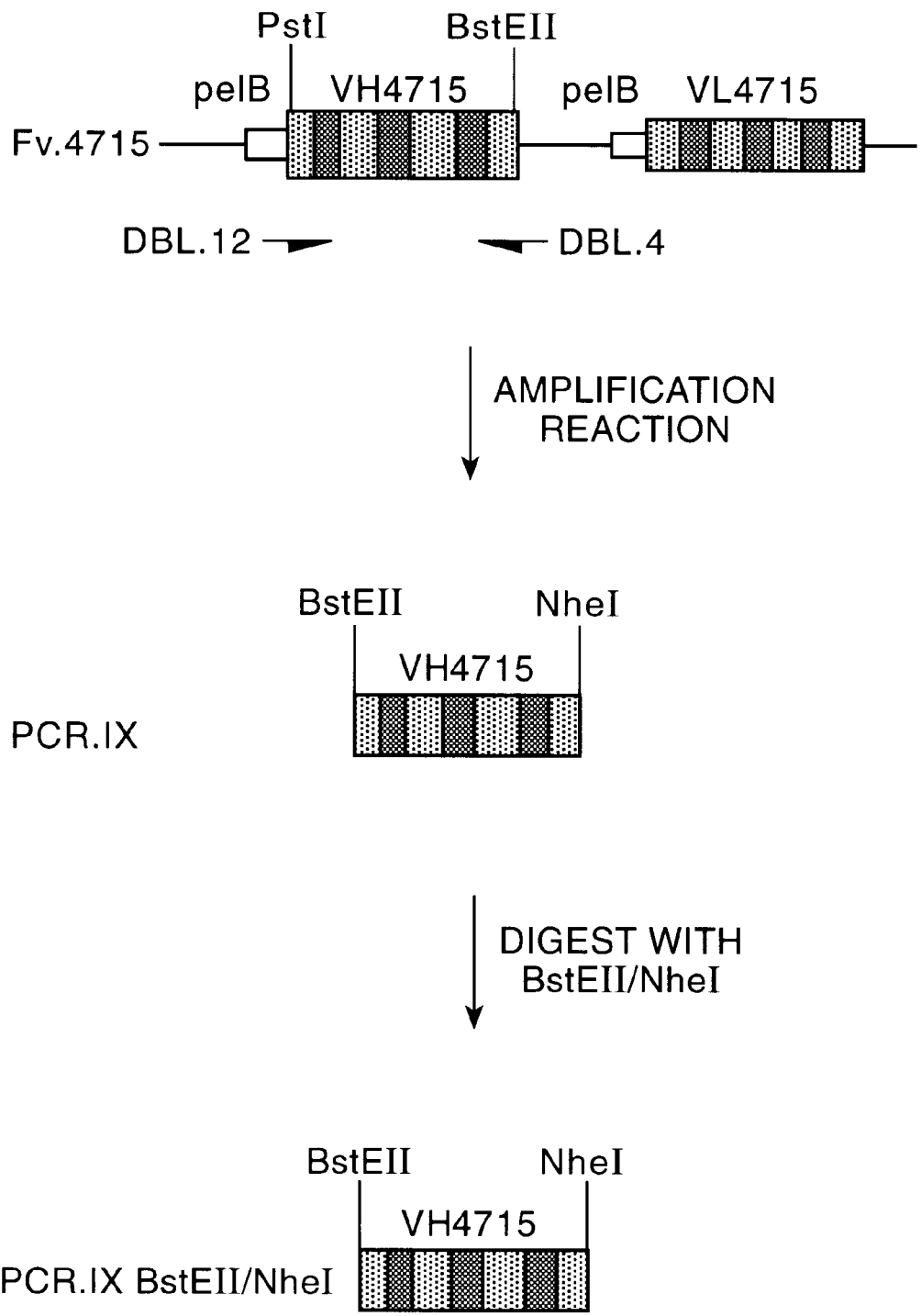
FIG. 27 shows the source of fragment PCR.IX BstEII/NheI.
Figure 28:
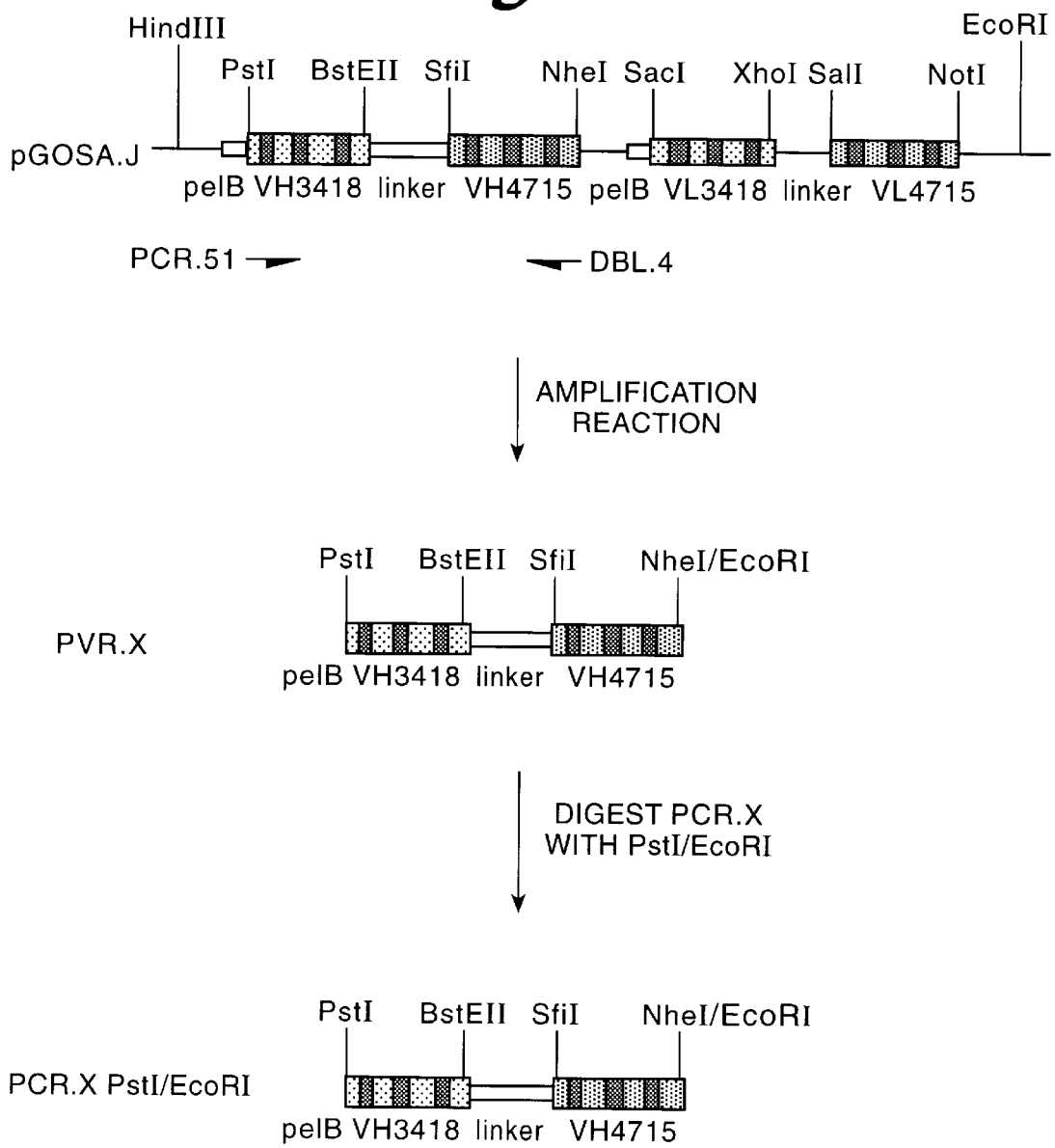
FIG. 28 shows the source of fragment PCR.X PstI/EcoRI.
Figure 29:
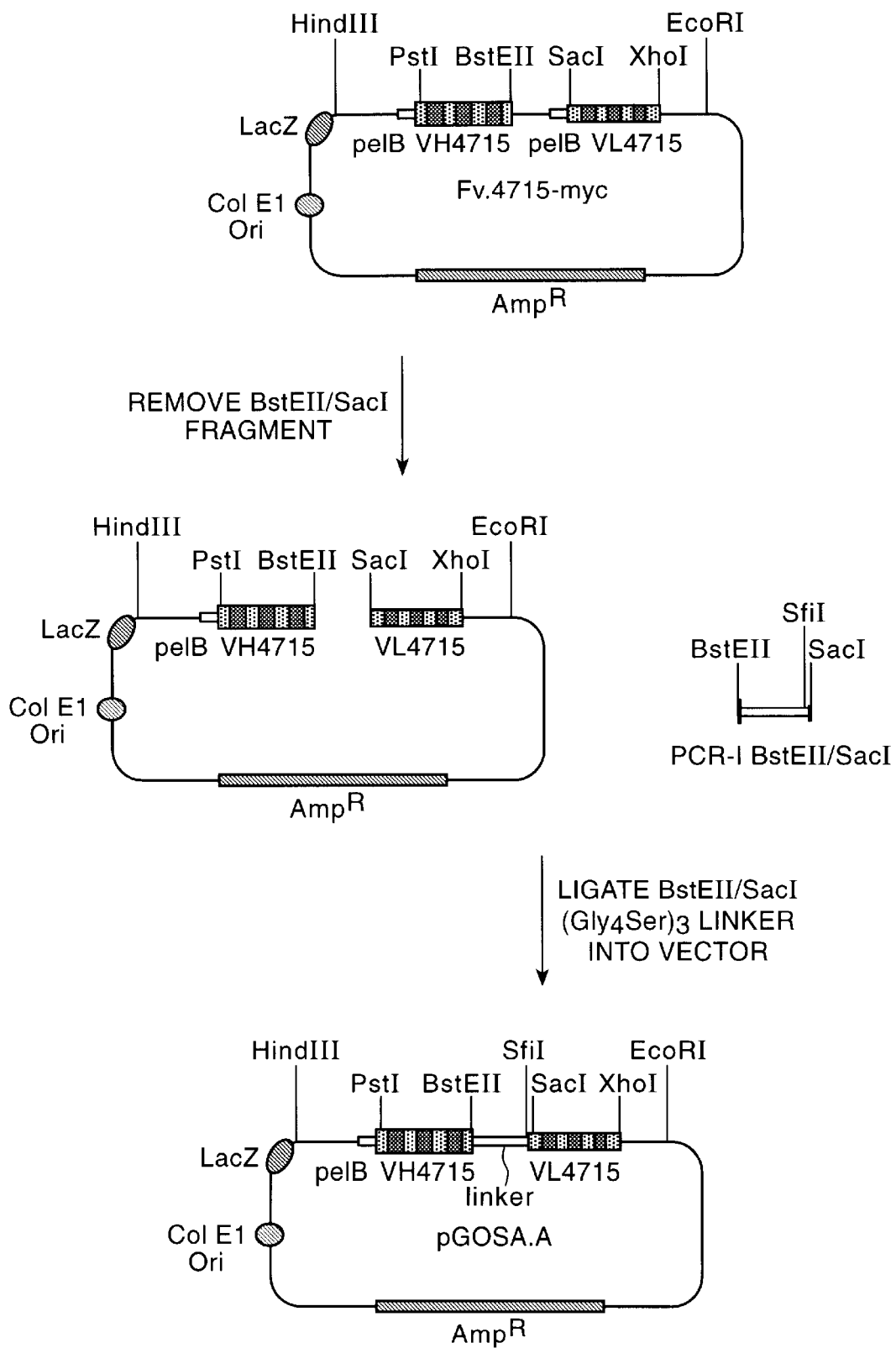
FIG. 29 shows the construction of plasmid pGOSA.A.

This plasmid is derived from PGOSA.G from which the (Gly$_4$Ser)$_3$AlaGlySerAla linker-$V_H$3418 BstEII/NheI fragment was excised and replaced by the fragment PCR-IX BstEII/NheI which contains $V_H$.4715 (FIG. 27). The resulting plasmid pGOSA.Z (see FIG. 39) contains $V_H$.3418 linked directly to the framework-1 region of $V_H$.4715, plus $V_L$.4715 linked by the (Gly$_4$Ser)$_2$Gly$_4$Val linker to the framework-4 region of $V_L$.3418, thus:

pelB-$V_H$.3418*$V_H$.4715+pelB-$V_L$.3418-linkerV-$V_L$.4715

PGOSA.AA

Figure 40:
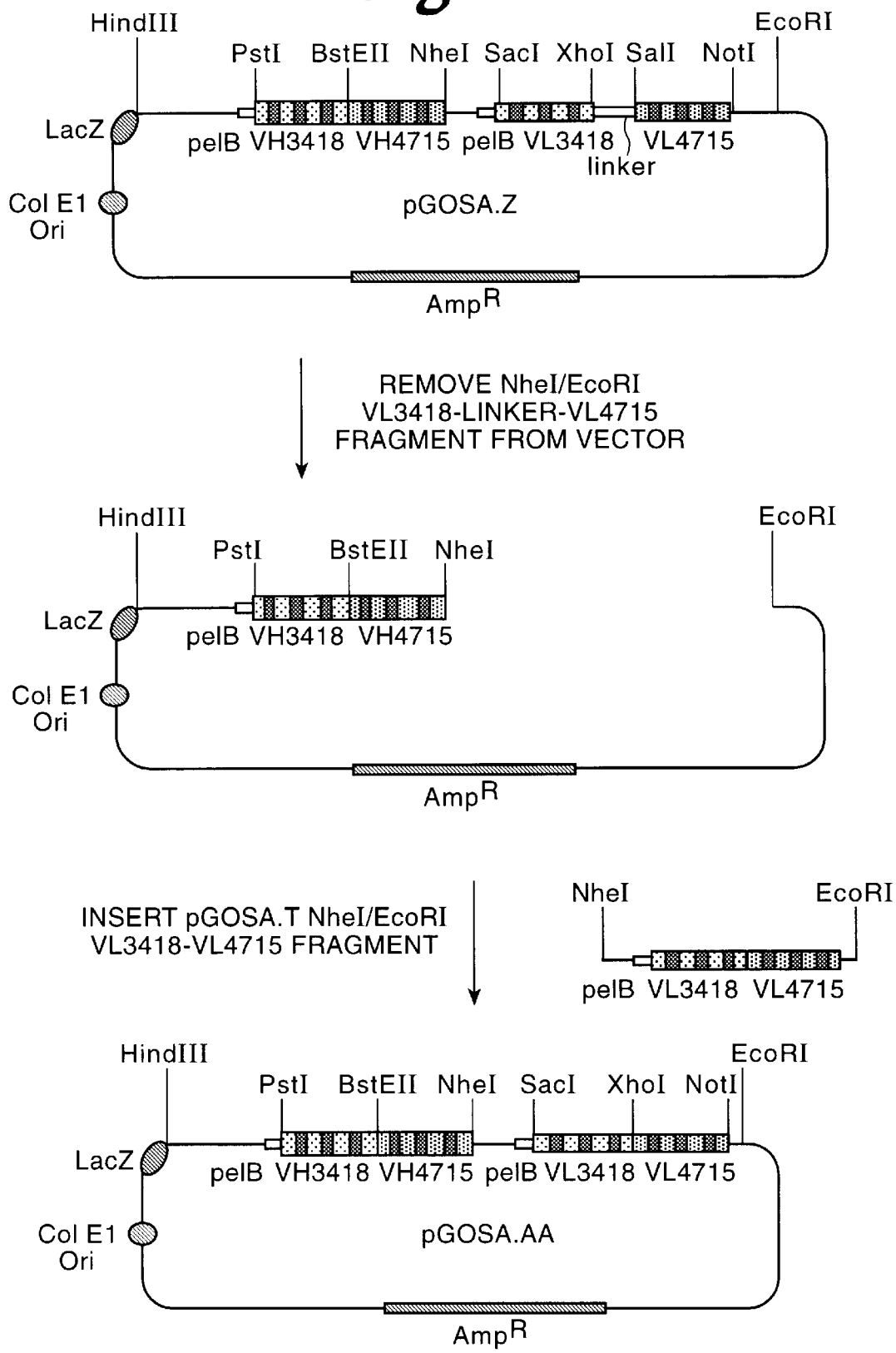
FIG. 40 shows the construction of plasmid pGOSA.AA.

This plasmid contains a dicistronic operon consisting of the $V_H$.3418 linked directly to the 5' end of the framework-1 region of $V_H$.4715 plus $V_L$.3418 linked directly to the 5' end of the framework-1 region of $V_L$.4715. Both transcriptional units are preceded by a ribosome binding site and a pelB leader sequence (see FIG. 40). This construct was obtained by inserting the NheI/EcoRI fragment of PGOSA.T which contains $V_L$.3418 linked directly to the 5' end of the framework-1 region of $V_L$.4715, into the vector pGOSA.Z from which the NheI/EcoRI fragment containing $V_L$.3418 linked by the (Gly$_4$Ser)$_2$Gly$_4$Val linker to $V_L$.4715 was removed, thus:

pelB-$V_H$.3418*$V_H$.4715+pelB-$V_L$.3418*$V_L$.4715 pGOSA.AB

Figure 41:
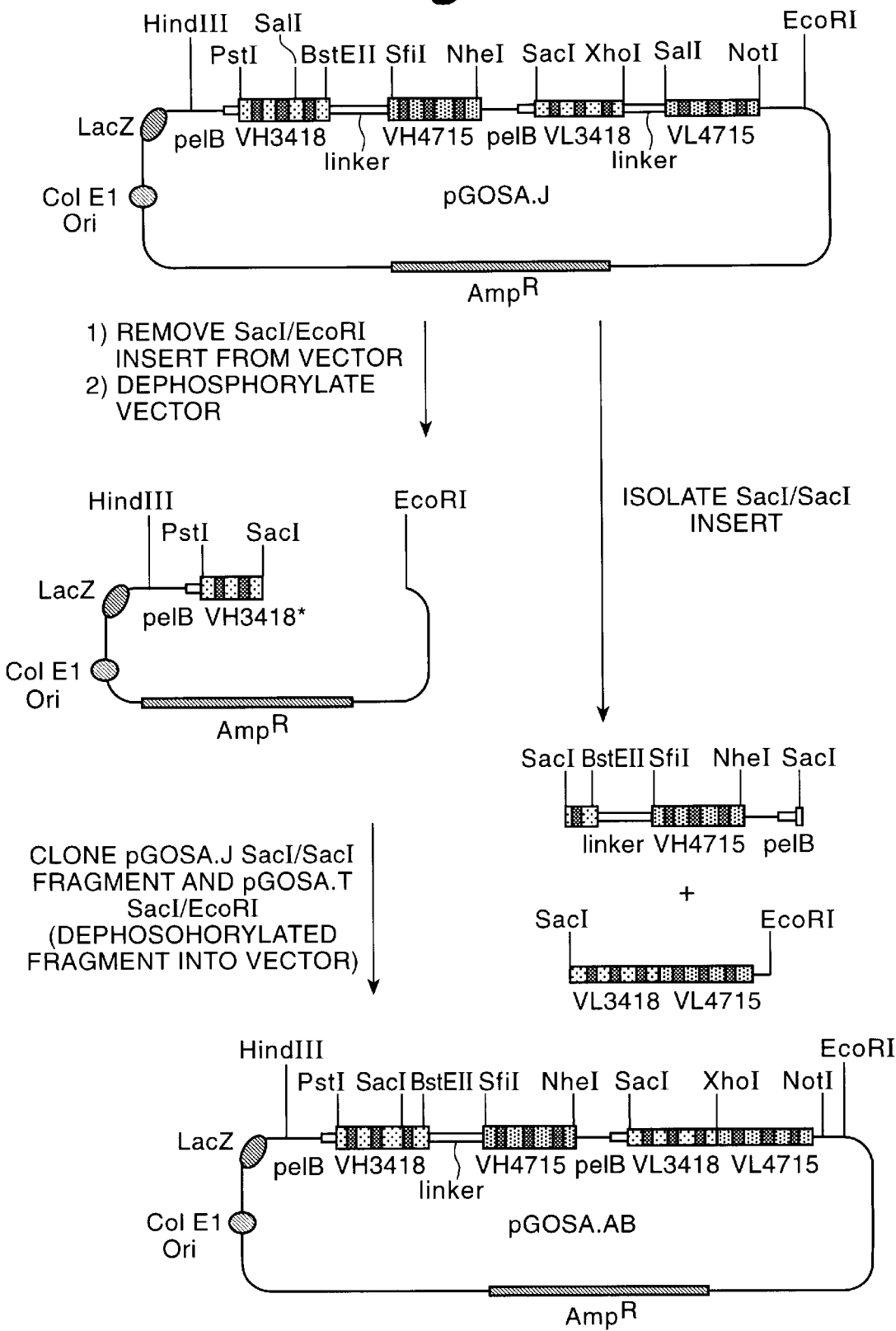
FIG. 41 shows the construction of plasmid pGOSA.AB.

This plasmid is derived from pGOSA.J by a three point ligation reaction (see FIG. 41). The SacI/EcoRI insert, containing part of $V_H$.3418 and the full (Gly4Ser)$_3$AlaGlySerAla linker-$V_H$.4715 and the $V_L$.3418-(Gly$_4$Ser)$_2$Gly$_4$Val-$V_L$.4715 encoding sequences, was removed and replaced by the SacI/SacI pGOSA.J fragment containing the same part of $V_H$.3418 and the full (Gly$_4$Ser)$_3$AlaGlySerAla linker-$V_H$.4715 and the SacI/EcoRI PGOSA.T fragment containing $V_L$.3418 linked directly to the framework-1 region of $V_L$.4715 (see FIG. 36). The resulting plasmid contains $V_H$.3418 linked by the (Gly$_4$Ser)$_3$AlaGlySerAla linker to the 5' end of the framework-1 region of $V_H$.4715 plus $V_L$.3418 linked directly to the 5' end of the framework-1 region of $V_L$.4715, thus:

pelB-$V_H$.3418-linkerA-$V_H$.4715+pelB-$V_L$.3418*$V_L$.4715

EXAMPLE 7

Detailed Description of the Preparation of Monocistronic Constructs pGOSA.L and pGOSA.Y, and pGOSA.C, pGOSA.X. pGOSA.AC and pGOSA.AD pGOSA.L

Figure 42:
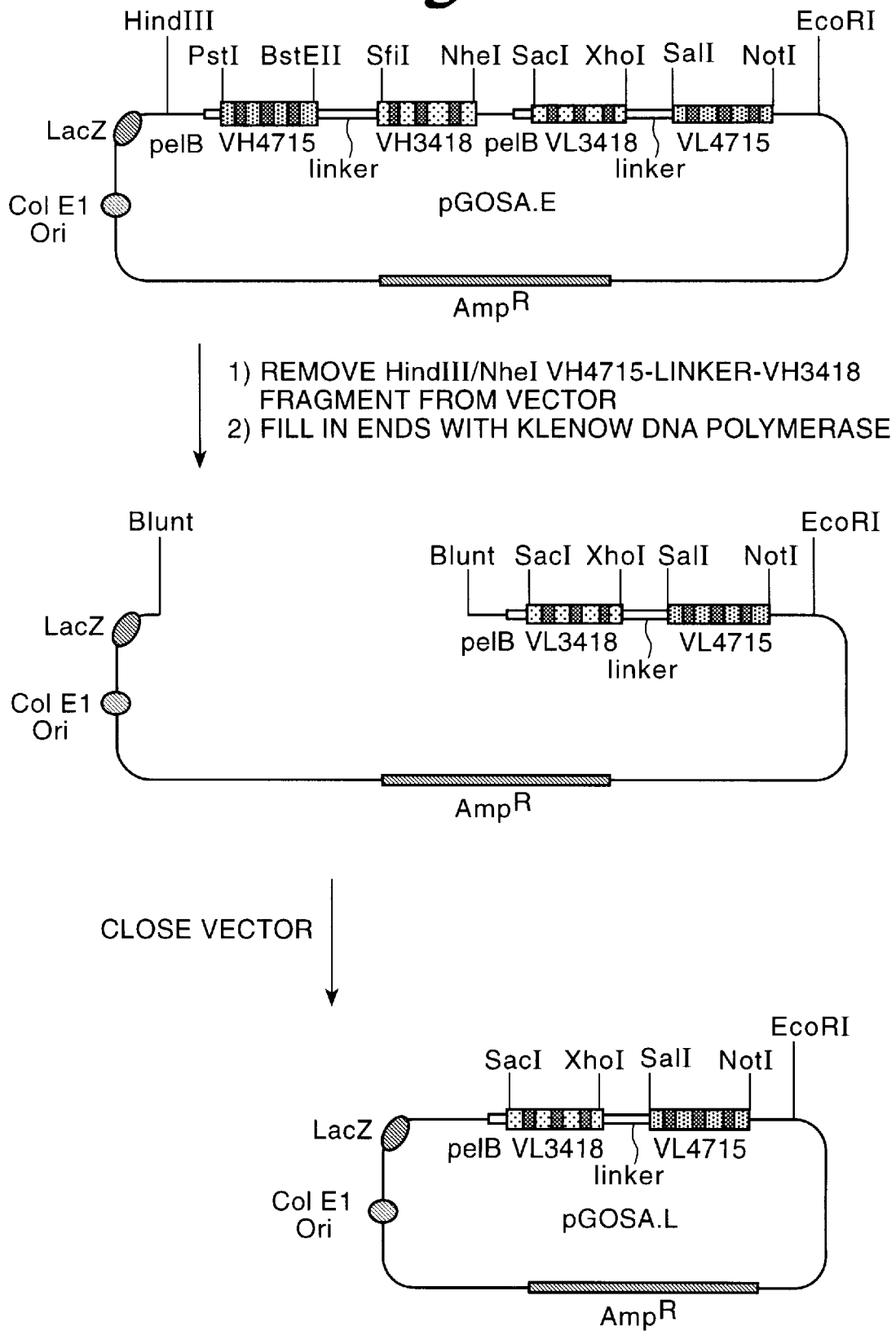
FIG. 42 shows the construction of plasmid PGOSA.L.

This plasmid is derived from pGOSA.E from which the HindIII/NheI fragment containing DNA encoding $V_H$.4715-(Gly$_4$Ser)$_3$AlaGlySerAla-$V_H$.3418 was removed (see FIG. 42). The DNA ends of the vector were made blunt-end using Klenow DNA polymerase and ligated. The resulting plasmid pGOSA.L contains $V_L$.3418 linked by the (Gly$_4$Ser)$_2$Gly$_4$Val linker to the 5' end of the framework-1 region of $V_L$.4715, thus:

pelB-$V_L$.3418-linkerV-$V_L$.4715.

pGOSA.Y

This plasmid is derived from pGOSA.T from which the HindIII/NheI fragment containing DNA encoding $V_H$.4715-$V_H$.3418 was removed (see FIG. 43). The DNA ends of the vector were made blunt-end using Klenow DNA polymerase and ligated. The resulting plasmid pGOSA.Y contains $V_L$.3418 linked directly to 5' end of the framework-1 region of $V_L$.4715, thus:

pelB-$V_L$.3418*$V_L$.4715.

The preparation of pGOSA.C was given in Example 5 above; it can be indicated with: pelB-$V_H$.4715-linkerA-$V_H$.3418.

pGOSA.X

Figure 44:
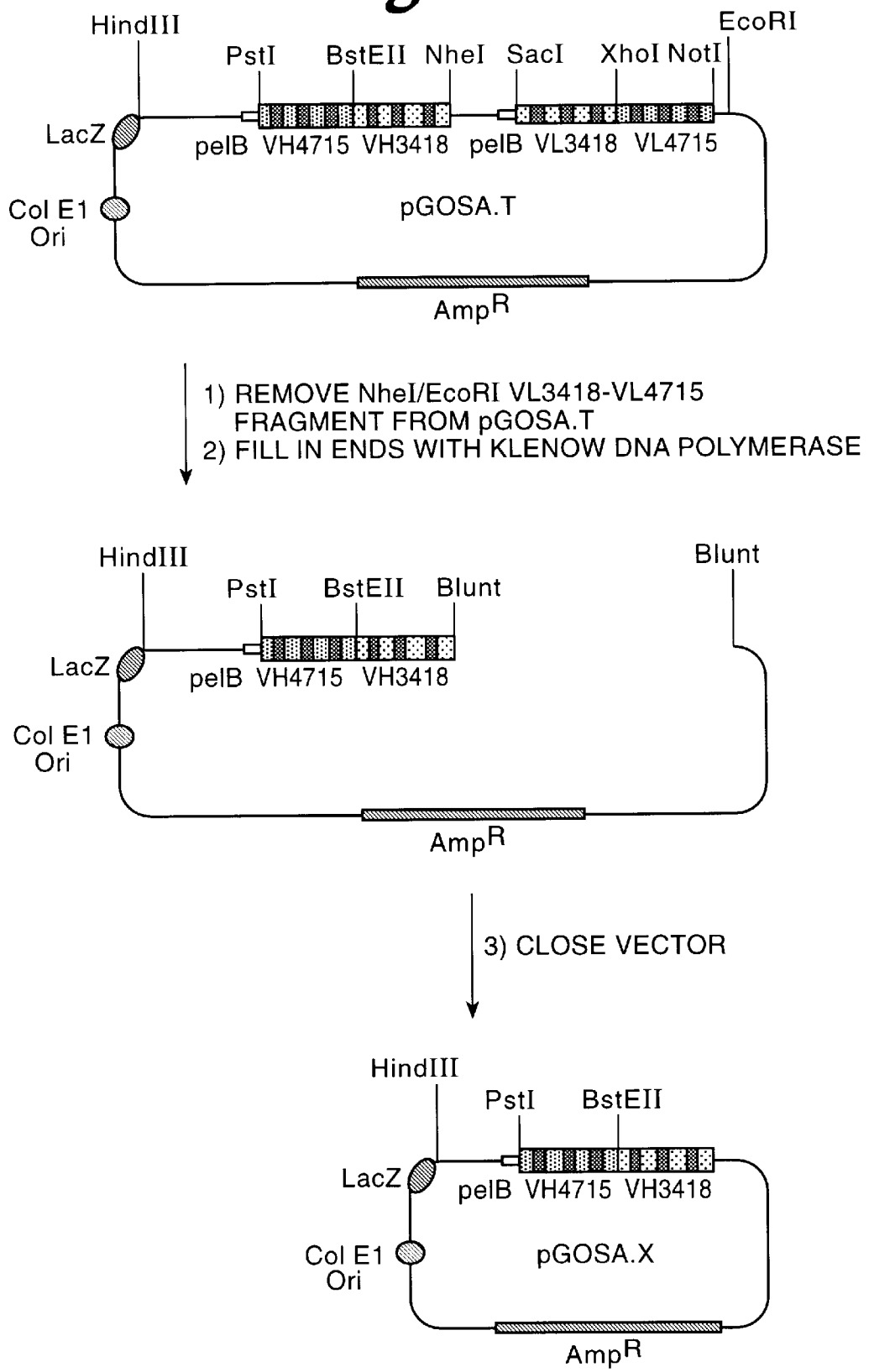
FIG. 44 shows the construction of plasmid pGOSA.X.

This plasmid is derived from pGOSA.T from which the RheI/EcoRI fragment containing DNA encoding $V_L$.3418-$V_L$.4715 was removed. The DNA ends of the vector were made blunt-end using Klenow DNA polymerase and ligated. The resulting plasmid pGOSA.X (see FIG. 44) contains $V_H$.4715 linked directly to 5' end of the framework-1 region of $V_H$.3418, thus: pelB-$V_H$.4715*$V_H$.3418.

pGOSA.AC

Figure 45:
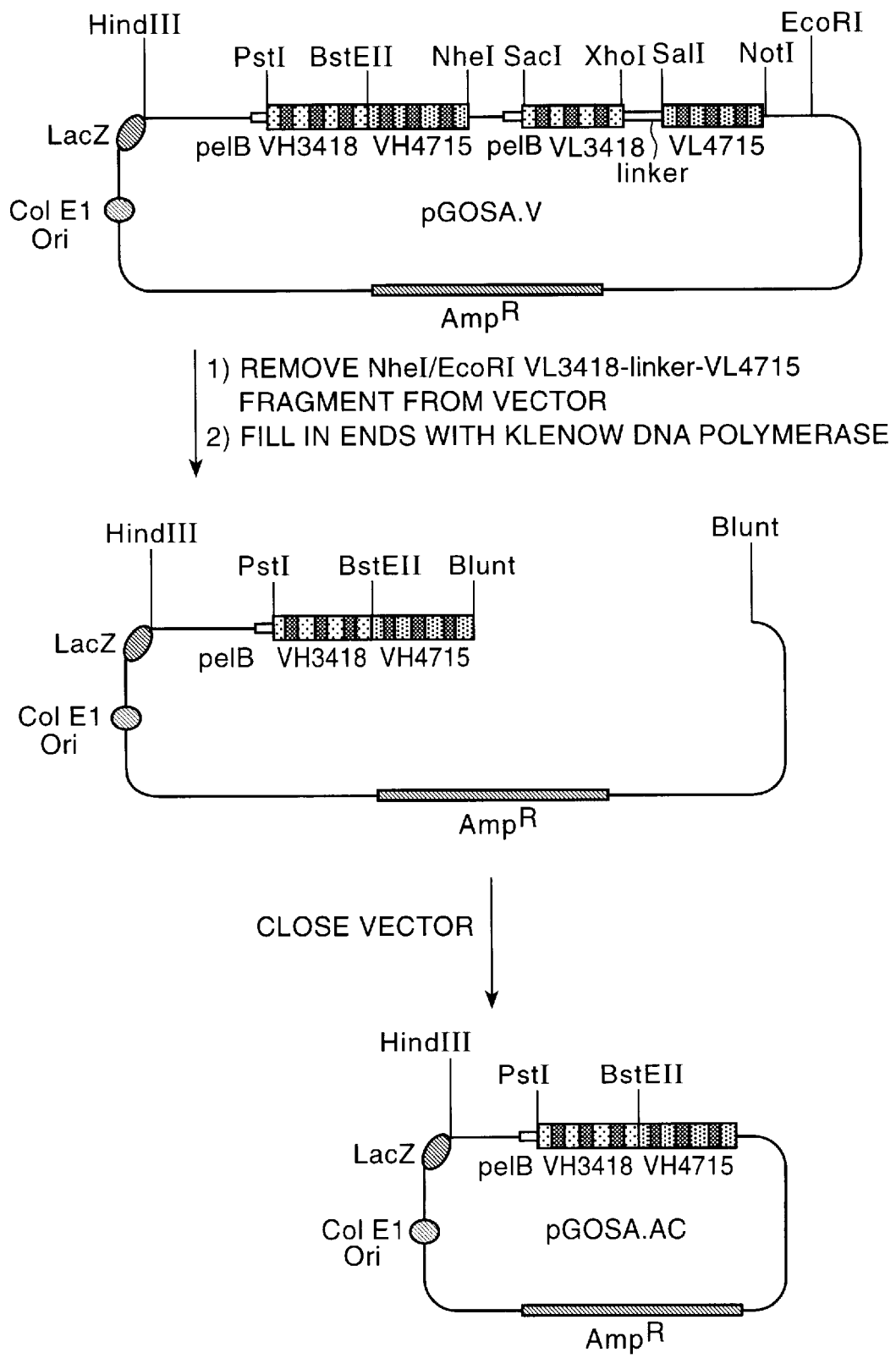
FIG. 45 shows the construction of plasmid pGOSA.AC.

This plasmid is derived from pGOSA.Z from which the NheI/EcoRI fragment containing DNA encoding $V_L$.3418-(Gly$_4$Ser)$_2$Gly$_4$Val-$V_L$.4715 was removed (see FIG. 45). The DNA ends of the vector were made blunt-end using Klenow DNA polymerase and ligated. The resulting plasmid pGOSA.AC contains $V_H$.3418 linked directly to 5' end of the framework-1 region of $V_H$.4715, thus:

pelB-$V_H$.3418*$V_H$.4715.

pGOSA.AD

Figure 46:
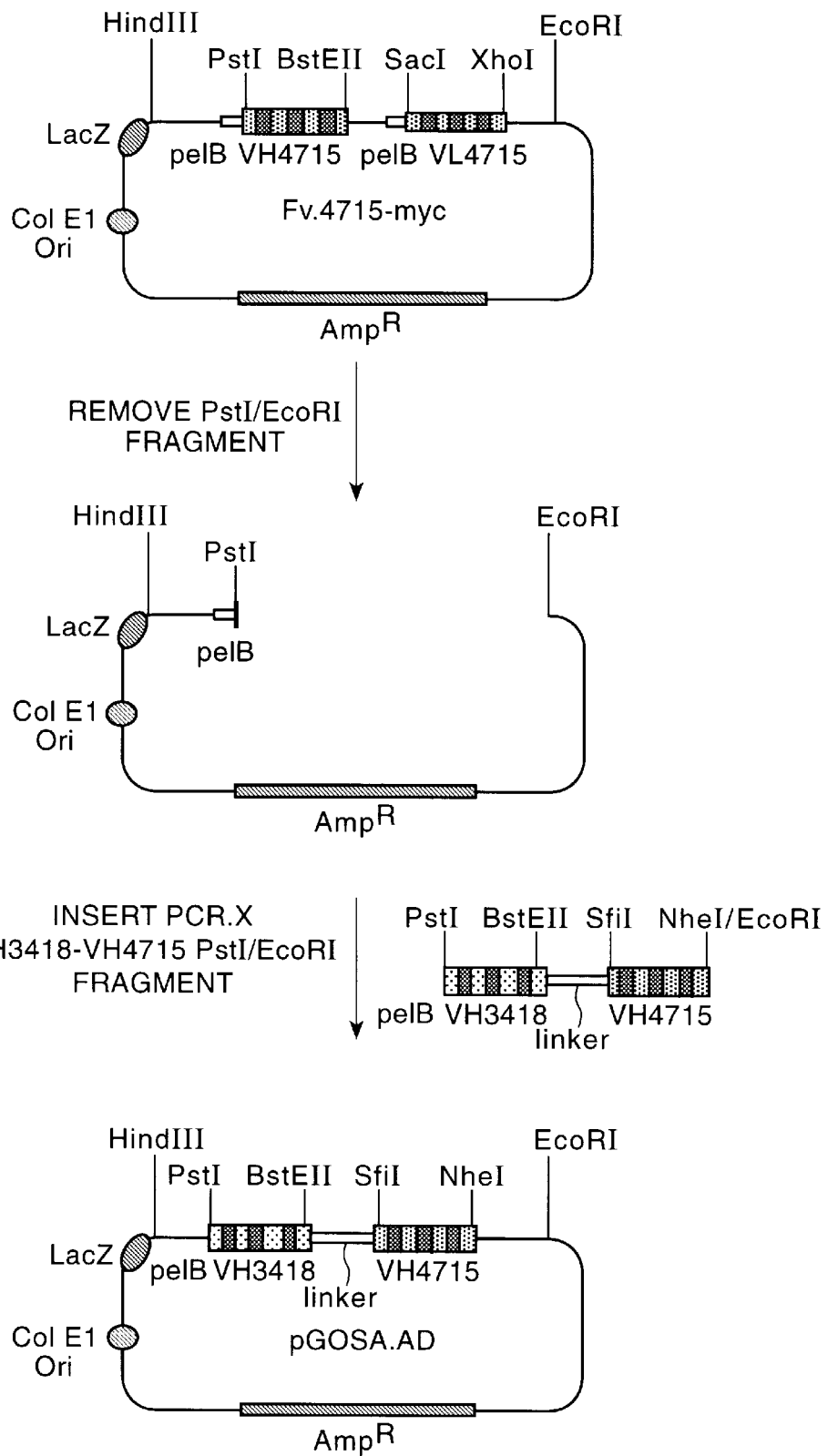
FIG. 46 shows the construction of plasmid pGOSA.AD.

This plasmid was obtained by inserting the PstI/EcoRI PCR.X. fragment containing DNA encoding $V_H$.3418-(Gly$_4$Ser)$_3$AlaGly-SerAla-$V_H$.4715 (see FIG. 28) into the Fv.4715-myc vector from which the PstI/EcoRI Fv.4715-myc insert was removed (see FIG. 46), thus: pelB-$V_H$.3418-linkerA-$V_H$.4715.

These monocistronic constructs can be used to transform the same host with two different plasmids or to transform two different hosts, so that the two $V_H$'s in series can be produced separately from the two $V_L$'s in series.

Evaluation of the Results Obtained

Bifunctional binding activity of GOSA double heads

Figure 12:
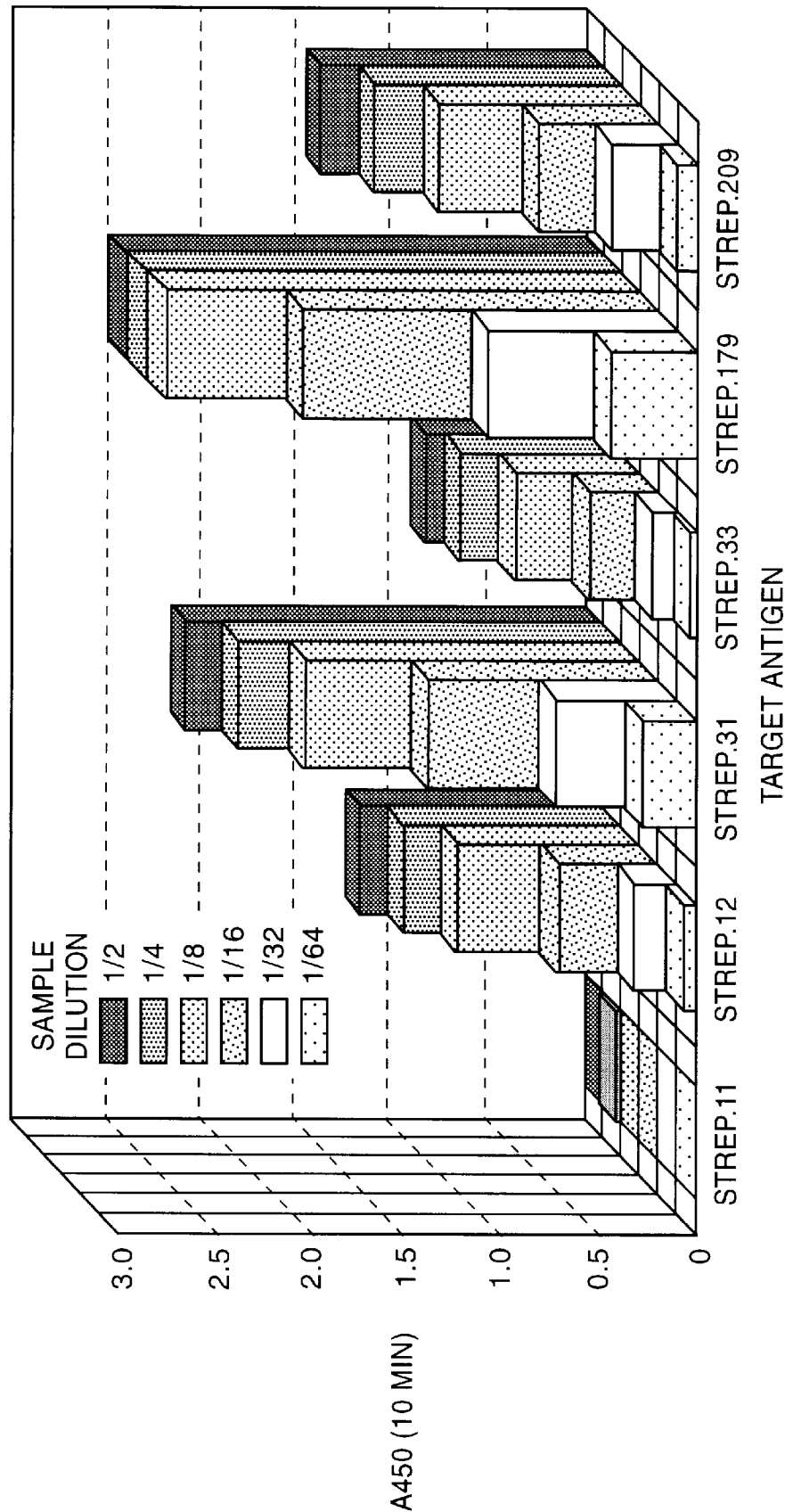
FIG. 12 shows the specificity of glucose oxidase targeting onto the surface of various Streptococcus strains by GOSA.E.
Figure 13:
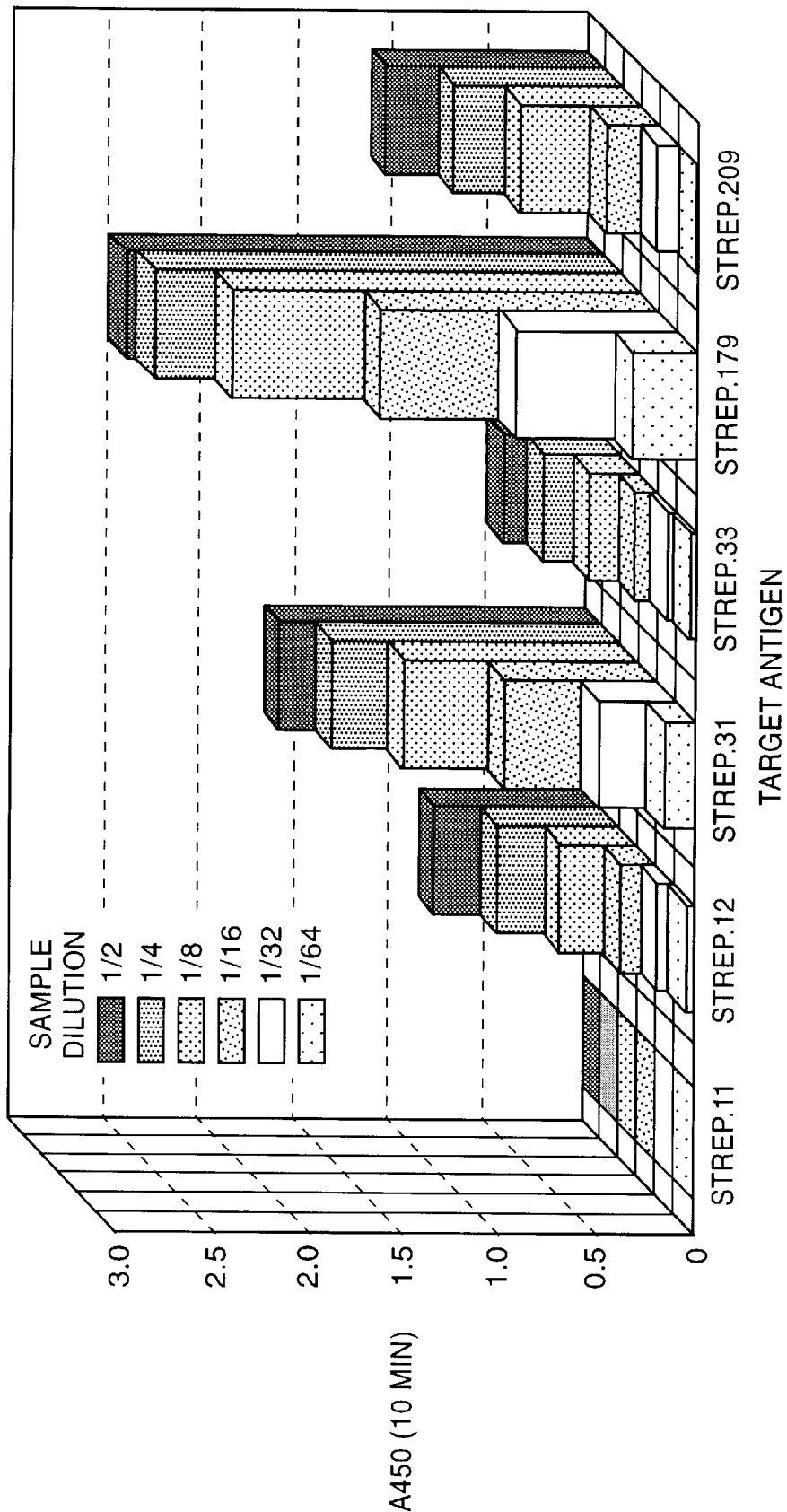
FIG. 13 shows the specificity of glucose oxidase targeting onto the surface of various Streptococcus strains by GOSA.V.
Figure 14:
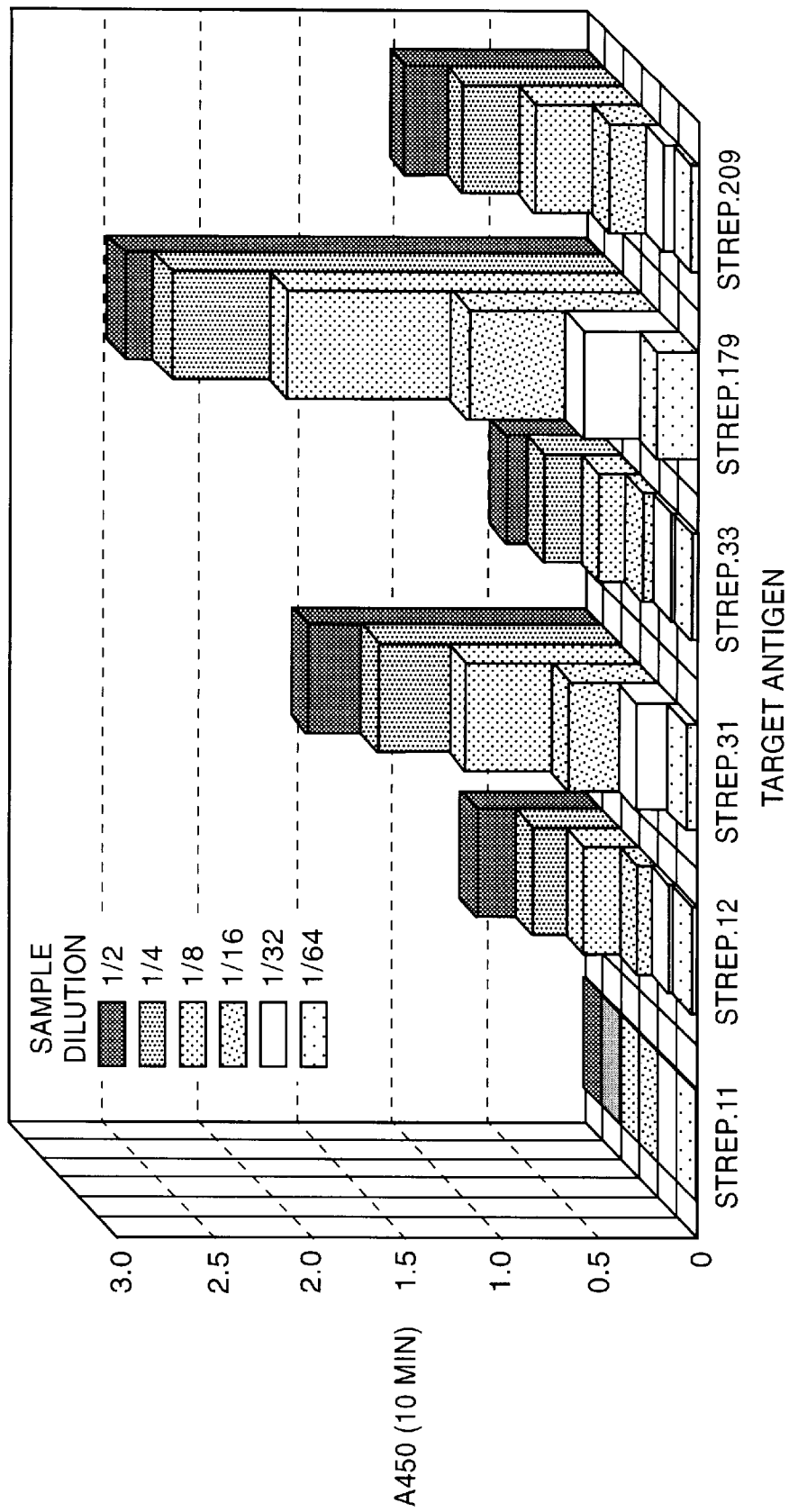
FIG. 14 shows the specificity of glucose oxidase targeting onto the surface of various Streptococcus strains by GOSA.S.
Figure 15:
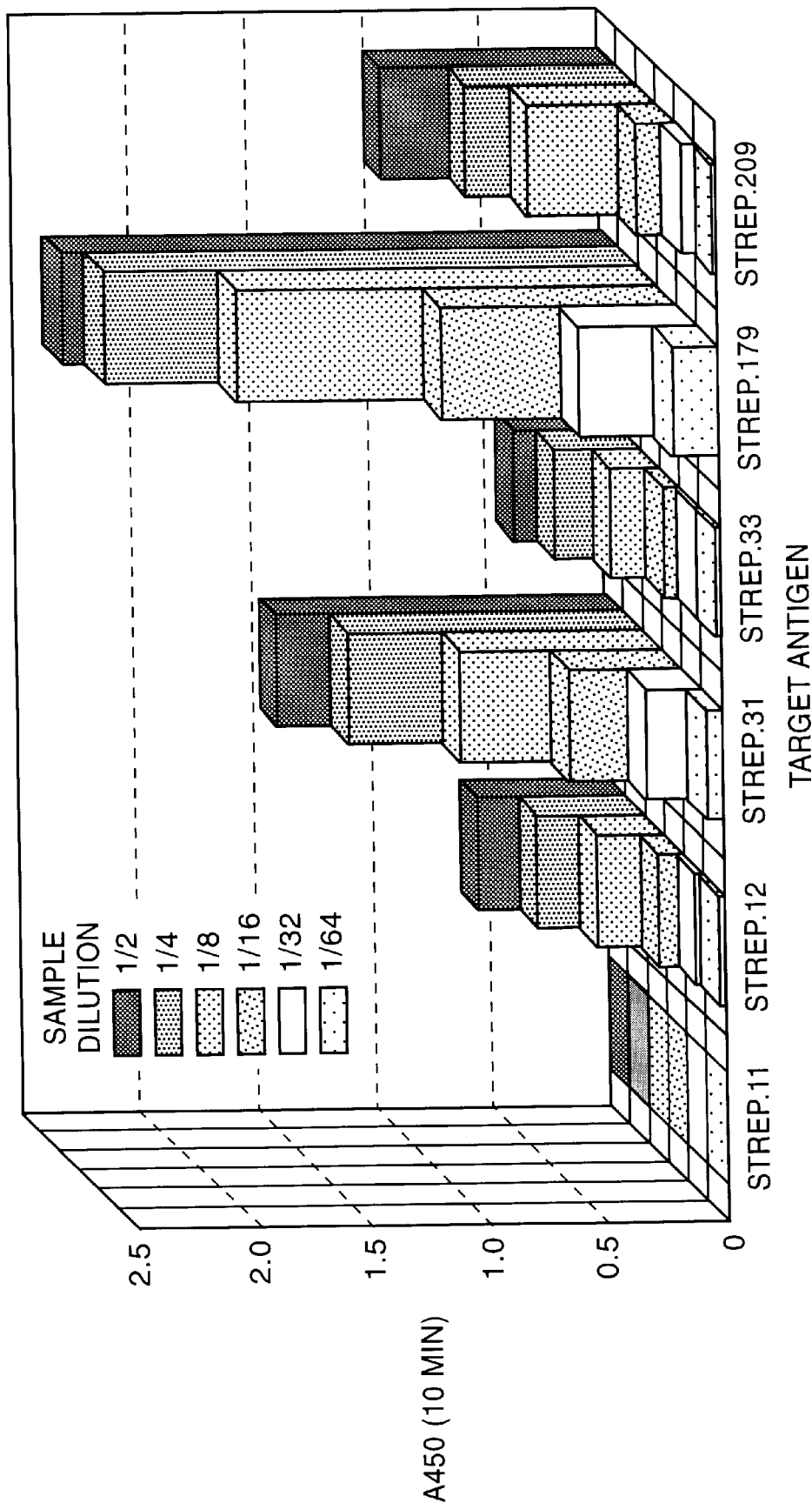
FIG. 15 shows the specificity of glucose oxidase targeting onto the surface of various Streptococcus strains by GOSA.T.

In this specification the construction of a two chain protein complex is described, in which one of the chains consists of two heavy chain V-domains and the other chain consists of the two corresponding light chain V-domains. The variable domains are linked either directly or through a polypeptide linker. In this specification evidence is provided that these type of molecules ("double heads") contain both antigen binding specificities of the Fv's used to generate these multi-functional antibody fragments. FIG. 12 shows that GOSA.E can be used to specifically target the enzyme glucose oxidase to several Streptococcus sanguis strains, using antibody fragments derived from hybridomas expressing antibodies directed against these antigens. FIG. 12 further shows that the fine specificity of the anti-Streptococcus sanguis scFv 4715 is preserved in the GOSA.E double head.

Effect of Linkers and Relative Position of V-domains on Double Head Activity After it was shown that the "cross-over double-head" approach ($V_HA-V_HB+V_LB-V_LA$) yields active bispecific molecules, the importance of the relative position of the V-domains in these constructs was investigated. Both possible positional orientations (GOSA.E=$V_H$A-LinkerA-$V_H$B+$V_L$B-LinkerV-$V_L$A and GOSA.J=$V_H$B-LinkerA-$V_H$A+$V_L$B-LinkerV-$V_L$A) were constructed and tested for bispecific activity, despite the suggestion obtained by molecular modelling that the binding site formed by the second (downstream/C-terminal) V-domains in the configuration $V_HB-V_HA+V_LB-V_LA$ (GOSA.J) was in an unfavourable position for binding to large protein antigens on the surface of cells. Surprisingly however, it was found experimentally that the downstream binding site is in fact accessible. Although the relative position of the heavy chains and the light chains was found to have an effect on the observed reactivity both tested combinations show bispecific activity with the "cross-over" combination (GOSA.E=$V_HA-V_HB+V_LB-V_LA$) exhibiting a higher level of reactivity compared to the combination $V_HB-V_LA+V_LB-V_L$(=GOSA.J) as demonstrated for A=anti-Strep and B=anti-Gox.

Molecular modelling of the $V_HB-V_HA+V_LB-V_LA$ (=GOSA.J) configuration further suggested that, only when the connecting linkers are kept long enough (to span 30 to 35 Å), the protein chains could fold such that both binding sites are fully accessible.

The "cross-over" configuration: $V_HA-V_HB+V_LB-V_LA$ (GOSA.E) wherein linker length was not critical, was predicted to result in a complex with both binding sites facing in opposite directions, without the restraints suggested for the configuration $V_HB-V_HA+V_LB-V_LA$ (GOSA.J). Removing the flexible polypeptide linker from the $V_HA-V_HB$ chain only had a minimal effect on the ability of the double head in the "cross-over" configuration (GOSA.V=$V_HA*V_HB+V_LB-V_LA$) to bind both S. sanguis and Glucose oxidase. However, removing the flexible polypeptide linker from the $V_HB-V_HA$ chain from the molecule in the $V_HB-V_HA+V_LB-V_LA$ configuration (GOSA.Z =$V_HB*V_HA+V_LB-V_LA$) resulted in a dramatic reduction of its ability to bind both S. sanguis and Glucose oxidase.

In contrast with the double head in the "cross-over" configuration without the flexible polypeptide linker between the two heavy chain domains (GOSA.V), where molecular modelling predicted the resulting molecule to be active, removal of the flexible linker from the $V_LB-V_LA$ chain could not be modelled such that both binding sites were fully accessible. ELISA results confirm that the double head in the $V_HB-V_HA+V_LB-V_LA$ configuration without a linker between the two light chain domains (GOSA.AB) exhibits only minimal S. sanguis and glucose oxidase binding activity. Surprisingly, deletion of the flexible linker from the $V_LB-V_LA$ chain from the double head in the "cross-over" configuration (GOSA.S) only had a small effect on the bispecific activity of the resulting molecule. As expected from the molecular modelling results from the double heads without a flexible linker between the two light chain domains, removal of both the flexible polypeptide linkers from the double head molecules, could not be modelled such that both binding sites were fully accessible. In agreement with the ELISA results obtained with the GOSA.AB construct, the double head in the $V_HB-V_HA+V_LB-V_LA$ configuration without any linkers (GOSA.AA) only exhibits minimal if any S. sanguis and glucose oxidase binding activity. Surprisingly, the double head in the "cross-over" configuration without any linkers (GOSA.T=$V_HA*V_HB+V_LB*V_LA$) still exhibited 25–50% of S. sanguis and glucose oxidase bispecific binding activity when compared to the activity of the double head in the "cross-over" configuration with two linkers (GOSA.E).

Thus the conclusion of this work is that modelling can give some indications, but that the computer programmes cannot predict what is possible and what not. Several deviations from the modelling expectations were found. With a paraphrase on an old saying: theories are nice but the experiment is the ultimate proof.

Sensitivity of GOSA Double Heads

Using an ELISA format it was shown that the sensitivity of the GOSA.E double head is as least as a sensitive as an IgG-glucose oxidase conjugate, as determined by the lowest concentration of Streptococcus sanguis antigen immobilised on a solid phase that is still detectable.

GOSA Double Heads Are Produced as Dimers

Figure 16:
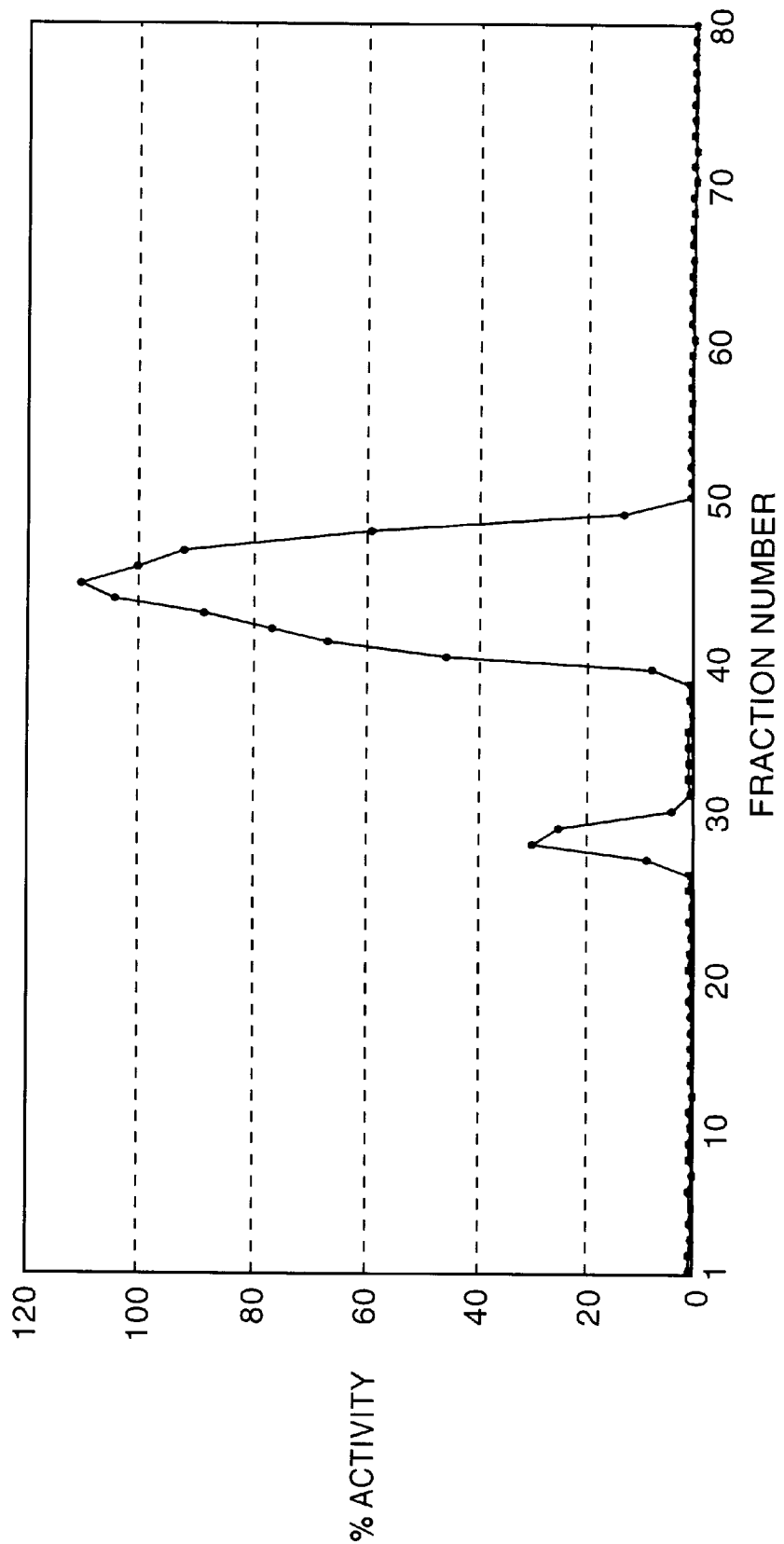
FIG. 16 shows the results of an ELISA. Individual fractions of a gelfiltration experiment using partially purified GOSA.E as feedstock were tested for glucose oxidase and *Streptococcus sanguis* bispecific binding activity.
Figure 17:
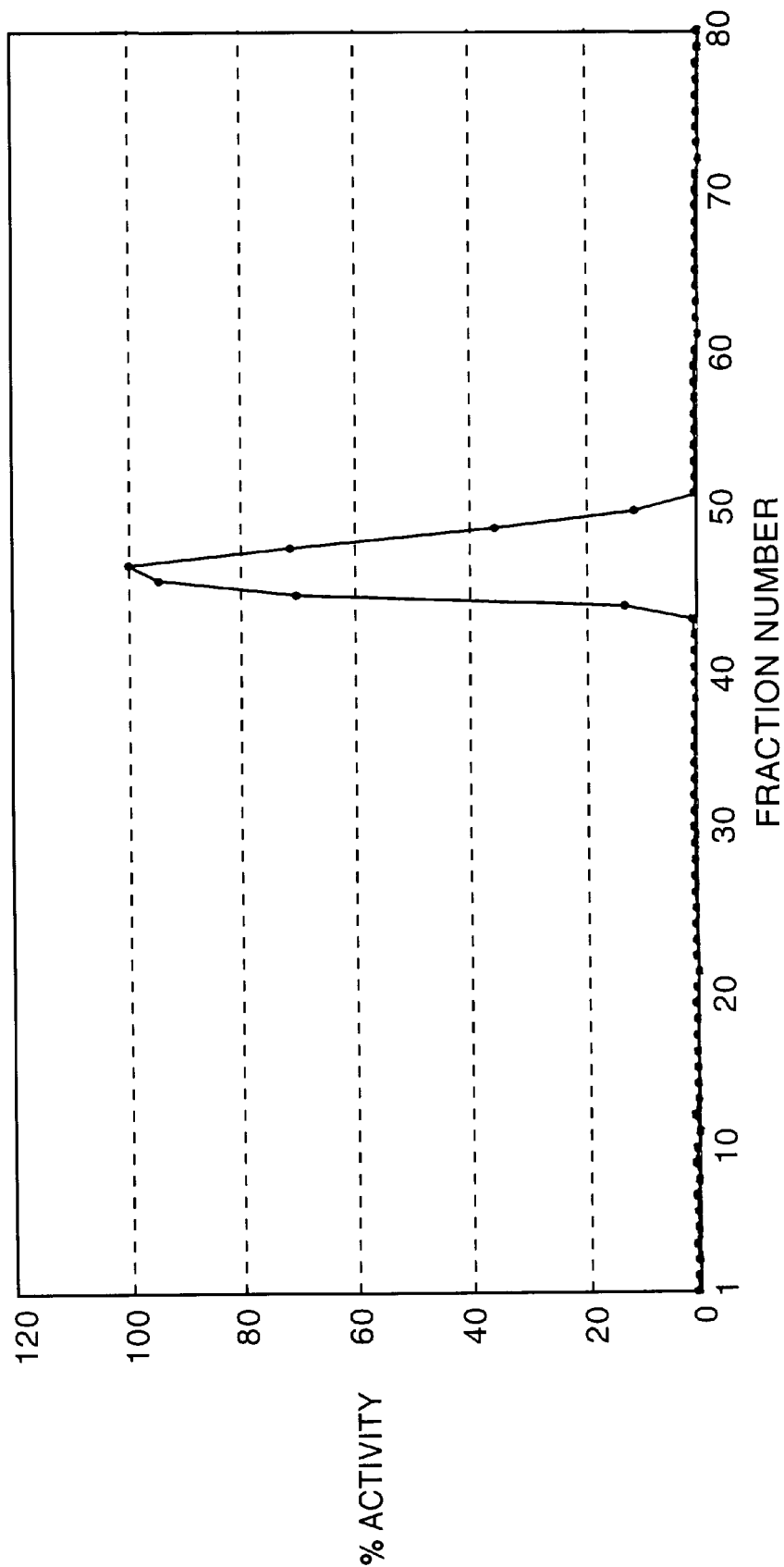
FIG. 17 shows the results of an ELISA. Individual fractions of a gelfiltration experiment using partially purified GOSA.V as feedstock were tested for glucose oxidase and *Streptococcus sanguis* bispecific binding activity.
Figure 18:
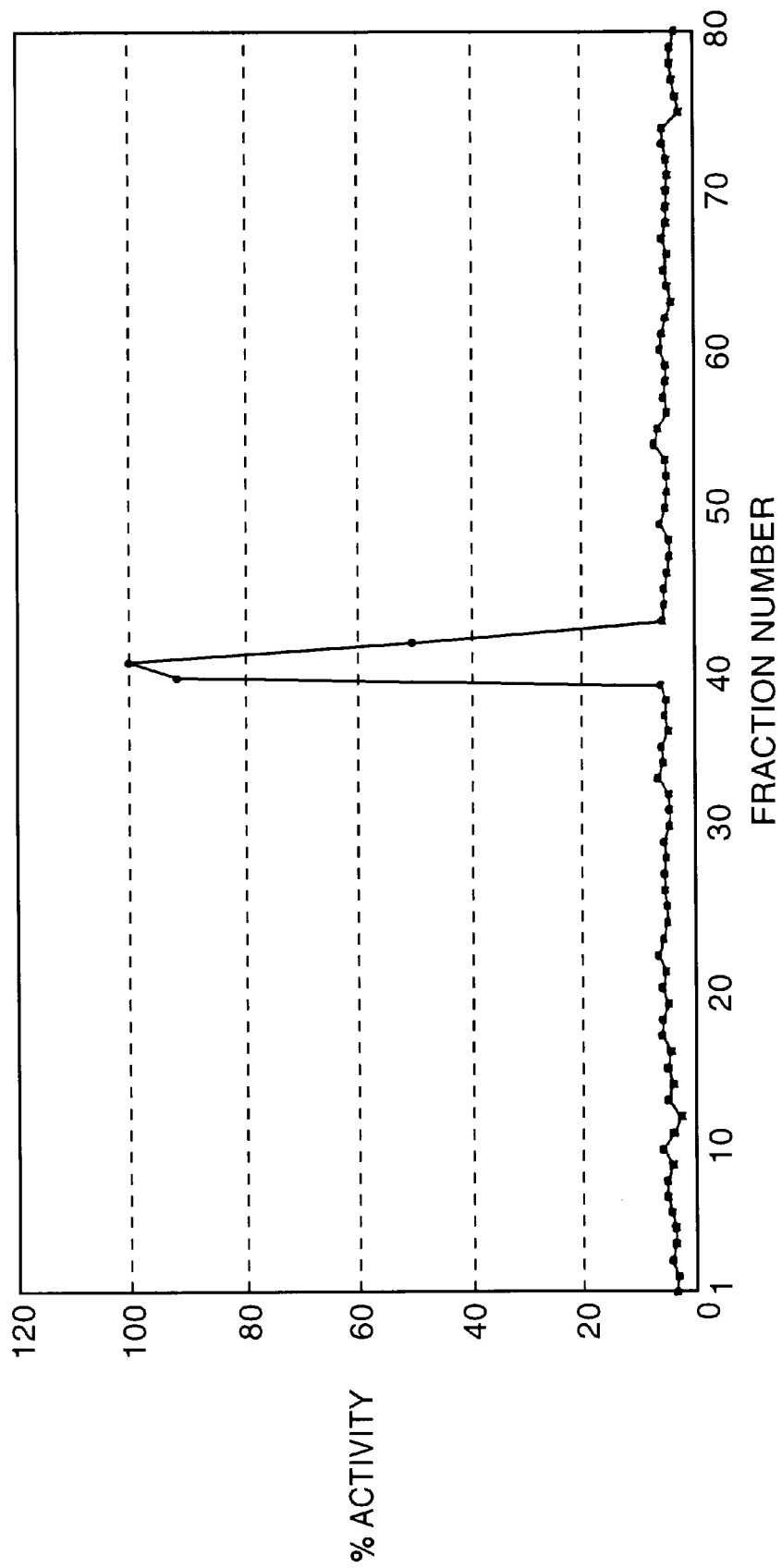
FIG. 18 shows the results of an ELISA. Individual fractions of a gelfiltration experiment using partially purified GOSA.T as feedstock were tested for glucose oxidase and *Streptococcus sanguis* bispecific binding activity.

FPLC analysis of partially affinity-purified GOSA.E, GOSA.V, GOSA.S and GOSA.T samples usually gave only one GOSA double head activity peak as determined by ELISA (FIGS. 16–18). The position of this peak in the elution pattern indicated that the molecular weight of the GOSA double head is 40–50 kD. Since this molecular weight corresponds to the expected molecular weight of the $V_H2+V_L2$ double head dimer, it was concluded that GOSA.E, GOSA.V, GOSA.S and GOSA.T are primarily produced as dimeric molecules. Occasionally an activity peak with an apparent molecular weight of ≈200 kD was observed (FIG. 16). The presence of glucose oxidase activity in these fractions indicate that these fractions contain GOSA double head complexed with glucose oxidase.

In Vitro Assembly of GOSA Double Heads

It was shown that bifunctionally active dimeric GOSA molecules together in one cell can be produced by translation from one dicistronic messenger (GOSA.E, GOSA.S, GOSA.T, GOSA.V, GOSA.J, GOSA.AB, GOSA.AA and GOSA.Z). In addition high levels of S. sanguis and glucose oxidase bispecific binding activity is formed when supernatants of cultures producing the separate GOSA subunits are mixed (see Example 7). The effects of linkers and the relative position of the individual $V_H$-domains on the S. sanquis and glucose oxidase bispecific binding activity observed in these mixing experiments are comparable to the dicistronic constructs.

The constructs described above are summarised in Table 2 below.

Table 2A describes intermediate constructs that were not further tested.

Table 2B describes the dicistronic constructs.

Table 2C describes the monocistronic constructs.

(LiA) stands for the $V_H$—$V_H$ linker (Gly$_4$Ser)$_3$AlaGlySerAla (=linkerA)

(LiV) stands for the $V_L$—$V_L$ linker (Gly$_4$Ser)$_2$Gly$_4$Val (=linkerV)

TABLE 2

Table 2A

| | |
|---|---|
| GOSA.A: | $V_H.4715$-LiA-(SfiI)-$V_L.4715$-myc |
| GOSA.B: | $V_H.3418$-LiV-$V_L.3418$-(SalI/EcoRI) |
| GOSA.D: | $V_H.3418 + V_L.3418$-LiV-$V_L.4715$ |
| GOSA.G: | $V_H.3418$-LiA-$V_H.3418 + V_L.3418$-LiV-$V_L.4715$ |

Table 2B

| | |
|---|---|
| GOSA.E: | $V_H.4715$-LiA-$V_H.3418 + V_L.3418$-LiV-$V_L.4715$ |
| GOSA.S: | $V_H.4715$-LiA-$V_H.3418 + V_L.3418*V_L.4715$ |
| GOSA.T: | $V_H.4715*V_H.3418 + V_L.3418*V_L.4715$ |
| GOSA.V: | $V_H.4715*V_H.3418 + V_L.3418$-LiV-$V_L.4715$ |
| GOSA.J: | $V_H.3418$-LiA-$V_H.4715 + V_L.3418$-LiV-$V_L.4715$ |
| GOSA.AB: | $V_H.3418$-LiA-$V_H.4715 + V_L.3418*V_L.4715$ |
| GOSA.AA: | $V_H.3418*V_H.4715 + V_L.3418*V_L.4715$ |
| GOSA.Z: | $V_H.3418*V_H.4715 + V_L.3418$-LiV-$V_L.4715$ |

Table 2C

| | |
|---|---|
| GOSA.L: | $V_L.3418$-LiV-$V_L.4715$ |
| GOSA.Y: | $V_L.3418*V_L.4715$ |
| GOSA.AD: | $V_H.3418$-LiA-$V_H.4715$ |
| GOSA.AC: | $V_H.3418*V_H.4715$ |
| GOSA.C: | $V_H.4715$-LiA-$V_H.3418$ |
| GOSA.X: | $V_H.4715*V_H.3418$ |

(*) indicates that the two heavy chain domains or the two light chain domains are fused together without a connecting linker.

REFERENCES

Patent Literature

EP-0281604; GENEX/ENZON; SINGLE POLYPEPTIDE CHAIN BINDING MOLECULES; priority date Sep. 2, 1986.

WO 93/11161; ENZON, INC; MULTIVALENT ANTIGEN-BINDING PROTEINS; priority date Nov. 25, 19991.

WO 94/09131; SCOTGEN LIMITED; RECOMBINANT SPECIFIC BINDING PROTEIN; priority date Oct. 15, 19992).

WO 94/13804 (CAMBRIDGE ANTIBODY TECHNOLOGY/MEDICAL RESEARCH COUNCIL; MULTIVALENT AND MULTISPECIFIC BINDING PROTEINS, THEIR MANUFACTURE AND USE; first priority date Dec. 4, 1992.

WO 94/13806; THE DOW CHEMICAL COMPANY; MULTIVALENT SINGLE CHAIN ANTIBODIES; priority date Dec. 11, 19992.

WO 94/25591; UNILEVER N.V., UNILEVER PLC, Hamers, R., Hamers-Casterman, C., & Muyldermans, S; PRODUCTION OF ANTIBODIES OR (FUNCTIONALIZED) FRAGMENTS THEREOF DERIVED FROM HEAVY CHAIN IMMUNOGLOBULINS OF CAMELIDAE; first priority date Apr. 29, 1993.

Non-patent Literature

Anthony, J., Near, R., Wong, S. L., Iida, E., Ernst, E., Wittekind, M., Haber, E. and Ng, S-C; Molec. Immunol. 29

(1992) 1237–1247, PRODUCTION OF STABLE ANTI-DIGOXIN Fv IN *ESCHERICHIA COLI*.

Berry, M. J. and Davies, J.; *J. Chromatography* 597 (1992) 239–245; Use of antibody fragments in immunoaffinity chromatography: comparison of Fv fragments, $V_H$ fragments and paralog peptides.

Better, M., Chang, C. P., Robinson, R. R. and Horwitz A. H.; *Science* 240 (1988) 1041–1043; *Escherichia coli* Secretion of an Active Chimeric Antibody Fragment.

Bird, R. E., Hardman, K. D., Jacobson, J. W., Johnson, S., Kaufman, B. M., Lee, S. M., Lee, T., Pope, S. H., Riordan, G. S. and Whitlow, M.; *Science* 242 (1988) 423–426; Single-Chain Antigen-Binding Proteins.

Carter, P., Kelley, R. F., Rodrigues, M. L., Snedecor, B., Covarrubias, M., Velligan, M. D., Wong, W. L. T., Rowland, A. M., Kotts, C. E., Carver, M. E., Yang, M., Bourell, J. H., Shepard, H. M. and Henner, D.; *BIO/TECHNOLOGY* 10 (1992) 163–167; High level *Escherichia coli* expression and production of a bivalent humanized antibody fragment.

Cumber, A. J., Ward, E. S., Winter, G., Parnell, G. D. and Wawrzynczak. E. J.; *J. Immunol.* 149 (1992) 120–126; COMPARATIVE STABILITIES IN VITRO AND IN VIVO OF A RECOMBINANT MOUSE ANTIBODY FvCys FRAGMENT AND A bisFvCys CONJUGATE.

Firek, S., Draper, J., Owen. M. R. L., Gandecha, A., Cockburn, B., and Whitelam, G. C.; *Plant Mol. Biol.* 23 (1993) 861–870; Secretion of a functional single-chain Fv protein in transgenic tobacco plants and cell suspension cultures.

Givol, D.; *Molec. Immunol.* 28 (1991) 1379; THE MINIMAL ANTIGEN BINDING FRAGMENT OF ANTIBODIES—Fv FRAGMENT.

Hamers-Casteman, C., Atarhouch, T., Muyldermans, S., Robinson, G., Hamers, C., Bajyana Songa, E., Bendahman, N. and Hamers, R.; *Nature* 363 (1993) 446–448; Naturally occurring antibodies devoid of light chains.

Hiatt, A., Cafferkey, R. and Bowdish, K.; *Nature* 342 (1989) 76–78; Production of antibodies in transgenic plants.

Holliger, P., Prospero, T., and Winter, G.; *Proc. Natl. Acad. Sci. USA* 90 (1993) 6444–6448; "Diabodies": Small bivalent and bispecific antibody fragments.

Horwitz, A. H., Chang, C. P., Better, M., Hellstrom, K. E. and Robinson, R. R.; *Proc. Natl. Acad. Sci. USA* 85 (1988) 8678–8682; Secretion of functional antibody and Fab fragment from yeast cells.

Huston, J. S., Levinson, D., Mudgett-Hunter, M., Tai, M-S., Novotny, J., Margolies, M. N., Ridge, R. J., Bruccoleri, R. E., Haber, E., Crea, R. and Oppermann, H.; *Proc. Natl. Acad. Sci. USA* 85 (1988) 5879–5883; Protein engineering of antibody binding sites: Recovery of specific activity in an anti-digoxin single-chain Fv analogue produced in *Escherichia coli*.

Kostelny, S. A., Cole, M. S. and Tso, J. Y.; *J. Immunol.* 148 (1992) 1547–1553; FORMATION OF A BISPECIFIC ANTIBODY BY THE USE OF LEUCINE ZIPPERS.

Mallender, W. D., and Voss, Jr., E. W.; *J. Biol. Chem.* 269 (1994) 199–206; Construction, Expression, and Activity of a Bivalent Bispecific Single-chain Antibody.

Milstein, C. and Cuello, A. C.; *Nature*, 305 (1983) 537–540; Hybrid hybridomas and their use in immunohistochemistry.

Nyyssönen, E., Penttillä, M., Harkki, A., Saloheimo, A., Knowles, J. K. C. and Keränen, S.; *BIO/TECHNOLOGY Bio/tech.* 11 (1993) 591–595; Efficient Production of Antibody Fragments in Filamentous Fungus *Trichoderma reesei*.

Owen, M., Gandecha, A., Cockburn, B. and Whitelam G.; *BIO/TECENOLOGY* 10 (1992) 790–794; Synthesis of a functional anti-phytochrome single-chain Fv protein in transgenic tobacco.

Pack, P. and Plückthun, A.; *Biochemistry* 31 (1992) 1579–1584; Miniantibodies: Use of Amphiphatic Helices to Produce Functional, Flexibly Linked Dimeric Fv Fragments with High Avidity in *Escherichia coli*.

Skerra, A. and Plückthun, A.; *Science*, 240 (1988) 1038–1041; Assembly of a Functional Immunoglobulin Fv Fragment in *Escherichia coli*.

Taub, R., Gould, R. J., Ciccarone, T. M., Hoxie, J., Friedman, P. A., Shattil, S. J. and Garsky, V. M.; *J. Biol. Chem.* 264 (1989) 259–265; A Monoclonal Antibody against the Platelet Fibrinogen Receptor Contains a Sequence That Mimics a Receptor Recognition Domain in Fibrinogen.

Ward, E. S., Gussow, D., Griffiths, A. D., Jones, P. T. and Winter G.; *Nature* 341 (1989) 544–546; Binding activities of a repertoire of single immunoglobulin variable domains secreted from *Escherichia coli*.

Williams, W, V., Moss, D. A., Kieber-Emmons, T., Cohen, J. A., Myers, J. N., Weiner, D. B. and Greene, M. I.; *Proc. Natl. Acad. Sci. USA.* 86 (1989) 5537–5541; Development of biologically active peptides based on antibody structure.

We claim:

1. A bispecific or bivalent double head antibody fragment, which comprises a binding complex containing two polypeptide chains, whereby one polypeptide chain comprises two times a variable domain of a heavy chain ($V_H$) in series and the other polypeptide chain comprises two times a variable domain of a light chain ($V_L$) in series, and the binding complex contains two pairs of variable domains ($V_H$–A/$V_L$–A and $V_H$–B/$V_L$–B), wherein said double head antibody fragments have bifunctional antigen binding activity and said complex compirses one polypeptide chain wherein the variable regions are connected by a peptide linker or neither polypeptide chain is connected by a peptide linker.

2. An antibody fragment according to claim 1, in which one polypeptide chain comprises a first $V_H$ linked to a second $V_H$ and the other polypeptide chain comprises a first $V_L$ linked to a second $V_L$.

3. An antibody fragment according to claim 2, in which one polypeptide chain comprises a first $V_H$ ($V_H$–A) followed by a second $V_H$ ($V_H$–B) with or without a connecting peptide linker ($Li_H$), thus, and the other polypeptide chain comprises a first $V_L$ ($V_L$–A) preceded by a second $V_L$ ($V_L$–B) with or without a connecting peptide linker ($Li_L$), thus provided that the antibody fragment in total comprises only one peptide linker or no peptide linker.

4. An antibody fragment analogue according to claim 1, in which the two variable domains are from different Fvs resulting in a bispecific antibody fragment.

5. An antibody fragment according to claim 1, in which the specificities A and B are the same resulting in a bivalent antibody fragment.

6. A process for producing an antibody fragment according to any one of claims 1, 2 and 3–5, which comprises (1) transforming a Gram negative bacterial host by incorporating into that host a DNA encoding the two $V_H$'s in series with or without a connecting peptide linker and a DNA encoding the two $V_L$'s in series with or without a connecting peptide linker, (2) culturing such transformed host under conditions whereby the linked $V_H$'s and the linked $V_L$'s are formed, and (3) allowing the two linked $V_H$'s and the two connected $V_L$'s to combine to each other under formation of a double head antibody fragment whereby either the $V_H$'s are connected by a peptide linker or the $V_L$'s are connected by a peptide linker or neither $V_H$'s nor $V_L$'s are connected by a peptide linker, and (4) optionally collecting the double head antibody fragment.

7. A process according to claim 6, in which the host comprises *E. coli,* and higher eukaryotic organisms or cell cultures thereof.

8. An immunoassay comprising an antibody fragment as a binding means, the improvement wherein said antibody fragment comprises a double head antibody fragment according to claim 1.

9. An antibody fragment according to claim 1, comprising a peptide linker, said peptide linker comprising sufficient residues to span 30 to 35 Å.

* * * * *